(12) United States Patent
Jenkins et al.

(10) Patent No.: US 8,207,306 B2
(45) Date of Patent: Jun. 26, 2012

(54) TARGETED BINDING AGENTS DIRECTED TO SONIC HEDGEHOG HOMOLOG AND USES THEREOF

(75) Inventors: David Jenkins, Waltham, MA (US); Neil Michaud, Waltham, MA (US); Naomi Laing, Waltham, MA (US); Jaspal Singh Kang, Surrey (CA)

(73) Assignee: MedImmune, LLC, Gaithersburg, MD (US)

( * ) Notice: Subject to any disclaimer, the term of this patent is extended or adjusted under 35 U.S.C. 154(b) by 121 days.

(21) Appl. No.: 12/562,435

(22) Filed: Sep. 18, 2009

(65) Prior Publication Data

US 2010/0196388 A1     Aug. 5, 2010

Related U.S. Application Data

(60) Provisional application No. 61/119,558, filed on Dec. 3, 2008, provisional application No. 61/098,697, filed on Sep. 19, 2008.

(51) Int. Cl.
*C07K 16/00* (2006.01)
*C12P 21/08* (2006.01)
*C07K 1/00* (2006.01)

(52) U.S. Cl. ............ 530/387.1; 350/387.3; 350/387.7; 350/388.1; 350/388.23; 350/388.24

(58) Field of Classification Search ............... None
See application file for complete search history.

(56) References Cited

OTHER PUBLICATIONS

Ericson, Johan, et al., Cell, 87(4):661-673 (1996).
Watkins, D., et al., Nature, 422(6929):313-317 (2003).
Berman, David, et al., Nature, 425(6960):846-851 (2003).
Ma, Xiaoli, et al., International Journal of Cancer, 118(1):139-148 (2006).
International Search Report mailed Aug. 3, 2010, in corresponding International Application No. PCT/GB2009/051218.

*Primary Examiner* — Chun Dahle

(57) ABSTRACT

The invention relates to targeted binding agents against human sonic hedgehog homolog (Shh) and uses of such agents. More specifically, the invention relates to fully human monoclonal antibodies directed to Shh. The described targeted binding agents are useful in the treatment of diseases associated with the activity and/or overproduction of Shh and as diagnostics.

24 Claims, 7 Drawing Sheets

SEQUENCE LISTING

<160> NUMBER OF SEQ ID NOS: 84

<210> SEQ ID NO 1
<211> LENGTH: 366
<212> TYPE: DNA
<213> ORGANISM: Homo sapiens

<400> SEQUENCE: 1

```
caggtgtacc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa tgaatactat     180
gcagactccg tgaagggccg attcaccatc tccagagaca attccaagaa cacgctgtat     240
ctgcaaatga acagcctgag agccgaggac acggctgtct attactgtgc gagagatctc     300
tattactatg gttcggggag ccccttttgac tactggggcc agggaacccct ggtcaccgtc     360 tcctca                                                                366
```

<210> SEQ ID NO 2
<211> LENGTH: 122
<212> TYPE: PRT
<213> ORGANISM: Homo sapiens

<400> SEQUENCE: 2

```
Gln Val Tyr Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Glu Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Tyr Tyr Tyr Gly Ser Gly Ser Pro Phe Asp Tyr Trp
                100                 105                 110

Gly Gln Gly Thr Leu Val Thr Val Ser Ser
            115                 120
```

<210> SEQ ID NO 3
<211> LENGTH: 324
<212> TYPE: DNA
<213> ORGANISM: Homo sapiens

<400> SEQUENCE: 3
gaaatagtga tgacgcagtc tccagccacc ctgtctgtgt ctccagggga aagagccacc    60
ctctcctgca gggccagtca gagcgttagc agcaacttag cctggtacca gcagaaacct   120
ggccaggctc ccaggctcct catctttggt gtatctatta gggccactgg aatcccagcc   180
aggttcagtg gcagtgggtc tgggacagaa ttcactctca ccatcagcag cctgcagtct   240
gaagattttg cagtttatta ctgtcagcag tataatgact ggcctcgccc cggtttcggc   300
ggagggacca aggtggagat caaa                                          324

<210> SEQ ID NO 4
<211> LENGTH: 108
<212> TYPE: PRT
<213> ORGANISM: Homo sapiens

<400> SEQUENCE: 4

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Phe Gly Val Ser Ile Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asp Trp Pro Arg
                85                  90                  95

Pro Gly Phe Gly Gly Gly Thr Lys Val Glu Ile Lys
            100                 105

<210> SEQ ID NO 5
<211> LENGTH: 366
<212> TYPE: DNA
<213> ORGANISM: Homo sapiens

<400> SEQUENCE: 5
caggtgcagc tggtggagtc tgggggaggc gtggtccagc ctgggaggtc cctgagactc    60
tcctgtgcag cgtctggatt caccttcagt acttatggca tgcactgggt ccgccaggct   120
ccaggcaagg gctggagtg gtggcagtt atatggtatg atggaagtaa taatactat   180 gcagactccg tgaacggccg attcaccatc tcccgagaca attccaagaa tacgctgtat   240
ctgcaaatga acagcctgag aggcgaggac acggctgtgt attactgtgc gagagatcta   300
tattactatg gttcggggag cccctttgac tactggggcc agggaaccct ggtcaccgtc   360
tcctct                                                              366

<210> SEQ ID NO 6
<211> LENGTH: 122
<212> TYPE: PRT
<213> ORGANISM: Homo sapiens

<400> SEQUENCE: 6

```
Gln Val Gln Leu Val Glu Ser Gly Gly Val Gln Pro Gly Arg
1               5                  10                  15

Ser Leu Arg Leu Ser Cys Ala Ala Ser Gly Phe Thr Phe Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
        50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Asp Leu Tyr Tyr Tyr Gly Ser Gly Ser Pro Phe Asp Tyr Trp
            100                 105                 110

Gly Gln Gly Thr Leu Val Thr Val Ser Ser
            115                 120
```

<210> SEQ ID NO 7
<211> LENGTH: 324
<212> TYPE: DNA
<213> ORGANISM: Homo sapiens

<400> SEQUENCE: 7

```
gaaatagtga tgacgcagtc tccagccacc ctatctgtgt ctccagggga aagagtcacc      60
ctctcctgca gggccagtca gagtgttagc agcaacttag cctggtacca gcagaaacct     120
ggccaggctc ccaggctcct catctatggt gtatccatta gggccactgg aatcccagcc     180
aggttcagtg gcagtgggtc tgggacagag ttcactctca ccatcagcag cctgcagtct     240
gaagattttg cagtttatta ctgtcagcag tatgataact ggcctcgccc cggtttcggc     300
ggagggacca aggtggagat caaa                                            324
```

<210> SEQ ID NO 8
<211> LENGTH: 108
<212> TYPE: PRT
<213> ORGANISM: Homo sapiens

<400> SEQUENCE: 8

```
Glu Ile Val Met Thr Gln Ser Pro Ala Thr Leu Ser Val Ser Pro Gly
1               5                  10                  15

Glu Arg Val Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Val Ser Ile Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Arg
                85                  90                  95

Pro Gly Phe Gly Gly Gly Thr Lys Val Glu Ile Lys
            100                 105
```

<210> SEQ ID NO 9
<211> LENGTH: 366
<212> TYPE: DNA
<213> ORGANISM: Homo sapiens

<400> SEQUENCE: 9

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg gctggagtg gtggcagtt atatggaatg atggaagtaa tgaatactat     180
gcagactccg tgaagggccg attcaccatc tccagagaca attccaagaa cacgctgtat     240
ctgcaaatga acagcctgag agccgaggac acggctgtgt attactgtgc gagagatcta     300
tattactatg gttcggggag ccccttgac gactggggcc agggaacccct ggtcaccgtc     360 tcctca                                                                366
```

\<210\> SEQ ID NO 10
\<211\> LENGTH: 122
\<212\> TYPE: PRT
\<213\> ORGANISM: Homo sapiens

\<400\> SEQUENCE: 10

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asn Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Tyr Tyr Tyr Gly Ser Gly Ser Pro Phe Asp Asp Trp
            100                 105                 110

Gly Gln Gly Thr Leu Val Thr Val Ser Ser
        115                 120
```

\<210\> SEQ ID NO 11
\<211\> LENGTH: 324
\<212\> TYPE: DNA
\<213\> ORGANISM: Homo sapiens

\<400\> SEQUENCE: 11

```
gaaatagtga tgacgcagtc tccaggcacc ctgtctgtgt ctccagggga aagagccacc      60
ctctcctgca gggccagtca gagtgttggc agcaacttag cctggtacca acagaaacct     120
ggccaggctc ccaggctcct catctttggt gtatctatta gggccactgg agtcccagcc     180
aggttcagtg gcagtgggtc tgggacagag ttcactctca ccatcagcag cctgcagtct     240
gaagattttg cagtttatta ctgtcagcag tataatgact ggcctcgccc cggtttcggc     300
ggagggacca aggtggagat caaa                                            324
```

\<210\> SEQ ID NO 12
\<211\> LENGTH: 108
\<212\> TYPE: PRT
\<213\> ORGANISM: Homo sapiens

\<400\> SEQUENCE: 12

```
Glu Ile Val Met Thr Gln Ser Pro Gly Thr Leu Ser Val Ser Pro Gly
 1               5                  10                  15

Glu Arg Ala Thr Leu Ser Cys Arg Ala Ser Gln Ser Val Gly Ser Asn
            20                  25                  30
```

Leu Ala Trp Tyr Gln Gln Lys Pro Gly Gln Ala Pro Arg Leu Leu Ile
            35                  40                  45

Phe Gly Val Ser Ile Arg Ala Thr Gly Val Pro Ala Arg Phe Ser Gly
 50                      55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asp Trp Pro Arg
                 85                  90                  95

Pro Gly Phe Gly Gly Gly Thr Lys Val Glu Ile Lys
            100                 105

<210> SEQ ID NO 13
<211> LENGTH: 366
<212> TYPE: DNA
<213> ORGANISM: Homo sapiens

<400> SEQUENCE: 13
caggtgcagc tggtggagtc tgggggaggc gtggtccagc ctggagggtc cctgagactc         60
tcctgtgcag cgtctggatt caccttcagt acctatggca tgcactgggt ccgccaggct        120
ccaggcaagg ggctggagtg ggtggcagtt atatggtatg atggaagtaa taaatactat        180
gcagactccg tgaagggccg attcaccatc tccagagaca attccaagaa cacgctgaat        240
ctgcaaatga acagcctgag agccgaggac acggctgtgt attactgtgc gagagatcta        300
tattattatg gttcggggag cccctttgac tactggggcc agggaaccct ggtcaccgtc        360
tcctca                                                                   366

<210> SEQ ID NO 14
<211> LENGTH: 122
<212> TYPE: PRT
<213> ORGANISM: Homo sapiens

<400> SEQUENCE: 14

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                 85                  90                  95

Ala Arg Asp Leu Tyr Tyr Tyr Gly Ser Gly Ser Pro Phe Asp Tyr Trp
            100                 105                 110

Gly Gln Gly Thr Leu Val Thr Val Ser Ser
            115                 120

<210> SEQ ID NO 15
<211> LENGTH: 324
<212> TYPE: DNA
<213> ORGANISM: Homo sapiens

<400> SEQUENCE: 15
gaaatagtga tgacgcagtc tccagccacc ctgtctgtgt ctccagggga aagagccacc         60

```
ctctcctgca gggccagtca gagtgttagc agcaatttag cctggtacca gcagaaacct    120
ggccaggctc ccaggctcct catctttggt gtatccatta gggccactgg aatcccagcc    180
aggttcagtg gcagtgggtc tgggacagag ttcactctca ccatcagcag cctgcagtct    240
gaagattttg cagtttatta ctgtcagcag tataataact ggcctcgccc cggtttcggc    300
ggagggacca aggtggagat caaa                                            324
```

```
<210> SEQ ID NO 16
<211> LENGTH: 108
<212> TYPE: PRT
<213> ORGANISM: Homo sapiens

<400> SEQUENCE: 16
```

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Phe Gly Val Ser Ile Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Pro Gly Phe Gly Gly Gly Thr Lys Val Glu Ile Lys
            100                 105

```
<210> SEQ ID NO 17
<211> LENGTH: 366
<212> TYPE: DNA
<213> ORGANISM: Homo sapiens
<400> SEQUENCE: 17
caggtgcagc tggtggagtc tgggggaggc gtggtccagc ctgggaggtc cctgagactc     60
tcctgtgcag cgtctggatt caccttcagt acctatggca tgcactgggt ccgccaggct    120
ccaggcaagg gctggagtg gtggcagtt atatggtatg atggaagtaa tgaatactat    180
gcagactccg tgaagggccg attcaccatc tccagagaca attccaaaaa cacactatat    240
ctgcaaatga acagcctgag agccgaggac acggctgtct attactgtgc gagagatcta    300
tattactatg gttcggggag ccccttgac tactgggggcc agggaaccct ggtcaccgtc    360
tcgtca                                                                366
```

```
<210> SEQ ID NO 18
<211> LENGTH: 122
<212> TYPE: PRT
<213> ORGANISM: Homo sapiens

<400> SEQUENCE: 18
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Tyr Tyr Gly Ser Gly Ser Pro Phe Asp Tyr Trp
            100                 105                 110

Gly Gln Gly Thr Leu Val Thr Val Ser Ser
        115                 120

<210> SEQ ID NO 19
<211> LENGTH: 324
<212> TYPE: DNA
<213> ORGANISM: Homo sapiens

<400> SEQUENCE: 19
gaaatagtga tgacgcagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctttggt atatctatta gggccactgg aatcccagcc    180
aggttcagtg gcagtgggtc tgggacagag ttcactctca ccatcagcag cctgcagtct    240
gaagattttg cagtttatta ctgtcagcag tataatgact ggcctcgccc cggtttcggc    300
ggagggacca gggtggagat caaa                                           324

<210> SEQ ID NO 20
<211> LENGTH: 108
<212> TYPE: PRT
<213> ORGANISM: Homo sapiens

<400> SEQUENCE: 20

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Phe Gly Ile Ser Ile Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asp Trp Pro Arg
                85                  90                  95

Pro Gly Phe Gly Gly Gly Thr Arg Val Glu Ile Lys
            100                 105

<210> SEQ ID NO 21
<211> LENGTH: 369
<212> TYPE: DNA
<213> ORGANISM: Homo sapiens

<400> SEQUENCE: 21
gaggtgcagc tggtggagtc tgggggaggc ctggtcaagc ctggggggtc cctgagactc     60
tcctgtgcag cctctggatt caccttcagt agctatagca tgaactgggt ccgccaggct    120
ccagggaagg ggctggagtg ggtctcatcc tttagtagta gtagtagtta catttactac    180
gcagactcag tgaagggccg attcaccatc tccagagaca cgccaagaa ctcactgtat    240 ctgcaaatga acagcctgag agccgaggac acggctgtgt attactgtgc gagagaccgc    300

```
ggtgactacg tagactacta ctacggtatg gacgtctggg gccaagggac cacggtcacc    360
gtctcctca                                                             369
```

<210> SEQ ID NO 22
<211> LENGTH: 123
<212> TYPE: PRT
<213> ORGANISM: Homo sapiens

<400> SEQUENCE: 22

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Phe Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Asp Tyr Val Asp Tyr Tyr Tyr Gly Met Asp Val
            100                 105                 110

Trp Gly Gln Gly Thr Thr Val Thr Val Ser Ser
            115                 120
```

<210> SEQ ID NO 23
<211> LENGTH: 321
<212> TYPE: DNA
<213> ORGANISM: Homo sapiens

<400> SEQUENCE: 23

```
tcctatgagc tgactcagcc accctcagtg tccgtgtccc caggacagac agccagcatc     60
acctgctctg gagataagtt ggattataaa tatatttgct ggtatcagca gaagccaggc    120
cagtcccctg tgttggtcat ctatcaagat atcaagcggc cctcaggat cccctgagcga    180 ttctctggct ccaactctgg gaacacagcc actctgacca tcagcgggac ccaggctatg    240
gatgaggctg attattactg tcaggcgtgg gacagcaaca ctccattggt atttggcgga    300
gggaccaaac tgaccgtcct a                                              321
```

<210> SEQ ID NO 24
<211> LENGTH: 107
<212> TYPE: PRT
<213> ORGANISM: Homo sapiens

<400> SEQUENCE: 24

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Asp Tyr Lys Tyr Ile
            20                  25                  30

Cys Trp Tyr Gln Gln Lys Pro Gly Gln Ser Pro Val Leu Val Ile Tyr
        35                  40                  45

Gln Asp Ile Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Thr Pro Leu
```

```
                85                  90                  95
Val Phe Gly Gly Gly Thr Lys Leu Thr Val Leu
            100                 105

<210> SEQ ID NO 25
<211> LENGTH: 345
<212> TYPE: DNA
<213> ORGANISM: Homo sapiens

<400> SEQUENCE: 25
gaggtgcagc tggtggagtc tgggggaggc ttggtaaagc ctggggggtc ccttagactc    60
tcctgtgcag cctctggatt cactttcact aacgcctgga tgagctgggt ccgccaggct   120
ccagggaagg ggctggagtg ggttggccgt attaaaagca aaactgatgg tgggacaaca   180
gactacgctg cacccgtgaa aggcagattc accatctcaa gagatgattc aaaaaacacg   240
ctgtatctgc aaatgaacag cctgaaaacc gaggatatag ccgtgtatta ctgtaccaca   300
gataatttca ctggggccag ggaaccctg gtcaccgtct cctca                    345

<210> SEQ ID NO 26
<211> LENGTH: 115
<212> TYPE: PRT
<213> ORGANISM: Homo sapiens

<400> SEQUENCE: 26

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Ile Ala Val Tyr
                85                  90                  95

Tyr Cys Thr Thr Asp Asn Phe Asn Trp Gly Gln Gly Thr Leu Val Thr
            100                 105                 110

Val Ser Ser
        115

<210> SEQ ID NO 27
<211> LENGTH: 318
<212> TYPE: DNA
<213> ORGANISM: Homo sapiens

<400> SEQUENCE: 27
gaaatagtga tgacgcagtc tccagccacc ctgtctgtgt ctccagggga aagagccacc    60
ctctcctgca gggccagtca gagtattagc agcaacttag cctggtacca gcagaaacct   120
ggccaggctc cccggctcct catctatggt gcatccacca gggccactgg tatcccagcc   180
aggttcagtg gcagtgggtc tgggacagag ttcactctca ccatcagcag cctgcagtct   240
gaagattttg cagtttattt ctgtcagcag tatcatagct ggtggacgtt cggccagggg   300
accaaggtgg aaatccaa                                                 318

<210> SEQ ID NO 28
<211> LENGTH: 106
```

```
<212> TYPE: PRT
<213> ORGANISM: Homo sapiens

<400> SEQUENCE: 28

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr His Ser Trp Trp Thr
                85                  90                  95

Phe Gly Gln Gly Thr Lys Val Glu Ile Gln
            100                 105

<210> SEQ ID NO 29
<211> LENGTH: 351
<212> TYPE: DNA
<213> ORGANISM: Homo sapiens

<400> SEQUENCE: 29
caggtacagc tgcaggagtc gggcccagga ctggtgaagc cttcggagac cctgtccctc     60
acctgcactg tctctggtgg ctccatcagt agttactact ggacctggat ccggcagccc    120
ccagggaagg gactggagtg gattggttat atctattaca gtgggagcac caactacaac    180
ccctccctca agagtcgagt caccatatca gtagacacgt ccaagaacca gttctccctg    240
aagctgagct ctgtgaccgc tgcggacacg gccgtgtatt attgtgcgag agatagactc    300
ctttacggta tggacgtctg gggccaaggg accacggtca ccgtctcctc a             351

<210> SEQ ID NO 30
<211> LENGTH: 117
<212> TYPE: PRT
<213> ORGANISM: Homo sapiens

<400> SEQUENCE: 30

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Arg Leu Leu Tyr Gly Met Asp Val Trp Gly Gln Gly Thr Thr
            100                 105                 110

Val Thr Val Ser Ser
        115

<210> SEQ ID NO 31
```

```
<211> LENGTH: 321
<212> TYPE: DNA
<213> ORGANISM: Homo sapiens

<400> SEQUENCE: 31
gaaattgtgt tcacgcagtc tccaggcacc ctgtctttgt ctccggggga aggagccacc      60
ctctcctgta gggccagtca gattgttagc agcagctact tagcctggta ccagcagaaa     120
cctggccagg ctcccaggct cctcatttat ggtgcatcca gcagggccac tggcatccca     180
gacaggttca gtggcagtgg gtctgggaca gacttcactc tcaccatcag cagactggag     240
cctgaagatt ttgcagtgta ttactgtcag cactatggta gctcacctac tttcggcgga     300
gggatcaagg tggagatcaa a                                               321

<210> SEQ ID NO 32
<211> LENGTH: 107
<212> TYPE: PRT
<213> ORGANISM: Homo sapiens

<400> SEQUENCE: 32

Glu Ile Val Phe Thr Gln Ser Pro Gly Thr Leu Ser Leu Ser Pro Gly
1               5                   10                  15

Glu Gly Ala Thr Leu Ser Cys Arg Ala Ser Gln Ile Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Pro
                85                  90                  95

Thr Phe Gly Gly Gly Ile Lys Val Glu Ile Lys
            100                 105

<210> SEQ ID NO 33
<211> LENGTH: 363
<212> TYPE: DNA
<213> ORGANISM: Homo sapiens

<400> SEQUENCE: 33
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg ttcaacccta acagtggtgg cacaaactgt     180
gcacagaagt tcagggcag ggtcaccatg accaggaca cgtccatcag cacagcctac      240
atggagctga gcaggctgag atctgacgac acggccgtgt attactgtgc gagagaagca     300
gtggaatcct actactacgg tttggacgtc tggggccaag gaccacggt caccgtctcc     360 tca                                                                 363

<210> SEQ ID NO 34
<211> LENGTH: 121
<212> TYPE: PRT
<213> ORGANISM: Homo sapiens

<400> SEQUENCE: 34

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Val
        35                  40                  45

Gly Trp Phe Asn Pro Asn Ser Gly Gly Thr Asn Cys Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Glu Ala Val Glu Ser Tyr Tyr Tyr Gly Leu Asp Val Trp Gly
            100                 105                 110

Gln Gly Thr Thr Val Thr Val Ser Ser
            115                 120
```

<210> SEQ ID NO 35
<211> LENGTH: 330
<212> TYPE: DNA
<213> ORGANISM: Homo sapiens

<400> SEQUENCE: 35

```
cagtctgtgg tgactcagcc accctcagcg tctgggaccc ccgggcagag gatcaccatc     60
tcttgttctg gaagcagctc aacatcgga agtaattatg tgtactggta ccatcagctc    120
ccaggatcgg cccccaatct cctcatctat aggaataatc agcggccctc aggggtccct   180
gaccgattct ctggctccaa gtctggcacc tcagcctccc tggccatcag tgggctccgg   240
tccgaggatg aggctgatta cttctgtgca gtatgggatg acagcctgcg tggtgtggta   300
ttcggcggag ggaccaagct gaccgtccta                                     330
```

<210> SEQ ID NO 36
<211> LENGTH: 110
<212> TYPE: PRT
<213> ORGANISM: Homo sapiens

<400> SEQUENCE: 36

```
Gln Ser Val Val Thr Gln Pro Pro Ser Ala Ser Gly Thr Pro Gly Gln
 1               5                  10                  15

Arg Ile Thr Ile Ser Cys Ser Gly Ser Ser Ser Asn Ile Gly Ser Asn
            20                  25                  30

Tyr Val Tyr Trp Tyr His Gln Leu Pro Gly Ser Ala Pro Asn Leu Leu
        35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Phe Cys Ala Val Trp Asp Asp Ser Leu
                85                  90                  95

Arg Gly Val Val Phe Gly Gly Gly Thr Lys Leu Thr Val Leu
            100                 105                 110
```

<210> SEQ ID NO 37
<211> LENGTH: 363
<212> TYPE: DNA
<213> ORGANISM: Homo sapiens

<400> SEQUENCE: 37

```
gaggtgcagc tggtggagtc tggaggaggc ttgatccagc ctggggggtc cctgagactc     60
```

```
tcctgtgcag tctctgggtt caccgtcagt agcaactgca tgaactgggt ccgccaggct    120
ccagggaagg ggctggagtg ggtctcagtt atttatagcg gtggtaaaac agcctacgca    180
gactccgtga agggccgatt caccatctcc agagacaatt ccaagaacac gctgtgtctt    240
caaatgaaca gcctgagagc cgaggacacg gccgtgtatt actgtgcgag agattcctca    300
atggttgttg gattggggta cttcgatctt tggggccgtg gcaccctggt cactgtctcc    360
tca                                                                  363

<210> SEQ ID NO 38
<211> LENGTH: 121
<212> TYPE: PRT
<213> ORGANISM: Homo sapiens

<400> SEQUENCE: 38

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Thr Val Ser Ser Asn
            20                  25                  30

Cys Met Asn Trp Val Arg Gln Ala Pro Gly Lys Gly Leu Glu Trp Val
        35                  40                  45

Ser Val Ile Tyr Ser Gly Gly Lys Thr Ala Tyr Ala Asp Ser Val Lys
    50                  55                  60

Gly Arg Phe Thr Ile Ser Arg Asp Asn Ser Lys Asn Thr Leu Cys Leu
65                  70                  75                  80

Gln Met Asn Ser Leu Arg Ala Glu Asp Thr Ala Val Tyr Tyr Cys Ala
                85                  90                  95

Arg Asp Ser Ser Met Val Val Gly Leu Gly Tyr Phe Asp Leu Trp Gly
            100                 105                 110

Arg Gly Thr Leu Val Thr Val Ser Ser
        115                 120

<210> SEQ ID NO 39
<211> LENGTH: 318
<212> TYPE: DNA
<213> ORGANISM: Homo sapiens

<400> SEQUENCE: 39
tcctatgagc tgactcagcc accctcagtg tccgtgtccc caggactgac agccagcatc     60
acctgctctg gagataaaat tggggtataaa tatgcttcct ggtatcagca gaagccaggc    120
cagtcccctg tattggtcat ctatcaagat attaagcggc cctcagggat ccctgagcga    180
ttttctggct ccaactctgg gaacacagcc actctgacca tcagcgggac ccaggctatg    240
gatgaggctg actattactg tcaggcgtgg gacagcagca ctgtagtgtt tggcggaggg    300
accaagctga ccgtcctc                                                  318

<210> SEQ ID NO 40
<211> LENGTH: 106
<212> TYPE: PRT
<213> ORGANISM: Homo sapiens

<400> SEQUENCE: 40

Ser Tyr Glu Leu Thr Gln Pro Pro Ser Val Ser Val Ser Pro Gly Leu
1               5                   10                  15

Thr Ala Ser Ile Thr Cys Ser Gly Asp Lys Leu Gly Tyr Lys Tyr Ala
            20                  25                  30

Ser Trp Tyr Gln Gln Lys Pro Gly Gln Ser Pro Val Leu Val Ile Tyr
        35                  40                  45
```

```
Gln Asp Ile Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 41
<211> LENGTH: 363
<212> TYPE: DNA
<213> ORGANISM: Homo sapiens

<400> SEQUENCE: 41
gaggtgcagg tggtggagtc tggaggagac ttgatccagc ctggggggtc cctgagactc      60
tcctgtgtag cctctgggtt caccgtcagt agcaactaca tgaactgggt ccgccaggct     120
ccagggaagg ggctggagtg ggtctcagtt atttatagcg gtggtaacac atactacgca     180
gactccgtga agggccgatt caccatctcc agagacaatt ccaaaaacac gctgtatctt     240
caaatgaaca gcctgagagc cgaggacacg ccgtgtatt actgtgcgag agattcctcg     300
gtggttgttg gattggggta cttcgatctc tggggccgtg caccctggt cactgtctcc     360 tca                                                                  363

<210> SEQ ID NO 42
<211> LENGTH: 121
<212> TYPE: PRT
<213> ORGANISM: Homo sapiens

<400> SEQUENCE: 42

Glu Val Gln Val Val Glu Ser Gly Gly Asp Leu Ile Gln Pro Gly Gly
 1               5                  10                  15

Ser Leu Arg Leu Ser Cys Val Ala Ser Gly Phe Thr Val Ser Ser Asn
            20                  25                  30

Tyr Met Asn Trp Val Arg Gln Ala Pro Gly Lys Gly Leu Glu Trp Val
        35                  40                  45

Ser Val Ile Tyr Ser Gly Gly Asn Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Asp Ser Ser Val Val Val Gly Leu Gly Tyr Phe Asp Leu Trp Gly
            100                 105                 110

Arg Gly Thr Leu Val Thr Val Ser Ser
        115                 120

<210> SEQ ID NO 43
<211> LENGTH: 318
<212> TYPE: DNA
<213> ORGANISM: Homo sapiens

<400> SEQUENCE: 43
tcctatgaac tgactcagcc accctcagtg tccgtgtccc caggacagac agccagcatc      60
acctgctctg gagataaatt gggggctaac tatgcttcct ggtatcaaca gaagccaggc     120
cagtcccctg tgctggtcat ctttcaagat accaagcggc cctcagggat ccctgagcga     180
```

```
ttctctggct ccaactctgg gaacacagcc actctgacca tcagcgggac ccaggctatg     240
gatgaggctg actattactg tcaggcgtgg gacttcagca ctgtgatatt cggcggaggg     300
accaaactga ccgtccta                                                   318
```

<210> SEQ ID NO 44
<211> LENGTH: 106
<212> TYPE: PRT
<213> ORGANISM: Homo sapiens

<400> SEQUENCE: 44

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Ala Asn Tyr Ala
            20                  25                  30

Ser Trp Tyr Gln Gln Lys Pro Gly Gln Ser Pro Val Leu Val Ile Phe
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Phe Ser Thr Val Ile
                85                  90                  95

Phe Gly Gly Gly Thr Lys Leu Thr Val Leu
            100                 105

<210> SEQ ID NO 45
<211> LENGTH: 369
<212> TYPE: DNA
<213> ORGANISM: Homo sapiens

<400> SEQUENCE: 45

```
caggtgcagc tgcaggagtc gggcccagga ctggtgaagc cttcacagac cctgtccctc      60
acctgcactg tctctggtgg ctccatcaac agtggtggtt tctactggag ctggatccgc     120
cagcacccag ggaaaaacct ggagtggatt gggtccatct attacagtgg aacacctac      180 tataacccgt ccctcaagag tcgagtcacc atatcagtag acacgtctaa gaaccagttc     240
tccctgaagc tgacctctgt gactgccgcg gacacggccg tgtattactg tgcgagaggg     300
aatgactccg tgactacga ctggtacttc gatctctggg gccgtggcac cctggtcact      360
gtctcctca                                                             369
```

<210> SEQ ID NO 46
<211> LENGTH: 123
<212> TYPE: PRT
<213> ORGANISM: Homo sapiens

<400> SEQUENCE: 46

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Gly Phe Tyr Trp Ser Trp Ile Arg Gln His Pro Gly Lys Asn Leu Glu
        35                  40                  45

Trp Ile Gly Ser Ile Tyr Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

```
Ser Leu Lys Leu Thr Ser Val Thr Ala Ala Asp Thr Ala Val Tyr Tyr
                85                  90                  95

Cys Ala Arg Gly Asn Asp Ser Gly Asp Tyr Asp Trp Tyr Phe Asp Leu
            100                 105                 110

Trp Gly Arg Gly Thr Leu Val Thr Val Ser Ser
            115                 120
```

<210> SEQ ID NO 47
<211> LENGTH: 315
<212> TYPE: DNA
<213> ORGANISM: Homo sapiens

<400> SEQUENCE: 47

```
tcctatgagc tgactcagcc accctcagtg tccgtgtccc caggacagac agccagcatc    60
acctgctctg gagaaaaatt ggggtataaa tatgtttgtt ggtatcaaca gaagccaggc   120
cagtcccctg tgctggtcat ctttcacgat aacaagcggc cctcagggat ccctgagcga   180
ttctctggct ccaattctgg gaacacagcc actctgacca ttagcggggc ccaggctatg   240
gatgaggctg actattactg tcaggcgggg gacagcagcg ctgtattcgg cggagggacc   300
aagctgaccg tccta                                                   315
```

<210> SEQ ID NO 48
<211> LENGTH: 105
<212> TYPE: PRT
<213> ORGANISM: Homo sapiens

<400> SEQUENCE: 48

```
Ser Tyr Glu Leu Thr Gln Pro Pro Ser Val Ser Val Ser Pro Gly Gln
1               5                   10                  15

Thr Ala Ser Ile Thr Cys Ser Gly Glu Lys Leu Gly Tyr Lys Tyr Val
            20                  25                  30

Cys Trp Tyr Gln Gln Lys Pro Gly Gln Ser Pro Val Leu Val Ile Phe
        35                  40                  45

His Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Ala Gln Ala Met
65                  70                  75                  80

Asp Glu Ala Asp Tyr Tyr Cys Gln Ala Gly Asp Ser Ser Ala Val Phe
                85                  90                  95

Gly Gly Gly Thr Lys Leu Thr Val Leu
            100                 105
```

<210> SEQ ID NO 49
<211> LENGTH: 369
<212> TYPE: DNA
<213> ORGANISM: Homo sapiens

<400> SEQUENCE: 49

```
caggtgcagc tgcaggagtc gggcccagga ctggtgaagc cttcacagac cctgtccctc    60
acctgcactg tctctggtgg ctccatcaac agtggtggtt tctactggag ctggatccgc   120
cagcacccag ggaagggcct ggagtggatt gggtccatct attacagtgg gaacacctac   180 tataaccgt ccctcaagag tcgagtcacc atatcagtag acacgtctaa gaaccagttc   240
tccctgaagc tgagctctgt gactgccgcg gacacggccg tgtattactg tgcgagaggg   300
caggactccg gtgactacga ctggtacttc gatctctggg gccgtggcac cctggtcacc   360
gtctcctca                                                          369
```

<210> SEQ ID NO 50
<211> LENGTH: 123
<212> TYPE: PRT
<213> ORGANISM: Homo sapiens

<400> SEQUENCE: 50

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Gly Phe Tyr Trp Ser Trp Ile Arg Gln His Pro Gly Lys Gly Leu Glu
        35                  40                  45

Trp Ile Gly Ser Ile Tyr Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gln Asp Ser Gly Asp Tyr Asp Trp Tyr Phe Asp Leu
            100                 105                 110

Trp Gly Arg Gly Thr Leu Val Thr Val Ser Ser
        115                 120
```

<210> SEQ ID NO 51
<211> LENGTH: 315
<212> TYPE: DNA
<213> ORGANISM: Homo sapiens

<400> SEQUENCE: 51

```
tcctatgagc tgactcagcc accctcagtg tccgtgtccc caggacagac agccagcatc    60
acctgctctg gagaaaaatt ggggtataaa tatgtttctt ggtatcaaca gaagccaggc   120
cagtcccctg tgctggtcat ctttcacgat aacaagcggc catcagggat ccctgagcga   180
ttctctggct ccaattctgg gaacacagcc actctgacca tcagcgggac ccaggctatg   240
gatgaggctg actattactg tcaggcgggg gacagcagcg ctgtattcgg cggagggacc   300
aagctgaccg tccta                                                    315
```

<210> SEQ ID NO 52
<211> LENGTH: 105
<212> TYPE: PRT
<213> ORGANISM: Homo sapiens

<400> SEQUENCE: 52

```
Ser Tyr Glu Leu Thr Gln Pro Pro Ser Val Ser Val Ser Pro Gly Gln
1               5                   10                  15

Thr Ala Ser Ile Thr Cys Ser Gly Glu Lys Leu Gly Tyr Lys Tyr Val
            20                  25                  30

Ser Trp Tyr Gln Gln Lys Pro Gly Gln Ser Pro Val Leu Val Ile Phe
        35                  40                  45

His Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Gly Asp Ser Ser Ala Val Phe
                85                  90                  95

Gly Gly Gly Thr Lys Leu Thr Val Leu
            100                 105
```

<210> SEQ ID NO 53
<211> LENGTH: 315
<212> TYPE: DNA
<213> ORGANISM: Homo sapiens

<400> SEQUENCE: 53

```
tcctatgagc tgactcagcc accctcagtg tccgtgtccc caggacagac agccagcatc    60
acctgctctg gagaaaaatt ggggtataaa tatgtttctt ggtatcaaca gaagccaggc   120
cagtcccctg tgctggtcat ctatcacgat aacaagcggc catcagggat ccctgagcga   180
ttctctggct ccaattctgg gaacacagcc actctgacca tcagcgggac ccaggctatg   240
gatgaggctg actattactg tcaggcgggg gacagcagcg ctgtattcgg cggagggacc   300
aagctgaccg tccta                                                    315
```

<210> SEQ ID NO 54
<211> LENGTH: 105
<212> TYPE: PRT
<213> ORGANISM: Homo sapiens

<400> SEQUENCE: 54

```
Ser Tyr Glu Leu Thr Gln Pro Pro Ser Val Ser Val Ser Pro Gly Gln
1               5                   10                  15
Thr Ala Ser Ile Thr Cys Ser Gly Glu Lys Leu Gly Tyr Lys Tyr Val
            20                  25                  30
Ser Trp Tyr Gln Gln Lys Pro Gly Gln Ser Pro Val Leu Val Ile Tyr
        35                  40                  45
His Asp Asn Lys Arg Pro Ser Gly Ile Pro Glu Arg Phe Ser Gly Ser
    50                  55                  60
Asn Ser Gly Asn Thr Ala Thr Leu Thr Ile Ser Gly Thr Gln Ala Met
65                  70                  75                  80
Asp Glu Ala Asp Tyr Tyr Cys Gln Ala Gly Asp Ser Ser Ala Val Phe
                85                  90                  95
Gly Gly Gly Thr Lys Leu Thr Val Leu
            100                 105
```

<210> SEQ ID NO 55
<211> LENGTH: 321
<212> TYPE: DNA
<213> ORGANISM: Homo sapiens

<400> SEQUENCE: 55

```
tcctatgagc tgactcagcc accctcagtg tccgtgtccc caggacagac agccagcatc    60
acctgctctg gagataagtt ggattataaa tatattagct ggtatcagca gaagccaggc   120
cagtcccctg tgttggtcat ctatcaagat atcaagcggc catcagggat ccctgagcga   180
ttctctggct ccaactctgg gaacacagcc actctgacca tcagcgggac ccaggctatg   240
gatgaggctg actattactg tcaggcgtgg gacagcaaca ctccattggt attcggcgga   300
gggaccaagc tgaccgtcct a                                             321
```

<210> SEQ ID NO 56
<211> LENGTH: 107
<212> TYPE: PRT
<213> ORGANISM: Homo sapiens

<400> SEQUENCE: 56

```
Ser Tyr Glu Leu Thr Gln Pro Pro Ser Val Ser Val Ser Pro Gly Gln
```

```
                1               5                   10                  15
        Thr Ala Ser Ile Thr Cys Ser Gly Asp Lys Leu Asp Tyr Lys Tyr Ile
                        20                  25                  30

Ser Trp Tyr Gln Gln Lys Pro Gly Gln Ser Pro Val Leu Val Ile Tyr
                    35                  40                      45

Gln Asp Ile Lys Arg Pro Ser Gly Ile Pro Glu Arg Phe Ser Gly Ser
                50                      55                  60

Asn Ser Gly Asn Thr Ala Thr Leu Thr Ile Ser Gly Thr Gln Ala Met
        65                  70                  75                  80

Asp Glu Ala Asp Tyr Tyr Cys Gln Ala Trp Asp Ser Asn Thr Pro Leu
                            85                  90                  95

Val Phe Gly Gly Gly Thr Lys Leu Thr Val Leu
                        100                 105

<210> SEQ ID NO 57
<211> LENGTH: 366
<212> TYPE: DNA
<213> ORGANISM: Homo sapiens

<400> SEQUENCE: 57
caggtgcagc tggtggagtc tgggggaggc gtggtccagc ctggagggtc cctgagactc        60
tcctgtgcag cgtctggatt caccttcagt acctatggca tgcactgggt ccgccaggct       120
ccaggcaagg ggctggagtg ggtggcagtt atatggtatg atggaagtaa taatactat        180 gcagactccg tgaagggccg attcaccatc tccagagaca attccaagaa cacgctgtat       240
ctgcaaatga acagcctgag agccgaggac acggctgtgt attactgtgc gagagatcta       300
tattattatg gttcggggag ccccttttgac tactggggcc agggaaccct ggtcaccgtc       360
tcctca                                                                  366

<210> SEQ ID NO 58
<211> LENGTH: 122
<212> TYPE: PRT
<213> ORGANISM: Homo sapiens

<400> SEQUENCE: 58

Gln Val Gln Leu Val Glu Ser Gly Gly Gly Val Val Gln Pro Gly Arg
        1               5                   10                  15

Ser Leu Arg Leu Ser Cys Ala Ala Ser Gly Phe Thr Phe Ser Thr Tyr
                        20                  25                  30

Gly Met His Trp Val Arg Gln Ala Pro Gly Lys Gly Leu Glu Trp Val
                    35                  40                      45

Ala Val Ile Trp Tyr Asp Gly Ser Asn Lys Tyr Tyr Ala Asp Ser Val
                50                      55                  60

Lys Gly Arg Phe Thr Ile Ser Arg Asp Asn Ser Lys Asn Thr Leu Tyr
        65                  70                  75                  80

Leu Gln Met Asn Ser Leu Arg Ala Glu Asp Thr Ala Val Tyr Tyr Cys
                            85                  90                  95

Ala Arg Asp Leu Tyr Tyr Tyr Gly Ser Gly Ser Pro Phe Asp Tyr Trp
                        100                 105                 110

Gly Gln Gly Thr Leu Val Thr Val Ser Ser
                    115                 120

<210> SEQ ID NO 59
<211> LENGTH: 324
<212> TYPE: DNA
<213> ORGANISM: Homo sapiens
```

-continued

<400> SEQUENCE: 59

```
gaaatagtga tgacgcagtc tccagccacc ctgtctgtgt ctccagggga aagagccacc    60
ctctcctgca gggccagtca gagtgttagc agcaatttag cctggtacca gcagaaacct   120
ggccaggctc ccaggctcct catctatggt gtatccatta gggccactgg aatcccagcc   180
aggttcagtg gcagtgggtc tgggacagag ttcactctca ccatcagcag cctgcagtct   240
gaagattttg cagtttatta ctgtcagcag tataataact ggcctcgccc cggtttcggc   300
ggagggacca aggtggagat caaa                                          324
```

<210> SEQ ID NO 60
<211> LENGTH: 108
<212> TYPE: PRT
<213> ORGANISM: Homo sapiens

<400> SEQUENCE: 60

```
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Val Ser Ile Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Asn Trp Pro Arg
                85                  90                  95
Pro Gly Phe Gly Gly Gly Thr Lys Val Glu Ile Lys
            100                 105
```

<210> SEQ ID NO 61
<211> LENGTH: 120
<212> TYPE: PRT
<213> ORGANISM: Homo sapiens

<400> SEQUENCE: 61

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Tyr Tyr Tyr Gly Ser Gly Ser Tyr Phe Asp Tyr Trp Gly Gln
            100                 105                 110
Gly Thr Leu Val Thr Val Ser Ser
        115                 120
```

<210> SEQ ID NO 62
<211> LENGTH: 107
<212> TYPE: PRT
<213> ORGANISM: Homo sapiens

<400> SEQUENCE: 62

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 63
<211> LENGTH: 120
<212> TYPE: PRT
<213> ORGANISM: Homo sapiens

<400> SEQUENCE: 63

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Gly Ser Gly Ser Tyr Phe Asp Tyr Trp Gly Gln
            100                 105                 110

Gly Thr Leu Val Thr Val Ser Ser
        115                 120

<210> SEQ ID NO 64
<211> LENGTH: 107
<212> TYPE: PRT
<213> ORGANISM: Homo sapiens

<400> SEQUENCE: 64

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu

```
                    85                  90                  95

Thr Phe Gly Gly Gly Thr Lys Val Glu Ile Lys
                100                 105

<210> SEQ ID NO 65
<211> LENGTH: 120
<212> TYPE: PRT
<213> ORGANISM: Homo sapiens

<400> SEQUENCE: 65

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Gly Ser Gly Ser Tyr Phe Asp Tyr Trp Gly Gln
                100                 105                 110

Gly Thr Leu Val Thr Val Ser Ser
            115                 120

<210> SEQ ID NO 66
<211> LENGTH: 107
<212> TYPE: PRT
<213> ORGANISM: Homo sapiens

<400> SEQUENCE: 66

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
                100                 105

<210> SEQ ID NO 67
<211> LENGTH: 120
<212> TYPE: PRT
<213> ORGANISM: Homo sapiens

<400> SEQUENCE: 67

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30
```

```
Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Gly Ser Gly Ser Tyr Phe Asp Tyr Trp Gly Gln
                100                 105                 110

Gly Thr Leu Val Thr Val Ser Ser
            115                 120

<210> SEQ ID NO 68
<211> LENGTH: 107
<212> TYPE: PRT
<213> ORGANISM: Homo sapiens

<400> SEQUENCE: 68

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
                100                 105

<210> SEQ ID NO 69
<211> LENGTH: 120
<212> TYPE: PRT
<213> ORGANISM: Homo sapiens

<400> SEQUENCE: 69

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Gly Ser Gly Ser Tyr Phe Asp Tyr Trp Gly Gln
                100                 105                 110

Gly Thr Leu Val Thr Val Ser Ser
            115                 120
```

```
<210> SEQ ID NO 70
<211> LENGTH: 107
<212> TYPE: PRT
<213> ORGANISM: Homo sapiens

<400> SEQUENCE: 70

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 71
<211> LENGTH: 121
<212> TYPE: PRT
<213> ORGANISM: Homo sapiens

<400> SEQUENCE: 71

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Asp Tyr Tyr Tyr Gly Met Asp Val Trp Gly
            100                 105                 110

Gln Gly Thr Thr Val Thr Val Ser Ser
        115                 120

<210> SEQ ID NO 72
<211> LENGTH: 107
<212> TYPE: PRT
<213> ORGANISM: Homo sapiens

<400> SEQUENCE: 72

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
50                  55                  60
```

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Thr Ala Val
                85                  90                  95

Val Phe Gly Gly Gly Thr Lys Leu Thr Val Leu
            100                 105

<210> SEQ ID NO 73
<211> LENGTH: 114
<212> TYPE: PRT
<213> ORGANISM: Homo sapiens

<400> SEQUENCE: 73

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asn Trp Asn Trp Gly Gln Gly Thr Leu Val Thr Val
            100                 105                 110

Ser Ser

<210> SEQ ID NO 74
<211> LENGTH: 107
<212> TYPE: PRT
<213> ORGANISM: Homo sapiens

<400> SEQUENCE: 74

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 75
<211> LENGTH: 115
<212> TYPE: PRT
<213> ORGANISM: Homo sapiens

<400> SEQUENCE: 75

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Leu Leu Tyr Gly Met Asp Val Trp Gly Gln Gly Thr Thr Val Thr
                100                 105                 110

Val Ser Ser
        115

<210> SEQ ID NO 76
<211> LENGTH: 108
<212> TYPE: PRT
<213> ORGANISM: Homo sapiens

<400> SEQUENCE: 76

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
                100                 105

<210> SEQ ID NO 77
<211> LENGTH: 118
<212> TYPE: PRT
<213> ORGANISM: Homo sapiens

<400> SEQUENCE: 77

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Ala Val Tyr Tyr Tyr Gly Met Asp Val Trp Gly Gln Gly Thr
                100                 105                 110

Thr Val Thr Val Ser Ser
```

```
<210> SEQ ID NO 78
<211> LENGTH: 110
<212> TYPE: PRT
<213> ORGANISM: Homo sapiens

<400> SEQUENCE: 78

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu
            100                 105                 110

<210> SEQ ID NO 79
<211> LENGTH: 114
<212> TYPE: PRT
<213> ORGANISM: Homo sapiens

<400> SEQUENCE: 79

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Val Tyr Phe Asp Leu Trp Gly Arg Gly Thr Leu Val Thr Val
            100                 105                 110

Ser Ser

<210> SEQ ID NO 80
<211> LENGTH: 107
<212> TYPE: PRT
<213> ORGANISM: Homo sapiens

<400> SEQUENCE: 80

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
```

```
                    50                  55                  60
Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Ala Val
                 85                  90                  95

Val Phe Gly Gly Gly Thr Lys Leu Thr Val Leu
                100                 105

<210> SEQ ID NO 81
<211> LENGTH: 115
<212> TYPE: PRT
<213> ORGANISM: Homo sapiens

<400> SEQUENCE: 81

Glu Val Gln Leu Val Glu Ser Gly Gly Gly Leu Ile Gln Pro Gly Gly
  1               5                  10                  15

Ser Leu Arg Leu Ser Cys Ala Ala Ser Gly Phe Thr Val Ser Ser Asn
                 20                  25                  30

Tyr Met Ser Trp Val Arg Gln Ala Pro Gly Lys Gly Leu Glu Trp Val
                 35                  40                  45

Ser Val Ile Tyr Ser Gly Gly Ser Thr Tyr Tyr Ala Asp Ser Val Lys
             50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Val Val Val Tyr Phe Asp Leu Trp Gly Arg Gly Thr Leu Val Thr
                100                 105                 110

Val Ser Ser
        115

<210> SEQ ID NO 82
<211> LENGTH: 107
<212> TYPE: PRT
<213> ORGANISM: Homo sapiens

<400> SEQUENCE: 82

Ser Tyr Glu Leu Thr Gln Pro Pro Ser Val Ser Val Ser Pro Gly Gln
  1               5                  10                  15

Thr Ala Ser Ile Thr Cys Ser Gly Asp Lys Leu Gly Asp Lys Tyr Ala
                 20                  25                  30

Cys Trp Tyr Gln Gln Lys Pro Gly Gln Ser Pro Val Leu Val Ile Tyr
                 35                  40                  45

Gln Asp Ser Lys Arg Pro Ser Gly Ile Pro Glu Arg Phe Ser Gly Ser
             50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Ala Val
                 85                  90                  95

Val Phe Gly Gly Gly Thr Lys Leu Thr Val Leu
                100                 105

<210> SEQ ID NO 83
<211> LENGTH: 121
<212> TYPE: PRT
<213> ORGANISM: Homo sapiens

<400> SEQUENCE: 83
```

-continued

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Gly Asp Tyr Tyr Trp Tyr Phe Asp Leu Trp Gly
                100                 105                 110

Arg Gly Thr Leu Val Thr Val Ser Ser
            115                 120

<210> SEQ ID NO 84
<211> LENGTH: 107
<212> TYPE: PRT
<213> ORGANISM: Homo sapiens

<400> SEQUENCE: 84

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
                20                  25                  30

Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Val Phe Gly Gly Gly Thr Lys Leu Thr Val Leu
                100                 105
```

TARGETED BINDING AGENTS DIRECTED TO SONIC HEDGEHOG HOMOLOG AND USES THEREOF

CROSS REFERENCE TO RELATED APPLICATIONS

This application claims priority to and under the benefit of U.S. Provisional Patent Application No. 61/098,697 filed on Sep. 19, 2008 and U.S. Provisional Patent Application No. 61/119,558 filed on Dec. 3, 2008, the entire disclosures of which are incorporated by reference herein.

FIELD OF THE INVENTION

The invention relates to targeted binding agents against sonic hedgehog homolog (Shh) and uses of such agents. More specifically, the invention relates to fully human monoclonal antibodies directed to Shh. The described targeted binding agents are useful in the treatment of diseases associated with the activity and/or overproduction of Hedgehog proteins and as diagnostics.

DESCRIPTION OF THE RELATED ART

Hedgehog was identified in *Drosophila* as a mediator of embryonic patterning. There are three members of the hedgehog family in mammals, Sonic hedgehog (Shh), Indian hedgehog (Ihh), and Desert hedgehog (Dhh), which specify tissue patterning and regulate organ homeostasis by affecting cell growth and differentiation. The hedgehog proteins are ligands for the twelve-pass membrane spanning receptor Patched (Ptch in human, Ptc in mouse), which normally represses the function of the GCPR-like transmembrane protein Smoothened (SMO). Upon binding by Shh, repression of SMO by Patched is relieved allowing SMO to signal through members of the Gli family of transcription factors. Activation of transcription leads to the synthesis of pathways components such as Gli1 and Ptch.

Dysregulation of the hedgehog/SMO signaling pathway is implicated in tumorigenesis. Mutations that inactivate Ptch or constitutively activate Smo have been described in basal cell carcinoma, medulloblastoma and rhabdomyosarcoma. These mutations presumably result in constitutive activation of the pathway and drive tumorigenesis. Furthermore, over-expression of Shh has been described in numerous tumor types, such as prostate, pancreatic, small cell lung, colorectal, esophageal, gastric, melanoma, and multiple myeloma. In many cases upregulation of Gli1 and Ptch has been observed along with over-expression of Shh, supporting the conclusion that constitutive pathway activation in tumor cells may promote tumorigenesis in a ligand-dependent manner in some contexts. This model is support by the observation that ectopic over-expression of Shh in LNCaP prostate cancer cells enhances tumor growth in vivo (Fan 2004. Endocrinology 145:3961).

Several models have been proposed to explain how over-expression of Shh may lead to the development of cancer. In the first model, Shh is ectopically over-expressed by tumor cells, which generates an autocrine signal upon binding Ptch on the surface of tumor cells and induces cell proliferation. In the second model, Shh secreted by tumor cells activates SMO signaling in stromal cells, which in turn results in the production of factors that enhance tumor cell growth. In support of this model, it has been shown that tumor cells expressing Shh induce Gli1 expression in stromal cells (Fan et al. 2004. Endocrinology 145:3961; Yauch et al. 2008. Nature: 455, 406-410). Furthermore, coimplantation of mouse embryo fibroblasts (MEFs) promoted is tumor formation and growth of a suboptimal number of HT-29 tumor cells expressing Shh (Yauch et al. 2008. Nature: 455, 406-410). The ability of MEFs to enhance tumor growth required intact Shh/SMO signaling, as targeted deletion of SMO in MEFs resulted in substantially smaller tumors. Finally, Shh has been implicated in the proliferation and differentiation of stem cells in various tissues (Taipale and Beachy. 2001. Nature 411:349-354). As such, it has been proposed that Shh may promote tumorigenesis or relapse following treatment with chemotherapy and/or radiation by driving self-renewal of cancer stem cells.

Dependence of tumors on Shh/Smo signaling for growth and survival has been demonstrated in pre-clinical models with cyclopamine, a naturally occurring antagonist of the pathway derived from the corn lilly that acts through direct binding to SMO. Cyclopamine has been reported to inhibit the growth of numerous tumor cell lines in vitro and in vivo, including melanoma and prostate, pancreatic, and small cell lung tumors. The inhibitory effect of cyclopamine appeared to be specific, because even though it inhibited the growth of 22RV-1 prostate cancer xenografts, it did not inhibit the growth of 22RV-1 tumors stably over-expressing the downstream transcription factor Gli1 (Karhadkar et al. 2004. Nature 431:707). More recently, an unrelated small molecule SMO antagonist, HhAntag, has been shown to inhibit the growth of allograft medulloblastoma tumors in which the SMO pathway is constitutively activated through mutation of Ptc1 and human xenograft tumors over-expressing Shh (Romer et al. 2004. Cancer Cell 6:229; Yauch et al. 2008. Nature: 455, 406-410).

An antibody raised against the N-terminal signaling domain of rat Shh that cross-reacts with human Shh has been described (Ericson et al. 1996. Cell 87: 661-673). This antibody, named 5E1, has been used to demonstrate that specific blockade of the Shh pathway, as measured by a Gli1 reporter gene, correlated with inhibition of proliferation in established tumor cells from esophagus, stomach and pancreas. 5E1 also decreased the in vitro growth and viability of established small cell lung cancer (SCLC) cell lines and tumor cells derived from single passage pancreatic xenografts (Watkins et al. Nature, 422:313-317 (2003); Berman et al. 2003. Nature 426:846). Finally, 5E1 has been shown to inhibit the growth of HT55 and HT-29 colorectal tumor xenografts in vivo (Yauch et. 2008. Nature).

In addition to inhibiting growth and viability of tumor cells as single agents, Shh/SMO antagonists can augment the anti-tumor activity of chemotherapy and radiation (Chen et al. Cell Cycle, 6:1826-1830 (2007)). Sims-Mourtada et al. Clin Cancer Res., 12:6565-6572, (2006) is reported that the number of Gli1-positive cells increased dramatically as SEG-1 esophageal adenocarcinoma xenografts regrew following radiation treatment. The appearance of Gli1-staining cells preceded the increase of Ki67-positive cells, suggesting that Shh signaling may have promoted the expansion of a small population of refractory cells, such as putative cancer stem cells, ultimately resulting in tumor regrowth. Combination treatment of SEG-1 xenografts with paclitaxel and cyclopamine resulted in a superior efficacy compared to either agent alone.

The evidence cited above supports the rationale that antagonizing the Shh/SMO signaling pathway with a neutralizing antibody directed against Shh may be an effective therapy for numerous human cancers. Thus there is a need to identify novel inhibitors of Shh signaling.

SUMMARY OF THE INVENTION

The present invention relates to targeted binding agents that specifically bind to Shh and inhibit the biological activity of Shh. Embodiments of the invention relate to targeted binding agents that specifically bind to Shh and inhibit Shh binding to its receptor Patched, e.g., Patched-1 and/or Patched 2. In one embodiment, the antibody of the invention is specific for Shh.

Embodiments of the invention relate to targeted binding agents that specifically bind to Shh and inhibit binding of Shh to Patched-1 and/or Patched-2. In one embodiment, the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% of binding of Shh to Patched-1 compared to binding that would occur in the absence of the targeted binding agent.

In some embodiments of the invention, the targeted binding agent binds Shh with a binding affinity ($K_D$) of less than 5 nanomolar (nM). In other embodiments, the targeted binding agent binds with a $K_D$ of less than 4 nM, 3 nM, 2 nM or 1 nM. In some embodiments of the invention, the targeted binding agent binds Shh with a $K_D$ of less than 950 picomolar (pM). In some embodiments of the invention, the targeted binding agent binds Shh with a $K_D$ of less than 900 pM. In other embodiments, the targeted binding agent binds with a $K_D$ of less than 800 pM, 700 pM or 600 pM. In some embodiments of the invention, the targeted binding agent binds Shh with a $K_D$ of less than 500 pM. In other embodiments, the targeted binding agent binds with a $K_D$ of less than 400 pM. In still other embodiments, the targeted binding agent binds with a $K_D$ of less than 300 pM. In some other embodiments, the targeted binding agent binds with a $K_D$ of less than 200 pM. In some other embodiments, the targeted binding agent binds with a $K_D$ of less than 100 pM. In one specific embodiment, the targeted binding agent of the invention can bind human Shh with an affinity $K_D$ of less than 50, 40, 30, 20 or 10 pM. In another specific embodiment, the targeted binding agent of the invention can bind human Shh with an affinity $K_D$ of less than 1 pM. The $K_D$ may be assessed using a method described herein or known to one of skill in the art (e.g., a BIAcore assay, ELISA, FACS) (Biacore International AB, Uppsala, Sweden).

The binding properties of the targeted binding agent or antibody of the invention may also be measured by reference to the dissociation or association rates ($k_{off}$ and $k_{on}$ respectively).

In one embodiment of the invention, a targeted binding agent or an antibody may have an $k_{on}$ rate (antibody (Ab)+ antigen (Ag)$^{k_{on}} \rightarrow$Ab–Ag) of at least $10^4 M^{-1} s^{-1}$, at least $5 \times 10^4 M^{-1} s^{-1}$, at least $10^5 M^{-1} s^{-1}$, at least $2 \times 10^5 M^{-1} s^{-1}$, at least $5 \times 10^5 M^{-1} s^{-1}$, at least $10^6 M^{-1} s^{-1}$, at least $5 \times 10^6 M^{-1} s^{-1}$, at least $2 \times 10^5 M^{-1} s^{-1}$, at least $5 \times 10^5 M^{-1} s^{-1}$, at least $10^6 M^{-1} s^{-1}$, at least $5 \times 10^6 M^{-1} s^{-1}$, at least $10^7 M^{-1} s^{-1}$, $5 \times 10^7 M^{-1} s^{-1}$, or at least $10^8 M^{-1} s^{-1}$.

In another embodiment of the invention, targeted binding agent or an antibody may have a $k_{off}$ rate ((Ab–Ag)$^{k_{off}} \rightarrow$antibody (Ab)+antigen (Ag)) of less than $5 \times 10^{-1} s^{-1}$, less than $10^{-1} s^{-1}$, less than $5 \times 10^{-2} s^{-1}$, less than $10^{-2} s^{-1}$, less than $5 \times 10^{-3} s^{-1}$, less than $10^{-3} s^{-1}$, less than $5 \times 10^{-4} s^{-1}$, less than $10^{-4} s^{-1}$, less than $5 \times 10^{-5} s^{-1}$, less than $10^{-5} s^{-1}$, less than $5 \times 10^{-6} s^{-1}$, less than $10^{-6} s^{-1}$, less than $5 \times 10^{-7} s^{-1}$, less than $10^{-7} s^{-1}$, less than $5 \times 10^{-8} s^{-1}$, less than $10^{-8} s^{-1}$, less than $5 \times 10^{-9} s^{-1}$, less than $10^{-9} s^{-1}$, or less than $10^{-10} s^{-1}$.

The targeted binding agent of the invention specifically binds human Shh. In some examples, the targeted binding agent of the invention is cross-reactive with other Shh proteins from other species. In one embodiment, the targeted binding agent of the invention is cross-reactive with mouse Shh. In another embodiment, the targeted binding agent of the invention is cross-reactive with cynomolgus monkey Shh. In another embodiment, the targeted binding agent of the invention is cross-reactive with cynomolgus monkey Shh and mouse Shh.

In another embodiment, the targeted binding agent of the invention has nearly equivalent affinity for Shh proteins from other species. In one specific example, the human Shh targeted is binding agent of the invention has nearly equivalent affinity for mouse Shh. By equivalent level of affinity we mean that when the affinity with respect to human Shh4 is 1, the affinity of the antibody with respect to cynomolgus monkey Shh is between 0.2-5 or between 0.2-2.

In another embodiment, some of the targeted binding agents of the invention can bind related Hedgehog members. In one embodiment, the targeted binding agent can bind human Indian hedgehog homolog (IHH). For example, 6D7 can bind both human Indian hedgehog and mouse Indian hedgehog.

In another embodiment, some of the targeted binding agents of the invention fail to bind related Hedgehog members. For example, 3H8 and 1G1 do not exhibit binding to IHH Moreover, none of the targeted binding agents of the invention bind DHH.

In yet another embodiment, the targeted binding agent of the invention inhibits osteoblast differentiation of cells induced with Shh. In one example, activity possessed by the targeted binding agent can be demonstrated at an $IC_{50}$ concentration (a concentration to achieve 50% inhibition) of below 10 μM. In another example, the targeted binding agent of the invention can have an $IC_{50}$ concentration of less than 50, 40, 30, 20, 10, 9, 8, 7, 6, 5, 4, 3, or 2 nM.

In yet another embodiment, the targeted binding agent of the invention inhibits the induction of Gli1 and Patched-1 mRNA. In one example, activity possessed by the targeted binding agent can be demonstrated at an $IC_{50}$ concentration (a concentration to achieve 50% inhibition of) below 10 μM. In another example, the targeted binding agent of the invention can have an $IC_{50}$ concentration of less than 50, 40, 30, 20, 10, 5, 4 or 2 nM.

In yet another embodiment, the targeted binding agent can inhibit Gli1 and 2 and Patched-1 and 2. For example, the antibodies of the invention can exhibit greater than 50% inhibition of Gli1 and Patched-1 RNA as compared to a control (no target binding agent), e.g., 50%, 60%, 70%, 80%, 90%, or 95%.

In another embodiment of the invention, the targeted binding agent competes with any one of fully human monoclonal antibodies described herein for binding to Patched-1.

The targeted binding agents of the invention possess beneficial efficacious, pharmacokinetic, and/or pharmacodynamic properties. In one example, the targeted binding agents of the invention exhibit good safety properties, e.g., exhibit no cardiovascular toxic effects.

In some embodiments, the targeted binding agent can treat or prevent a condition is associated with abnormal Shh activity. In one embodiment of the invention, the targeted binding agent inhibits tumour cell proliferation. The targeted binding agents can be used in combination with other anti-cancer therapies such as chemotherapy regimes, or alone to inhibit tumor growth and/or metastasis.

The antibodies of the invention can be used in the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amyotrophic lateral sclerosis and the like, as well as spinocerebellar degenerations; and (iv) chronic immunological diseases of the nervous system or affecting the nervous system, including multiple sclerosis.

In some embodiments of the invention, the targeted binding agent is an antibody. In some embodiments of the invention, the targeted binding agent is a monoclonal antibody. In one embodiment of the invention, the targeted binding agent is a fully human monoclonal antibody. In another embodiment of the invention, the targeted binding agent is a fully human monoclonal antibody of the IgG1, IgG2, IgG3 or IgG4 isotype. In another embodiment of the invention, the targeted binding agent is a fully human monoclonal antibody of the IgG2 isotype. This isotype has reduced potential to elicit effector function in comparison with other isotypes, which may lead to reduced toxicity. In another embodiment of the invention, the targeted binding agent is a fully human monoclonal antibody of the IgG1 isotype. The IgG1 isotype has increased potential to elicit ADCC in comparison with other isotypes, which may lead to improved efficacy. The IgG1 isotype has improved stability in comparison with other isotypes, e.g. IgG4, which may lead to improved bioavailability, or improved ease of manufacture or a longer half-life. In one embodiment, the fully human monoclonal antibody of the IgG1 isotype is of the z, za or f allotype.

A further embodiment is a targeted binding agent or an antibody that specifically binds to Shh and comprises a sequence comprising one of the complementarity determining regions (CDR) sequences shown in Table 9. Embodiments of the invention include a targeted binding agent or antibody comprising a sequence comprising: any one of a CDR1, a CDR2 or a CDR3 is sequence from a heavy chain variable domain as shown in Table 9. A further embodiment is a targeted binding agent or an antibody that specifically binds to Shh and comprises a sequence comprising two of the CDR sequences of a heavy chain variable domain as shown in Table 9. In another embodiment the targeted binding agent or antibody comprises a sequence comprising a CDR1, a CDR2 and a CDR3 sequence of a heavy chain variable domain as shown in Table 9. In another embodiment the targeted binding agent or antibody comprises a sequence comprising one of the CDR sequences of a light chain variable domain as shown in Table 9. Embodiments of the invention include a targeted binding agent or antibody comprising a sequence comprising: any one of a CDR1, a CDR2 or a CDR3 sequence of a heavy chain variable domain as shown in Table 9. In another embodiment the targeted binding agent or antibody comprises a sequence comprising two of the CDR sequences of a heavy chain variable domain as shown in Table 9. In another embodiment the targeted binding agent or antibody comprises a sequence comprising a CDR1, a CDR2 and a CDR3 sequence of a light chain variable domain as shown in Table 9. In another embodiment the targeted binding agent or antibody may comprise a sequence comprising a CDR1, a CDR2 and a CDR3 sequence of a heavy chain variable domain as shown as shown in Table 9 and a CDR1, a CDR2 and a CDR3 sequence of a light chain variable domain as shown in Table 9. In some embodiments, the targeted binding agent is an antibody. In certain embodiments, the targeted binding agent is a fully human monoclonal antibody. In certain other embodiments, the targeted binding agent is a binding fragment of a fully human monoclonal antibody.

In one embodiment, the invention includes an antibody that immunospecifically binds to Shh and includes:

(a) a VH CDR1 of SEQ ID NO: 50 having an amino acid sequence identical to or comprising 1, 2, or 3 amino acid residue substitutions relative to the VH CDR1 of SEQ ID NO:50;

(b) a VH CDR2 of SEQ ID NO: 50 having an amino acid sequence identical to or comprising 1, 2, or 3 amino acid residue substitutions relative to the VH CDR2 of SEQ ID NO: 50;

(c) a VH CDR3 of SEQ ID NO: 50 having an amino acid sequence identical to or comprising 1, 2, or 3 amino acid residue substitutions relative to the VH CDR3 of SEQ ID NO: 50;

(d) a VL CDR1 of SEQ ID NO: 54 having an amino acid sequence identical to or comprising 1, 2, or 3 amino acid residue substitutions relative to VL CDR1 of SEQ ID NO: 54;

(e) a VL CDR2 of SEQ ID NO: 54 having an amino acid sequence identical to or comprising 1, 2, or 3 amino acid residue substitutions relative to the VL CDR2 of SEQ ID NO: 54; and (f) a VL CDR3 of SEQ ID NO: 54 having an amino acid sequence identical to or comprising 1, 2, or 3 amino acid residue substitutions relative to the VL CDR3 of SEQ ID NO: 54.

In yet another embodiment, the invention includes an antibody that immunospecifically binds to Shh and includes:

(a) a VH CDR1 of SEQ ID NO:14 having an amino acid sequence identical to or comprising 1, 2, or 3 amino acid residue substitutions relative to the VH CDR1 of SEQ ID NO:14;

(b) a VH CDR2 of SEQ ID NO:14 having an amino acid sequence identical to or comprising 1, 2, or 3 amino acid residue substitutions relative to the VH CDR2 of SEQ ID NO:14;

(c) a VH CDR3 of SEQ ID NO:14 having an amino acid sequence identical to or comprising 1, 2, or 3 amino acid residue substitutions relative to the VH CDR3 of SEQ ID NO:14;

(d) a VL CDR1 of SEQ ID NO:16 having an amino acid sequence identical to or comprising 1, 2, or 3 amino acid residue substitutions relative to VL CDR1 of SEQ ID NO:16;

(e) a VL CDR2 of SEQ ID NO:16 having an amino acid sequence identical to or comprising 1, 2, or 3 amino acid residue substitutions relative to the VL CDR2 of SEQ ID NO:16; and (f) a VL CDR3 of SEQ ID NO:16 having an amino acid sequence identical to or comprising 1, 2, or 3 amino acid residue substitutions relative to the VL CDR3 of SEQ ID NO:16.

In yet another embodiment, the invention includes an antibody that immunospecifically binds to Shh and includes:

(a) a VH CDR1 of SEQ ID NO:22 having an amino acid sequence identical to or comprising 1, 2, or 3 amino acid residue substitutions relative to the VH CDR1 of SEQ ID NO:22;

(b) a VH CDR2 of SEQ ID NO:22 having an amino acid sequence identical to or comprising 1, 2, or 3 amino acid residue substitutions relative to the VH CDR2 of SEQ ID NO:22;

(c) a VH CDR3 of SEQ ID NO:22 having an amino acid sequence identical to or comprising 1, 2, or 3 amino acid residue substitutions relative to the VH CDR3 of SEQ ID NO:22;

(d) a VL CDR1 of SEQ ID NO:24 having an amino acid sequence identical to or comprising 1, 2, or 3 amino acid residue substitutions relative to VL CDR1 of SEQ ID NO:24;

(e) a VL CDR2 of SEQ ID NO:24 having an amino acid sequence identical to or comprising 1, 2, or 3 amino acid residue substitutions relative to the VL CDR2 of SEQ ID NO:24; and (f) a VL CDR3 of SEQ ID NO:24 having an amino acid sequence identical to or comprising 1, 2, or 3 amino acid residue substitutions relative to the VL CDR3 of SEQ ID NO:24.

In another embodiment the targeted binding agent may comprise a sequence comprising any one of the CDR1, CDR2 or CDR3 of the variable heavy chain sequences encoded by a polynucleotide in a plasmid designated Mab6D7VHOP, Mab1G1VH, Mab3H8VH, and Mab6D7VH which were deposited at the American Type Culture Collection (ATCC) under number PTA-9504, PTA-9506, PTA-9518, or PTA-9506 on Sep. 17, 2008. In another embodiment the targeted binding agent may comprise a sequence comprising any one of the CDR1, CDR2 or CDR3 of the variable light chain sequences encoded by a polynucleotide in a plasmid designated Mab6D7VLOP, Mab1G1VL, Mab3H8VL, and Mab6D7VL which were deposited at the American Type Culture Collection (ATCC) under number PTA-9503, PTA-9509, PTA-9515, or PTA-9504 on Sep. 17, 2008.

In one embodiment, a targeted binding agent or an antibody of the invention comprises a variable heavy chain amino acid sequence comprising a CDR3 encoded by the polynucleotide in plasmid designated Mab6D7VHOP which was deposited at the American Type Culture Collection (ATCC) under number PTA-9504 on Sep. 17, 2008.

In one embodiment, a targeted binding agent or an antibody of the invention comprises a variable heavy chain amino acid sequence comprising a CDR3 encoded by the polynucleotide in plasmid designated Mab6D7VHOP which was deposited at the American Type Culture Collection (ATCC) under number PTA-9504 on Sep. 17, 2008 and a variable light chain amino acid sequence comprising a CDR3 encoded by the polynucleotide in plasmid designated Mab6D7VLOP which was deposited at the American Type Culture Collection (ATCC) under number PTA-9503 on Sep. 17, 2008.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab6D7VHOP which was deposited at the American Type Culture Collection (ATCC) under number PTA-9504 on Sep. 17, 2008.

In another embodiment, a targeted binding agent or an antibody of the invention comprises a variable light chain amino acid sequence comprising at least one, at least two, or at is least three of the CDRs of the antibody encoded by the polynucleotide in plasmid designated Mab6D7VLOP which was deposited at the American Type Culture Collection (ATCC) under number PTA-9503 on Sep. 17, 2008.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab6D7VHOP which was deposited at the American Type Culture Collection (ATCC) under number PTA-9504 on Sep. 17, 2008 and a variable light chain amino acid sequence comprising at least one, at least two, or at least three of the CDRs of the antibody encoded by the polynucleotide in plasmid designated Mab6D7VLOP which was deposited at the American Type Culture Collection (ATCC) under number PTA-9503 on Sep. 17, 2008.

In one embodiment, a targeted binding agent or an antibody of the invention comprises a variable heavy chain amino acid sequence comprising a CDR3 encoded by the polynucleotide in plasmid designated Mab1 G1VH which was deposited at the American Type Culture Collection (ATCC) under number PTA-9507 on Sep. 17, 2008.

In one embodiment, a targeted binding agent or an antibody of the invention comprises a variable heavy chain amino acid sequence comprising a CDR3 encoded by the polynucleotide in plasmid designated Mab1G1VH which was deposited at the American Type Culture Collection (ATCC) under number PTA-9507 on Sep. 17, 2008 and a variable light chain amino acid sequence comprising a CDR3 encoded by the polynucleotide in plasmid designated Mab1G1VL which was deposited at the American Type Culture Collection (ATCC) under number PTA-9509 on Sep. 17, 2008.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab1G1VH which was deposited at the American Type Culture Collection (ATCC) under number PTA-9507 on Sep. 17, 2008.

In another embodiment, a targeted binding agent or an antibody of the invention comprises a variable light chain amino acid sequence comprising at least one, at least two, or at least three of the CDRs of the antibody encoded by the polynucleotide in plasmid designated Mab1G1VL which was deposited at the American Type Culture Collection (ATCC) under is number PTA-9509 on Sep. 17, 2008.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab1G1VH which was deposited at the American Type Culture Collection (ATCC) under number PTA-9507 on Sep. 17, 2008 and a variable light chain amino acid sequence comprising at least one, at least two, or at least three of the CDRs of the antibody encoded by the polynucleotide in plasmid designated Mab1G1VL which was deposited at the American Type Culture Collection (ATCC) under number PTA-9509 on Sep. 17, 2008.

In one embodiment, a targeted binding agent or an antibody of the invention comprises a variable heavy chain amino acid sequence comprising a CDR3 encoded by the polynucleotide in plasmid designated Mab3H8VH which was deposited at the American Type Culture Collection (ATCC) under number PTA-9518 on Sep. 17, 2008.

In one embodiment, a targeted binding agent or an antibody of the invention comprises a variable heavy chain amino acid sequence comprising a CDR3 encoded by the polynucleotide in plasmid designated Mab3H8VH which was deposited at the American Type Culture Collection (ATCC) under number PTA-9518 on Sep. 17, 2008 and a variable light chain amino acid sequence comprising a CDR3 encoded by the polynucleotide in plasmid designated Mab3H8VL which was deposited at the American Type Culture Collection (ATCC) under number PTA-9515 on Sep. 17, 2008.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab3H8VH which was deposited at the American Type Culture Collection (ATCC) under number PTA-9518 on Sep. 17, 2008.

In another embodiment, a targeted binding agent or an antibody of the invention comprises a variable light chain amino acid sequence comprising at least one, at least two, or at least three of the CDRs of the antibody encoded by the polynucleotide in plasmid designated Mab3H8VL which was deposited at the American Type Culture Collection (ATCC) under number PTA-9515 on Sep. 17, 2008.

In another embodiment, a targeted binding agent or an antibody of the invention is comprises a variable heavy chain amino acid sequence comprising at least one, at least two, or at least three of the CDRs of the antibody encoded by the polynucleotide in plasmid designated Mab3H8VH which was deposited at the American Type Culture Collection (ATCC) under number PTA-9518 on Sep. 17, 2008 and a variable light chain amino acid sequence comprising at least one, at least two, or at least three of the CDRs of the antibody encoded by the polynucleotide in plasmid designated Mab3H8VL which was deposited at the American Type Culture Collection (ATCC) under number PTA-9515 on Sep. 17, 2008.

It is noted that those of ordinary skill in the art can readily accomplish CDR determinations. See for example, Kabat et al, Sequences of Proteins of Immunological Interest, Fifth Edition, NIH Publication 91-3242, Bethesda Md. (1991), vols. 1-3. Kabat provides multiple sequence alignments of immunoglobulin chains from numerous species antibody isotypes. The aligned sequences are numbered according to a single numbering system, the Kabat numbering system. The Kabat sequences have been updated since the 1991 publication and are available as an electronic sequence database (latest downloadable version 1997). Any immunoglobulin sequence can be numbered according to Kabat by performing an alignment with the Kabat reference sequence. Accordingly, the Kabat numbering system provides a uniform system for numbering immunoglobulin chains.

In one embodiment, the targeted binding agent or antibody comprises a sequence comprising any one of the heavy chain sequences shown in Table 9. In another embodiment, the targeted binding agent or antibody comprises a sequence comprising any one of the heavy chain sequences of antibodies 6D7, 3H8, 1G1, 6D7OP2, 6D7OP, or 3H8OP.

Light-chain promiscuity is well established in the art, thus, a targeted binding agent or antibody comprising a sequence comprising any one of the heavy chain sequences of antibodies 6D7, 3H8, 1G1, 6D7OP, 6D7OP2, or 3H8OP or another antibody as disclosed herein, may further comprise any one of the light chain sequences shown in Table 9 or of antibodies 6D7, 3H8 or 1G1, 6D7OP, 6D7OP2, 3H8OP or 1G1OP or another antibody as disclosed herein. In some embodiments, the antibody is a fully human monoclonal antibody.

In one embodiment, the targeted binding agent or antibody comprises a sequence comprising any one of the light chain sequences shown in Table 9. In another embodiment, the targeted binding agent or antibody comprises a sequence comprising any one of the light chain sequences of antibodies 6D7, 3H8 or 1G1, 6D7OP, 6D7OP2, 3H8OP or 1G1OP. In some embodiments, the antibody is a fully human monoclonal antibody.

In some embodiments, the targeting binding agent is a monoclonal antibody selected from the group consisting of: 1A12, 1G12, 1H10, 3H8, 4B6, 1G1, 1F4, 1H8, 1H12, 1C8, 1A5, 6D7, 6D7OP, 6D7OP2, 3H8OP or 1G1OP. In one embodiment, the targeted binding agent comprises one or more of fully human monoclonal antibodies 1A12, 1G12, 1H10, 3H8, 4B6, 1G1, 1F4, 1H8, 1H2, 1C8, 1A5, 6D7, 6D7OP, 6D7OP2, 3H8OP or 1G1OP. In certain embodiments, the targeting binding agent is monoclonal antibody 6D7. In certain other embodiments, the targeting binding agent is monoclonal antibody 3H8. In certain other embodiments, the targeting binding agent is monoclonal antibody 1G1. In certain other embodiments, the targeting binding agent is monoclonal antibody is 6D7OP. In certain other embodiments, the targeting binding agent is monoclonal antibody is 3H8OP. In certain other embodiments, the targeting binding agent is monoclonal antibody is 1G1OP.

In one embodiment a targeted binding agent or an antibody may comprise a sequence comprising a heavy chain CDR1, CDR2 and CDR3 selected from any one of the sequences shown in Table 9. In one embodiment a targeted binding agent or an antibody may comprise a sequence comprising a light chain CDR1, CDR2 and CDR3 selected from any one of the sequences shown in Table 9. In one embodiment a targeted binding agent or an antibody may comprise a sequence comprising a heavy chain CDR1, CDR2 and CDR3 selected from any one of the CDRs of antibodies 1A12, 1G12, 1H10, 3H8, 4B6, 1G1, 1F4, 1H8, 1H12, 1C8, 1A5, 6D7, or 6D7OP2.

In one embodiment a targeted binding agent or an antibody may comprise a sequence comprising a light chain CDR1, CDR2 and CDR3 selected from any one of the CDRs of antibodies 1A12, 1G12, 1H10, 3H8, 4B6, 1G1, 1F4, 1H8, 1H12, 1C8, 1A5, 6D7, or 6D7OP2.

In another embodiment the targeted binding agent or antibody may comprise a sequence comprising any one of a CDR1, a CDR2 or a CDR3 of any one of the fully human monoclonal antibodies 6D7, 3H8, 1G1, 6D7, or 6D7 as shown in Table 9. In another embodiment the targeted binding agent or antibody may comprise a sequence comprising any one of a CDR1, a CDR2 or a CDR3 of any one of the fully human monoclonal antibodies 6D7, 3H8, 1G1 or 6D7, as shown in Table 9. In one embodiment the targeted binding agent or antibody may comprise a sequence comprising a CDR1, a CDR2 and a CDR3 of fully human monoclonal antibody 6D7, 3H8, 1G1 or 6D7OP, as shown in Table 9. In another embodiment the targeted binding agent or is antibody may comprise a sequence comprising a CDR1, a CDR2 and a CDR3 of fully human monoclonal antibody 6D7, 3H8, 1G1 or 6D7OP, as shown in Table 9. In another embodiment the targeted binding agent or antibody may comprise a sequence comprising a CDR1, a CDR2 and a CDR3 of fully human monoclonal antibody 6D7, 3H8, 1G1 or 6D7, as shown in Table 9, and a CDR1, a CDR2 and a CDR3 sequence of fully human monoclonal antibody 6D7, 3H8, 1G1 or 6D7, as shown in Table 9. In some embodiments, the antibody is a fully human monoclonal antibody.

In another embodiment the targeted binding agent or antibody comprises a sequence comprising the CDR1, CDR2 and CDR3 sequence of a variable heavy chain and/or variable light chain of fully human monoclonal antibody 6D7, as shown in Table 9. In another embodiment the targeted binding agent or antibody comprises a sequence comprising the CDR1, CDR2 and CDR3 sequence of a variable heavy chain and/or variable light chain of fully human monoclonal antibody 3H8, as shown in Table 9. In another embodiment the targeted binding agent or antibody comprises a sequence comprising the CDR1, CDR2 and CDR3 sequence of a variable heavy chain and/or variable light chain of fully human monoclonal antibody 1G1, as shown in Table 9. In another embodiment the targeted binding agent or antibody comprises a sequence comprising the CDR1, CDR2 and CDR3 sequence of a variable heavy chain and/or variable light chain of fully human monoclonal antibody 6D7OP2 or 6D7OP, as shown in Table 9.

In some embodiments, the antibody is a fully human monoclonal antibody.

A further embodiment of the invention is a targeted binding agent or antibody comprising a sequence comprising the contiguous sequence spanning the framework regions and CDRs, specifically from FR1 through FR4 or CDR1 through CDR3, of any one of the sequences as shown in Table 9. In one embodiment the targeted binding agent or antibody comprises a sequence comprising the contiguous sequences spanning the framework regions and CDRs, specifically from FR1 through FR4 or CDR1 through CDR3, of any one of the sequences of monoclonal antibodies 6D7, 3H8, 1G1, as shown in Table 9. In some embodiments, the antibody is a fully human monoclonal antibody.

In another embodiment the agent or antibody, or antigen-binding portion thereof, comprises a heavy chain polypeptide comprising the sequence of SEQ ID NO.:14. In one embodiment, the agent or antibody, or antigen-binding portion thereof, further comprises a light is chain polypeptide comprising the sequence of SEQ ID NO.:16. In some embodiments, the antibody is a fully human monoclonal antibody.

One embodiment provides a targeted binding agent or antibody, or antigen-binding portion thereof, wherein the agent or antibody, or antigen-binding portion thereof, comprises a heavy chain polypeptide comprising the sequence of SEQ ID NO.:22. In one embodiment, the agent or antibody, or antigen-binding portion thereof, further comprises a light chain polypeptide comprising the sequence of SEQ ID NO.:24. In some embodiments, the antibody is a fully human monoclonal antibody.

In another embodiment the agent or antibody, or antigen-binding portion thereof, comprises a heavy chain polypeptide comprising the sequence of SEQ ID NO.:46. In another embodiment, the agent or antibody, or antigen-binding portion thereof, further comprises a light chain polypeptide comprising the sequence of SEQ ID NO.:48. In some embodiments, the antibody is a fully human monoclonal antibody.

In another embodiment the agent or antibody, or antigen-binding portion thereof, comprises a heavy chain polypeptide comprising the sequence of SEQ ID NO.:50. In another embodiment, the agent or antibody, or antigen-binding portion thereof, further comprises a light chain polypeptide comprising the sequence of SEQ ID NO.:52. In some embodiments, the antibody is a fully human monoclonal antibody.

In another embodiment the agent or antibody, or antigen-binding portion thereof, comprises a heavy chain polypeptide comprising the sequence of SEQ ID NO.:50 In another embodiment, the agent or antibody, or antigen-binding portion thereof, further comprises a light chain polypeptide comprising the sequence of SEQ ID NO.:56. In some embodiments, the antibody is a fully human monoclonal antibody.

In another embodiment the agent or antibody, or antigen-binding portion thereof, comprises a heavy chain polypeptide comprising the sequence of SEQ ID NO.:22. In another embodiment, the agent or antibody, or antigen-binding portion thereof, further comprises a light chain polypeptide comprising the sequence of SEQ ID NO.:56. In some embodiments, the antibody is a fully human monoclonal antibody.

In another embodiment the agent or antibody, or antigen-binding portion thereof, comprises a heavy chain polypeptide comprising the sequence of SEQ ID NO.:58. In another embodiment, the agent or antibody, or antigen-binding portion thereof, further comprises a light chain polypeptide comprising the sequence of SEQ ID NO.:60. In some embodiments, the antibody is a fully human monoclonal antibody.

In one embodiment the targeted binding agent or antibody comprises as many as twenty, sixteen, ten, nine or fewer, e.g. one, two, three, four or five, amino acid additions, substitutions, deletions, and/or insertions within the disclosed CDRs or heavy or light chain sequences. Such modifications may potentially be made at any residue within the CDRs. In some embodiments, the antibody is a fully human monoclonal antibody.

In one embodiment, the targeted binding agent or antibody comprises variants or derivatives of the CDRs disclosed herein, the contiguous sequences spanning the framework regions and CDRs (specifically from FR1 through FR4 or CDR1 through CDR3), the light or heavy chain sequences disclosed herein, or the antibodies disclosed herein. Variants include targeted binding agents or antibodies comprising sequences which have as many as twenty, sixteen, ten, nine or fewer, e.g. one, two, three, four, five or six amino acid additions, substitutions, deletions, and/or insertions in any of the CDR1, CDR2 or CDR3s as shown in Table 9, the contiguous sequences spanning the framework regions and CDRs (specifically from FR1 through FR4 or CDR1 through CDR3) as shown in Table 9, the light or heavy chain sequences disclosed herein, or with the monoclonal antibodies disclosed herein. Variants include targeted binding agents or antibodies comprising sequences which have at least about 60, 70, 80, 85, 90, 95, 98 or about 99% amino acid sequence identity with any of the CDR1, CDR2 or CDR3s as shown in Table 9, the contiguous sequences spanning the framework regions and CDRs (specifically from FR1 through FR4 or CDR1 through CDR3) as shown in Table 9, the light or heavy chain sequences disclosed herein, or with the monoclonal antibodies disclosed herein. The percent identity of two amino acid sequences can be determined by any method known to one skilled in the art, including, but not limited to, pairwise protein alignment. In one embodiment variants comprise changes in the CDR sequences or light or heavy chain polypeptides disclosed herein that are naturally occurring or are introduced by in vitro engineering of native sequences using recombinant DNA techniques or mutagenesis techniques. Naturally occurring variants include those which are generated in vivo in the corresponding germline nucleotide sequences during the generation of an antibody to a foreign antigen. In one embodiment the derivative may be a heteroantibody, which is an antibody in which two or more is antibodies are linked together. Derivatives include antibodies that have been chemically modified. Examples include covalent attachment of one or more polymers, such as water-soluble polymers, N-linked, or O-linked carbohydrates, sugars, phosphates, and/or other such molecules. The derivatives are modified in a manner that is different from the naturally occurring or starting antibody, either in the type or location of the molecules attached. Derivatives further include deletion of one or more chemical groups that are naturally present on the antibody.

In one embodiment, the targeted binding agent is a bispecific antibody. A bispecific antibody is an antibody that has binding specificity for at least two different epitopes. Methods for making bispecific antibodies are known in the art. (See, for example, Millstein et al, *Nature*, 305:537-539 (1983); Traunecker et al, *EMBO J*, 10:3655-3659 (1991); Suresh et al, *Methods in Enzymology*, 121:210 (1986); Kostelny et al, *J. Immunol*, 148(5):1547-1553 (1992); Hollinger et al, *Proc. Nall Acad. Sci. USA*, 90:6444-6448 (1993); Gruber et al, *J. Immunol*, 152:5368 (1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and EP 03089.)

In some embodiments of the invention, the targeted binding agent or antibody comprises a sequence comprising SEQ ID NO.: 14. In certain embodiments, SEQ ID NO.: 14 comprises any one of the combinations of germline and non-germline residues indicated by each row of Table 12. In some embodiments, SEQ ID NO: 14 comprises any one, any two, or three, or all three, of the germline residues as indicated in Table 12. In certain embodiments, SEQ ID NO.: 14 comprises any one of the unique combinations of germline and non-germline residues indicated by each row of Table 12. In other embodiments, the targeted binding agent or antibody is derived from a germline sequence, wherein one or more residues has been mutated to yield the corresponding germline residue at that position.

A further embodiment of the invention is a targeted binding agent or antibody that competes for binding to Shh with the targeted binding agent or antibodies of the invention. In another embodiment of the invention there is an antibody that competes for binding to Shh with the targeted binding agent or antibodies of the invention. In another embodiment the targeted binding agent or antibody competes for binding to Shh with any one of fully human monoclonal antibodies. "Competes" indicates that the targeted binding agent or antibody competes for binding to Shh with any one of fully human monoclonal antibodies 1A12, 1G12, 1H10, 3H8, 4B6, 1G1, 1F4, 1H8, 1H12, 1C8, 1A5, 6D7, 6D7OP, 6D7OP2, 3H8OP, or 1G1OP, i.e. competition is unidirectional.

Embodiments of the invention include a targeted binding agent or antibody which cross competes with any one of fully human monoclonal antibodies 1A12, 1G12, 1H10, 3H8, 4B6, 1G1, 1F4, 1H8, 1H12, 1C8, 1A5, 6D7, 6D7OP, 6D7OP2, 3H8OP, or 1G1OP, for binding to Shh. "Cross competes" indicates that the targeted binding agent or antibody competes for binding to Shh with any one of fully human monoclonal antibodies 1A12, 1G12, 1H10, 3H8, 4B6, 1G1, 1F4, 1H8, 1H12, 1C8, 1A5, 6D7, 6D7OP, 6D7OP2, 3H8OP, or 1G1OP, and vice versa, i.e. competition is bidirectional.

A further embodiment of the invention is a targeted binding agent or antibody that competes for binding to Shh. In another embodiment of the invention there is a targeted binding agent or antibody that cross-competes with the targeted binding agent or antibodies of the invention for binding to Shh.

A further embodiment of the invention is a targeted binding agent or antibody that binds to the same epitope on Shh as the targeted binding agent or antibodies of the invention. Embodiments of the invention also include a targeted binding agent or antibody that binds to the same epitope on Shh as any one of fully human monoclonal antibodies 1A12, 1G12, 1H10, 3H8, 4B6, 1G1, 1F4, 1H8, 1H12, 1C8, 1A5, 6D7, 6D7OP, 6D7OP2, 3H8OP, or 1G1OP.

Other embodiments of the invention include isolated nucleic acid molecules encoding any of the targeted binding agents or antibodies described herein, vectors having isolated nucleic acid molecules encoding the targeted binding agents or antibodies described herein or a host cell transformed with any of such nucleic acid molecules. Embodiments of the invention include a nucleic acid molecule encoding a fully human isolated targeted binding agent that specifically bind to Shh and inhibit binding of a Shh to Patched-1. The invention also encompasses polynucleotides that hybridize under stringent or lower stringency hybridization conditions, as defined herein, to polynucleotides that encode any of the targeted binding agents or antibodies described herein. Embodiments of the invention also include a vector comprising the nucleic acid molecule encoding the binding agent. Additional embodiments include a host cell comprising the vector of comprising the nucleic acid molecule.

As known in the art, antibodies can advantageously be, for example, polyclonal, oligoclonal, monoclonal, chimeric, humanised, and/or fully human antibodies.

It will be appreciated that embodiments of the invention are not limited to any particular form of an antibody or method of generation or production. In some embodiments of the invention, the targeted binding agent is a binding fragment of a fully human monoclonal antibody. For example, the targeted binding agent can be a full-length antibody (e.g., having an intact human Fc region) or an antibody-binding fragment (e.g., a Fab, Fab' or F(ab')$_2$, FV or dAb). In addition, the antibodies can be single-domain antibodies such as camelid or human single VH or VL domains that bind to Shh, such as a dAb fragment.

Embodiments of the invention described herein also provide cells for producing these antibodies. Examples of cells include hybridomas, or recombinantly created cells, such as Chinese hamster ovary (CHO) cells, variants of CHO cells (for example DG44) and NS0 cells that produce antibodies against Shh. Additional information about variants of CHO cells can be found in Andersen and Reilly (2004) Current Opinion in Biotechnology 15, 456-462, which is incorporated herein in its entirety by reference. The antibody can be manufactured from a hybridoma that secretes the antibody, or from a recombinantly engineered cell that has been transformed or transfected with a gene or genes encoding the antibody.

In addition, one embodiment of the invention is a method of producing an antibody of the invention by culturing host cells under conditions wherein a nucleic acid molecule is expressed to produce the antibody followed by recovering the antibody. It should be realized that embodiments of the invention also include any nucleic acid molecule that encodes an antibody or fragment of an antibody of the invention including nucleic acid sequences optimized for increasing yields of antibodies or fragments thereof when transfected into host cells for antibody production.

A further embodiment herein includes a method of producing antibodies that specifically bind to Shh and inhibit the biological activity of Shh, by immunizing a mammal with cells expressing human Shh, isolated cell membranes containing human Shh, purified human Shh, or a fragment thereof, and/or one or more orthologous sequences or fragments thereof.

In other embodiments the invention provides compositions, including a targeted binding agent or antibody of the invention or binding fragment thereof, and a pharmaceutically acceptable carrier or diluent.

Still further embodiments of the invention include methods of effectively treating an animal suffering from a proliferative, angiogenic, disease by administering to the animal a therapeutically effective dose of a targeted binding agent that specifically binds to Shh. In certain embodiments the method further comprises selecting an animal in need of treatment a tumor, cancer, and/or a cell proliferative disorder, and administering to the animal a therapeutically effective dose of a targeted binding agent that specifically binds to Shh.

Still further embodiments of the invention include methods of effectively treating an animal suffering from a neoplastic disease by administering to the animal a therapeutically effective dose of a targeted binding agent that specifically binds to Shh. In certain embodiments the method further comprises selecting an animal in need of treatment for a neoplastic disease, and administering to the animal a therapeutically effective dose of a targeted binding agent that specifically binds to Shh.

Still further embodiments of the invention include methods of effectively treating an animal suffering from a malignant tumour by administering to the animal a therapeutically effective dose of a targeted binding agent that specifically binds to Shh. In certain embodiments the method further comprises selecting an animal in need of treatment for a malignant tumour, and administering to the animal a therapeutically effective dose of a targeted binding agent that specifically binds to Shh.

Still further embodiments of the invention include methods of effectively treating an animal suffering from a disease or condition associated with Shh expression by administering to the animal a therapeutically effective dose of a targeted binding agent that specifically binds to Shh. In certain embodiments the method further comprises selecting an animal in need of treatment for a disease or condition associated with Shh expression, and administering to the animal a therapeutically effective dose of a targeted binding agent that specifically binds to Shh.

A malignant tumour may be selected from the group consisting of: melanoma, small cell lung cancer, non-small cell lung cancer, glioma, hepatocellular (liver) carcinoma, thyroid tumour, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies and epidermoid is carcinoma.

Treatable proliferative or angiogenic diseases include neoplastic diseases, such as, melanoma, small cell lung cancer, non-small cell lung cancer, glioma, advanced non-small cell lung cancer, hepatocellular (liver) carcinoma, thyroid tumour, gastric (stomach) cancer, gallbladder cancer, prostate cancer, breast cancer, ovarian cancer, bladder cancer, renal cell cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies, epidermoid carcinoma and leukemia including chronic myelogenous leukemia (CML) including Gleevec-resistant CML, lymphoma including Hodgkin's and Non-Hodgkin's lymphoma; and myeloma including multiple myeloma. In one embodiment the present invention is suitable for use in inhibiting Shh, in patients with a tumour that is dependent alone, or in part, on Shh.

Still further embodiments of the invention include use of a targeted binding agent or antibody of the invention in the preparation of a medicament for the treatment of an animal suffering from a proliferative, or angiogenic related disease. In certain embodiments the use further comprises selecting an animal in need of treatment for a proliferative, or angiogenic-related disease.

Still further embodiments of the invention include use of a targeted binding agent or antibody of the invention in the preparation of a medicament for the treatment of an animal suffering from a neoplastic disease. In certain embodiments the use further comprises selecting an animal in need of treatment for a neoplastic disease.

Still further embodiments of the invention include use of a targeted binding agent or antibody of the invention in the preparation of a medicament for the treatment of an animal suffering from a non-neoplastic disease. In certain embodiments the use further comprises selecting an animal in need of treatment for a non-neoplastic disease.

Still further embodiments of the invention include use of a targeted binding agent or antibody of the invention in the preparation of a medicament for the treatment of an animal suffering from a malignant tumour. In certain embodiments the use further comprises selecting an animal in need of treatment for a malignant tumour.

Still further embodiments of the invention include use of a targeted binding agent or antibody of the invention in the preparation of a medicament for the treatment of an animal suffering from a disease or condition associated with Shh expression. In certain embodiments the use further comprises selecting an animal in need of treatment for a disease or condition associated with Shh expression.

Still further embodiments of the invention include a targeted binding agent or antibody of the invention for use as a medicament for the treatment of an animal suffering from a proliferative or angiogenic-related disease.

Still further embodiments of the invention include a targeted binding agent or antibody of the invention for use as a medicament for the treatment of an animal suffering from a neoplastic disease.

Still further embodiments of the invention include a targeted binding agent or antibody of the invention for use as a medicament for the treatment of an animal suffering from a malignant tumour.

Still further embodiments of the invention include a targeted binding agent or antibody of the invention for use as a medicament for the treatment of an animal suffering from a disease or condition associated with Shh expression.

Still further embodiments of the invention include a targeted binding agent or antibody of the invention for use as a medicament for the treatment of an animal suffering from a Shh induced disease.

In one embodiment treatment of a a neoplastic disease;
a malignant tumour;
a neurological disease;
an ocular disease;
a chronic inflammatory disease;
a disease or condition associated with Shh expression; or
comprises managing, ameliorating, preventing, any of the aforementioned diseases or conditions.

In one embodiment treatment of a neoplastic disease comprises inhibition of tumour growth, tumour growth delay, regression of tumour, shrinkage of tumour, increased time to regrowth of tumour on cessation of treatment, increased time to tumour recurrence, slowing of disease progression.

In some embodiments of the invention, the animal to be treated is a human.

In some embodiments of the invention, the targeted binding agent is a fully human monoclonal antibody.

In some embodiments of the invention, the targeted binding agent is selected from the group consisting of fully human monoclonal antibodies 1A12, 1G12, 1H10, 3H8, 4B6, 1G1, 1F4, 1H8, 1H12, 1C8, 1A5, 6D7, 6D7OP, 6D7OP2, 3H8OP, or 1G1OP.

Embodiments of the invention include a conjugate comprising the targeted binding agent as described herein, and a therapeutic agent. In some embodiments of the invention, the therapeutic agent is a toxin. In other embodiments, the therapeutic agent is a radioisotope. In still other embodiments, the therapeutic agent is a pharmaceutical composition.

In another aspect, a method of selectively killing a cancerous cell in a patient is provided. The method comprises administering a fully human antibody conjugate to a patient. The fully human antibody conjugate comprises an antibody that can bind to Shh and an agent. The agent is a toxin, a radioisotope, or another substance that will kill a cancer cell. The antibody conjugate thereby selectively kills the cancer cell.

In one aspect, a conjugated fully human antibody that specifically binds to Shh is provided. Attached to the antibody is an agent, and the binding of the antibody to a cell results in the delivery of the agent to the cell. In one embodiment, the above conjugated fully human antibody binds to an extracellular domain of Shh. In another embodiment, the antibody and conjugated toxin are internalized by a cell that expresses Shh. In another embodiment, the agent is a cytotoxic agent. In another embodiment, the agent is, for example saporin, or auristatin, pseudomonas exotoxin, gelonin, ricin, calicheamicin or maytansine-based immunoconjugates, and the like. In still another embodiment, the agent is a radioisotope.

The targeted binding agent or antibody of the invention can be administered alone, or can be administered in combination with additional antibodies or chemotherapeutic drugs or radiation therapy. For example, a monoclonal, oligoclonal or polyclonal mixture of Shh antibodies that block cell proliferation can be administered in combination with a drug shown to inhibit tumour cell proliferation. Moreover, the Shh targeting agents of the invention can used in patients who have failed other chemotherapy treatments, for example, treatments that include anti-VEGF is agents.

Another embodiment of the invention includes a method of diagnosing diseases or conditions in which an antibody as disclosed herein is utilized to detect the level of Shh in a patient or patient sample. In one embodiment, the patient sample is blood or blood serum or urine. In further embodiments, methods for the identification of risk factors, diagnosis of disease, and staging of disease is presented which involves the identification of the expression and/or overexpression of Shh using anti-Shh antibodies. In some embodiments, the methods comprise administering to a patient a fully human antibody conjugate that selectively binds to Shh on a cell. The antibody conjugate comprises an antibody that specifically binds to Shh and a label. The methods further comprise observing the presence of the label in the patient. A relatively high amount of the label will indicate a relatively high risk of the disease and a relatively low amount of the label will indicate a relatively low risk of the disease. In one embodiment, the label is a green fluorescent protein.

The invention further provides methods for assaying the level of Shh in a patient sample, comprising contacting an antibody as disclosed herein with a biological sample from a patient, and detecting the level of binding between said antibody and Shh in said sample. In more specific embodiments, the biological sample is blood, plasma or serum.

Another embodiment of the invention includes a method for diagnosing a condition associated with the expression of Shh in a cell by contacting the serum or a cell with an antibody as disclosed herein, and thereafter detecting the presence of Shh. In one embodiment the condition can be a proliferative-related disease including, but not limited to, a neoplastic disease.

In another embodiment, the invention includes an assay kit for detecting Shh in mammalian tissues, cells, or body fluids to screen for Shh-related diseases. The kit includes an antibody as disclosed herein and a means for indicating the reaction of the antibody with Shh, if present. In one embodiment the antibody is a monoclonal antibody. In one embodiment, the antibody that binds Shh is labeled. In another embodiment the antibody is an unlabeled primary antibody and the kit further includes a means for detecting the primary antibody. In one embodiment, the means for detecting includes a labeled second antibody that is an anti-immunoglobulin. The antibody may be labeled with a marker selected from the group consisting of a fluorochrome, an enzyme, a radionuclide and a radiopaque material.

In some embodiments, the targeted binding agents or antibodies as disclosed herein can be modified to enhance their capability of fixing complement and participating in complement-dependent cytotoxicity (CDC). In other embodiments, the targeted binding agents or antibodies can be modified to enhance their capability of activating effector cells and participating in antibody-dependent cytotoxicity (ADCC). In yet other embodiments, the targeted binding agents or antibodies as disclosed herein can be modified both to enhance their capability of activating effector cells and participating in antibody-dependent cytotoxicity (ADCC) and to enhance their capability of fixing complement and participating in complement-dependent cytotoxicity (CDC).

In some embodiments, the targeted binding agents or antibodies as disclosed herein can be modified to reduce their capability of fixing complement and participating in complement-dependent cytotoxicity (CDC). In other embodiments, the targeted binding agents or antibodies can be modified to reduce their capability of activating effector cells and participating in antibody-dependent cytotoxicity (ADCC). In yet other embodiments, the targeted binding agents or antibodies as disclosed herein can be modified both to reduce their capability of activating effector cells and participating in antibody-dependent cytotoxicity (ADCC) and to reduce their capability of fixing complement and participating in complement-dependent cytotoxicity (CDC).

In certain embodiments, the half-life of a targeted binding agent or antibody as disclosed herein and of compositions of the invention is at least about 4 to 7 days. In certain embodiments, the mean half-life of a targeted binding agent or antibody as disclosed herein and of compositions of the invention is at least about 2 to 5 days, 3 to 6 days, 4 to 7 days, 5 to 8 days, 6 to 9 days, 7 to 10 days, 8 to 11 days, 8 to 12, 9 to 13, 10 to 14, 11 to 15, 12 to 16, 13 to 17, 14 to 18, 15 to 19, or 16 to 20 days. In other embodiments, the mean half-life of a targeted binding agent or antibody as disclosed herein and of compositions of the invention is at least about 17 to 21 days, 18 to 22 days, 19 to 23 days, 20 to 24 days, 21 to 25, days, 22 to 26 days, 23 to 27 days, 24 to 28 days, 25 to 29 days, or 26 to 30 days. In still further embodiments the half-life of a targeted binding agent or antibody as disclosed herein and of compositions of the invention can be up to about 50 days. In certain embodiments, the half-lives of antibodies and of compositions of the invention can be prolonged by methods known in the art. Such prolongation can in turn reduce the amount and/or frequency of dosing of the antibody compositions. Antibodies with improved in vivo half-lives and methods for preparing them are disclosed in U.S. Pat. No. 6,277,375; and International Publication Nos. WO 98/23289 and WO 97/4661.

In another embodiment, the invention provides an article of manufacture including a container. The container includes a composition containing a targeted binding agent or antibody as disclosed herein, and a package insert or label indicating that the composition can be used to treat cell proliferation-related diseases, including, but not limited to, diseases characterised by the expression or overexpression of Shh.

In other embodiments, the invention provides a kit comprising a composition containing a targeted binding agent or antibody as disclosed herein, and instructions to administer the composition to a subject in need of treatment.

The present invention provides formulation of proteins comprising a variant Fc region. That is, a non-naturally occurring Fc region, for example an Fc region comprising one or more non-naturally occurring amino acid residues. Also encompassed by the variant Fc regions of present invention are Fc regions that comprise amino acid deletions, additions and/or modifications.

The serum half-life of proteins comprising Fc regions may be increased by increasing the binding affinity of the Fc region for FcRn. In one embodiment, the Fc variant protein has enhanced serum half-life relative to comparable molecule.

In another embodiment, the present invention provides an Fc variant, wherein the Fc region comprises at least one non naturally occurring amino acid at one or more positions selected from the group consisting of 239, 330 and 332, as numbered by the EU index as set forth in Kabat. In a specific embodiment, the present invention provides an Fc variant, wherein the Fc region comprises at least one non naturally occurring amino acid selected from the group consisting of 239D, 330L and 332E, as numbered by the EU index as set forth in Kabat. Optionally, the Fc region may further comprise additional non-naturally occurring amino acid at one or more positions selected from the group consisting of 252, 254, and 256, as numbered by the EU index as set forth in Kabat. In a specific embodiment, the present invention provides an Fc variant, wherein the Fc region comprises at least one non naturally occurring amino acid selected from the group consisting of 239D, 330L and 332E, as numbered by the EU index as set forth in Kabat and at least one non naturally occurring amino acid at one or more positions selected from the group consisting of 252Y, 254T and 256E, as numbered by the EU index as set forth in Kabat.

In another embodiment, the present invention provides an Fc variant, wherein the Fc region comprises at least one non naturally occurring amino acid at one or more positions is selected from the group consisting of 234, 235 and 331, as numbered by the EU index as set forth in Kabat. In a specific embodiment, the present invention provides an Fc variant, wherein the Fc region comprises at least one non naturally occurring amino acid selected from the group consisting of 234F, 235F, 235Y, and 331S, as numbered by the EU index as set forth in Kabat. In a further specific embodiment, an Fc variant of the invention comprises the 234F, 235F, and 331S non-naturally occurring amino acid residues, as numbered by the EU index as set forth in Kabat. In another specific embodiment, an Fc variant of the invention comprises the 234F, 235Y, and 331S non-naturally occurring amino acid residues, as numbered by the EU index as set forth in Kabat. Optionally, the Fc region may further comprise additional non-naturally occurring amino acid at one or more positions selected from the group consisting of 252, 254, and 256, as numbered by the EU index as set forth in Kabat. In a specific embodiment, the present invention provides an Fc variant, wherein the Fc region comprises at least one non naturally occurring amino acid selected from the group consisting of 234F, 235F, 235Y, and 331S, as numbered by the EU index as set forth in Kabat; and at least one non naturally occurring amino acid at one or more positions are selected from the group consisting of 252Y, 254T and 256E, as numbered by the EU index as set forth in Kabat.

In another embodiment, the present invention provides an Fc variant protein formulation, wherein the Fc region comprises at least a non naturally occurring amino acid at one or more positions selected from the group consisting of 239, 330 and 332, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat. Optionally, the Fc region may further comprise additional non-naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat and at least one non naturally occurring amino acid at one or more positions are selected from the group consisting of 252Y, 254T and 256E, as numbered by the EU index as set forth in Kabat.

In another embodiment, the present invention provides an Fc variant protein formulation, wherein the Fc region comprises at least one non naturally occurring amino acid at one or more positions selected from the group consisting of 234, 235 and 331, as numbered by the EU index as set forth in Kabat. In a specific embodiment, the present invention provides an Fc variant protein formulation, wherein the Fc region comprises at least one non naturally occurring amino acid selected from the group consisting of 234F, 235F, 235Y, and 331S, as numbered by the EU index as set forth in Kabat. Optionally, the Fc region may further comprise additional non-naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 234F, 235F, 235Y, and 331S, as numbered by the EU index as set forth in Kabat; and at least one non naturally occurring amino acid at one or more positions are selected from the group consisting of 252Y, 254T and 256E, as numbered by the EU index as set forth in Kabat.

Methods for generating non naturally occurring Fc regions are known in the art. For example, amino acid substitutions and/or deletions can be generated by mutagenesis methods, including, but not limited to, site-directed mutagenesis (Kunkel, *Proc. Natl. Acad. Sci.* USA 82:488-492 (1985)), PCR mutagenesis (Higuchi, in "PCR Protocols: a Guide to Methods and Applications", Academic Press, San Diego, pp. 177-183 (1990)), and cassette mutagenesis (Wells et al, Gene 46:315-323 (1985)). Preferably, site-directed mutagenesis is performed by the overlap-extension PCR method (Higuchi, in "PCR Technology: Principles and Applications for DNA Amplification", Stockton Press, New York, pp. 61-70 (1989)). The technique of overlap-extension PCR (Higuchi, ibid.) can also be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the is resulting restriction fragment is cloned into an appropriate vector. As the first step of mutagenesis, the starting DNA (e.g., encoding an Fc fusion protein, an antibody or simply an Fc region) is operably cloned into a mutagenesis vector. The primers are designed to reflect the desired amino acid substitution. Other methods useful for the generation of variant Fc regions are known in the art (see, e.g., U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO

99/58572; WO 00/42072; WO 02/060919; WO 04/029207; WO 04/099249; WO 04/063351).

In some embodiments of the invention, the glycosylation patterns of the antibodies provided herein are modified to enhance ADCC and CDC effector function. See Shields R L et al, (2002) JBC. 277:26733; Shinkawa T et al, (2003) JBC. 278:4666 and Okazaki A et al, (2004) J. Mol. Biol., 336: 1239. In some embodiments, an Fc variant protein comprises one or more engineered glycoforms, i.e., a carbohydrate composition that is covalently attached to the molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al, 20017 Biotechnol Bioeng 74:288-294; Shields et al, 2002, J Biol Chem 277:26733-26740; Shinkawa et al, 2003, J Biol Chem 278:4666-4673) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al, 2004, JMB, 336: 1239-49.

It is also known in the art that the glycosylation of the Fc region can be modified to increase or decrease effector function (see for examples, Umana et al, 1999, Nat. Biotechnol 17:176-180; Davies et al, 2001, Biotechnol Bioeng 74:288-294; Shields et al, 2002, J Biol Chem 277:26733-26740; Shinkawa et al, 2003 J Biol Chem 278:4666-4673) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). Accordingly, in one embodiment the Fc regions of the antibodies of the invention comprise altered glycosylation of amino acid residues. In another embodiment, the altered glycosylation of the amino acid residues results in lowered effector function. In another embodiment, the altered glycosylation of the amino acid residues results in increased effector function. In a specific embodiment, the Fc region has reduced fucosylation. In another embodiment, the Fc region is afucosylated (see for examples, U.S. Patent Application Publication No. 2005/0226867).

DETAILED DESCRIPTION OF THE PREFERRED EMBODIMENT

Figure 1:
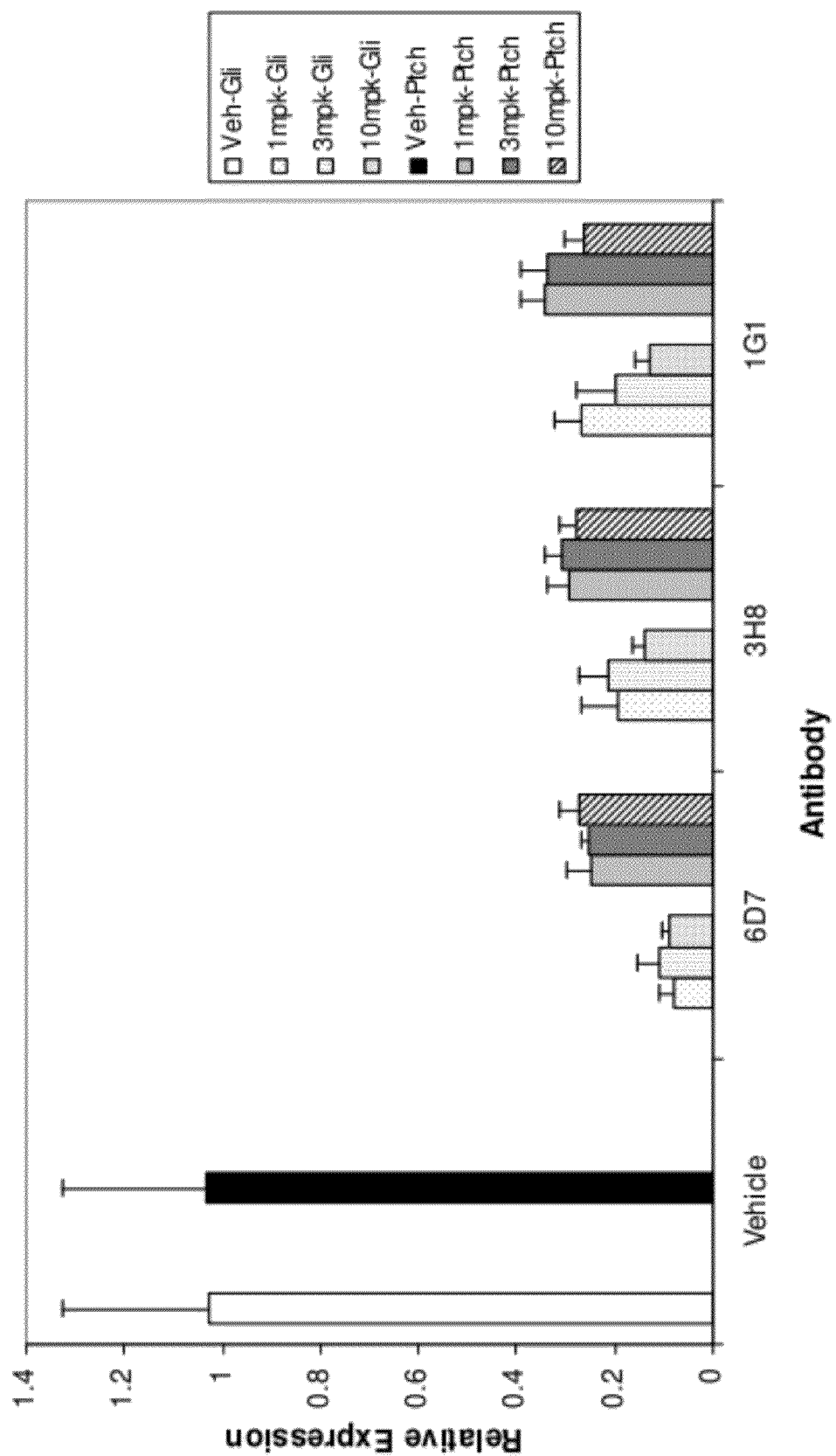
FIG. 1 depicts a bar chart showing the results from pharmacodynamic modulation of mouse Gli1 and Ptc1 in the stroma of Colo205 Xenograft tumors by particular antibodies.

Embodiments of the invention relate to a novel set of Shh blocking molecules, such as, for example, antibodies, that inhibits binding of Shh to Patched 1/2. Such molecules can be used as single agents, or alternatively, in combination with other binding antibodies/agents. They can also be used in combination with any standard or novel anti-cancer agents.

Embodiments of the invention relate to targeted binding agents that bind to Shh. In some embodiments, the targeted binding agents bind to Shh and inhibit the binding of a Shh to its receptor Patched-½. In some embodiments, this binding can neutralize, block, inhibit, abrogate, or interfere with one or more aspects of Shh-associated effects. In one embodiment, the targeted binding agents are monoclonal antibodies, or binding fragments thereof. Such monoclonal antibodies may be referred to as anti-Shh antibodies herein.

Other embodiments of the invention include fully human anti-Shh antibodies, and antibody preparations that are therapeutically useful. In one embodiment, preparations of the anti-Shh antibody of the invention have desirable therapeutic properties, including strong binding affinity for Shh, the ability to promote endothelial cell apoptosis or inhibit proliferation of endothelial cells and the ability to induce endothelial cell cytotoxicity via ADCC and/or CDC activity.

In addition, embodiments of the invention include methods of using these antibodies for treating diseases. Anti-Shh antibodies of the invention are useful for preventing Shh-mediated tumor cell proliferation. Any disease that is characterized by any type of malignant tumour, including metastatic cancers, lymphatic tumours, and blood cancers, can also be treated by this inhibition mechanism. Exemplary cancers in humans include a bladder tumour, renal cell cancer, breast tumour, prostate tumour, basal cell carcinoma, biliary tract cancer, bladder cancer, bone cancer, brain and CNS cancer (e.g., glioma tumour), cervical cancer, choriocarcinoma, colon and rectum cancer, connective tissue cancer, cancer of the digestive system; endometrial cancer, esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma including multiple myeloma, neuroblastoma, oral cavity cancer (e.g., lip, tongue, mouth, and pharynx); ovarian cancer; pancreatic cancer, retinoblastoma; rhabdomyosarcoma; rectal cancer, renal cancer, cancer of the respiratory system; sarcoma, skin cancer; stomach cancer, testicular cancer, thyroid cancer; uterine cancer, cancer of the urinary system, as well as other carcinomas and sarcomas. Malignant disorders commonly diagnosed in dogs, cats, and other pets include, but are not limited to, lymphosarcoma, osteosarcoma, mammary tumours, mastocytoma, brain tumour, melanoma, adenosquamous carcinoma, carcinoid lung tumour, bronchial gland tumour, bronchiolar adenocarcinoma, fibroma, myxochondroma, pulmonary sarcoma, neurosarcoma, osteoma, papilloma, retinoblastoma, Ewing's sarcoma, Wilm's tumour, Burkitt's lymphoma, microglioma, neuroblastoma, osteoclastoma, oral neoplasia, fibrosarcoma, osteosarcoma and rhabdomyosarcoma, genital squamous cell carcinoma, transmissible venereal tumour, testicular tumour, seminoma, Sertoli cell tumour, hemangiopericytoma, histiocytoma, chloroma (e.g., granulocytic sarcoma), corneal papilloma, corneal squamous cell carcinoma, hemangiosarcoma, pleural mesothelioma, basal cell tumour, thymoma, stomach tumour, adrenal gland carcinoma, oral papillomatosis, hemangioendothelioma and cystadenoma, follicular lymphoma, intestinal lymphosarcoma, fibrosarcoma and pulmonary squamous cell carcinoma. In rodents, such as a ferret, exemplary cancers include insulinoma, lymphoma, sarcoma, neuroma, pancreatic islet cell tumour, gastric MALT lymphoma and gastric adenocarcinoma. Neoplasias affecting agricultural livestock include leukemia, hemangiopericytoma and bovine ocular neoplasia (in cattle); preputial fibrosarcoma, ulcerative squamous cell carcinoma, preputial carcinoma, connective tissue neoplasia and mastocytoma (in horses); hepatocellular carcinoma (in swine); lymphoma and pulmonary adenomatosis (in sheep); pulmonary sarcoma, lymphoma, Rous sarcoma, reticulo-endotheliosis, fibrosarcoma, nephroblastoma, B-cell lymphoma and lymphoid leukosis (in avian species); retinoblastoma, hepatic neoplasia, lymphosarcoma (lymphoblastic lymphoma), plasmacytoid leukemia and swimbladder sarcoma (in fish), caseous lymphadenitis (CLA): chronic, infectious, contagious disease of sheep and goats caused by the bacterium *Corynebacterium* pseudotuberculosis, and contagious lung tumour of sheep caused by jaagsiekte.

Other embodiments of the invention include diagnostic assays for specifically determining the quantity of Shh in a biological sample. The assay kit can include a targeted binding agent or antibody as disclosed herein along with the necessary labels for detecting such antibodies. These diagnostic assays are useful to screen for cell proliferation-related diseases including, but not limited to, neoplastic diseases.

Another aspect of the invention is an antagonist of the biological activity of Shh wherein the antagonist binds to Shh. In one embodiment, the antagonist is a targeted binding agent, such as an antibody. The antagonist may be selected from an antibody described herein, for example, antibody 1A12, 1G12, 1H10, 3H8, 4B6, 1G1, 1F4, 1H8, 1H12, 1C8, 1A5, 6D7, 6D7OP, 6D7OP2, 3H8OP, or 1G1OP.

In one embodiment the antagonist of the biological activity of Shh may bind to Shh and thereby inhibit or suppress ligand binding to the Hedgehog receptor, Patched-1, thereby inhibiting cell proliferation.

One embodiment is a targeted binding agent which binds to the same epitope or epitopes as fully human monoclonal antibody 1A12, 1G12, 1H10, 3H8, 4B6, 1G1, 1F4, 1H8, 1H12, 1C8, 1A5, 6D7, 6D7OP, 6D7OP2, 3H8OP, or 1G1OP.

One embodiment is an antibody which binds to the same epitope or epitopes as fully human monoclonal antibody 1A12, 1G12, 1H10, 3H8, 4B6, 1G1, 1F4, 1H8, 1H12, 1C8, 1A5, 6D7, 6D7OP, 6D7OP2, 3H8OP, or 1G1OP.

One embodiment is a hybridoma that produces the targeted binding agent as described hereinabove. In one embodiment is a hybridoma that produces the light chain and/or the heavy chain of the antibodies as described hereinabove. In one embodiment the hybridoma produces the light chain and/or the heavy chain of a fully human monoclonal antibody. In another embodiment the hybridoma produces the light chain and/or the heavy chain of fully human monoclonal antibody 1A12, 1G12, 1H10, 3H8, 4B6, 1G1, 1F4, 1H8, 1H12, 1C8, 1A5, 6D7, 6D7OP, 6D7OP2, 3H8OP, or 1G1OP. Alternatively the hybridoma may produce an antibody which binds to the same epitope or epitopes as fully human monoclonal antibody 1A12, 1G12, 1H10, 3H8, 4B6, 1G1, 1F4, 1H8, 1H12, 1C8, 1A5, 6D7, 6D7OP, 6D7OP2, 3H8OP, or 1G1OP.

Another embodiment is a nucleic acid molecule encoding the targeted binding agent as described hereinabove. In one embodiment is a nucleic acid molecule encoding the light chain or the heavy chain of an antibody as described hereinabove. In one embodiment the nucleic acid molecule encodes the light chain or the heavy chain of a fully human monoclonal antibody. Still another embodiment is a nucleic acid molecule encoding the light chain or the heavy chain of a fully human monoclonal antibody selected from antibodies 1A12, 1G12, 1H10, 3H8, 4B6, 1G1, 1F4, 1H8, 1H12, 1C8, 1A5, 6D7, 6D7OP, 6D7OP2, 3H8OP, or 1G1OP.

Another embodiment of the invention is a vector comprising a nucleic acid molecule or molecules as described hereinabove, wherein the vector encodes a targeted binding agent as defined hereinabove. In one embodiment of the invention is a vector comprising a nucleic acid molecule or molecules as described hereinabove, wherein the vector encodes a light chain and/or a heavy chain of an antibody as defined hereinabove.

Yet another embodiment of the invention is a host cell comprising a vector as described hereinabove. Alternatively the host cell may comprise more than one vector.

In addition, one embodiment of the invention is a method of producing a targeted binding agent of the invention by culturing host cells under conditions wherein a nucleic acid molecule is expressed to produce the targeted binding agent, followed by recovery of the targeted binding agent. In one embodiment of the invention is a method of producing an antibody of the invention by culturing host cells under conditions wherein a nucleic acid molecule is expressed to produce the antibody, followed by recovery of the antibody.

In one embodiment the invention includes a method of making an targeted binding agent by transfecting at least one host cell with at least one nucleic acid molecule encoding the targeted binding agent as described hereinabove, expressing the nucleic acid molecule in the host cell and isolating the targeted binding agent. In one embodiment the invention includes a method of making an antibody by transfecting at least one host cell with at least one nucleic acid molecule encoding the antibody as described hereinabove, expressing the nucleic acid molecule in the host cell and isolating the antibody.

According to another aspect, the invention includes a method of antagonising the biological activity of Shh by administering an antagonist as described herein. The method may include selecting an animal in need of treatment for cell proliferation, and administering to the animal a therapeutically effective dose of an antagonist of the biological activity of Shh.

Another aspect of the invention includes a method of antagonising the biological activity of Shh by administering a targeted binding agent as described hereinabove. The method may include selecting an animal in need of treatment for cell proliferation, and administering to the animal a therapeutically effective dose of a targeted binding agent that antagonises the biological activity of Shh.

Another aspect of the invention includes a method of antagonising the biological activity of Shh by administering an antibody as described hereinabove. The method may include selecting an animal in need of treatment of cell proliferation, and administering to the animal a therapeutically effective dose of an antibody which antagonises the biological activity of Shh.

According to another aspect there is provided a method of treating cell proliferation in an animal by administering a therapeutically effective amount of an antagonist of the biological activity of Shh. The method may include selecting an animal in need of treatment for cell proliferation, and administering to the animal a therapeutically effective dose of an antagonist of the biological activity of Shh.

According to another aspect there is provided a method of treating cell proliferation in an animal by administering a therapeutically effective amount of a targeted binding agent which antagonizes the biological activity of Shh. The method may include selecting an animal in need of treatment for cell proliferation, and administering to the animal a therapeutically effective dose of a targeted binding agent which antagonises the biological activity of Shh. The targeted binding agent can be administered alone, or can be administered in combination with additional antibodies or chemotherapeutic drugs or radiation therapy.

According to another aspect there is provided a method of treating cell proliferation in an animal by administering a therapeutically effective amount of an antibody which antagonizes the biological activity of Shh. The method may include selecting an animal in need of treatment for cell proliferation, and administering to the animal a therapeutically effective dose of an antibody which antagonises the biological activity of Shh. The antibody can be administered alone, or can be administered in combination with additional antibodies or chemotherapeutic drugs or radiation therapy.

According to another aspect there is provided a method of treating cancer in an animal by administering a therapeutically effective amount of an antagonist of the biological activity of Shh. The method may include selecting an animal in need of treatment for cancer, and administering to the animal a therapeutically effective dose of an antagonist which antagonises the biological activity of Shh. The antagonist can be administered alone, or can be administered in combination with additional antibodies or chemotherapeutic drugs or radiation therapy.

According to another aspect there is provided a method of treating cancer in an animal by is administering a therapeutically effective amount of a targeted binding agent which antagonizes the biological activity of Shh. The method may include selecting an animal in need of treatment for cancer, and administering to the animal a therapeutically effective dose of a targeted binding agent which antagonises the biological activity of Shh. The targeted binding agent can be administered alone, or can be administered in combination with additional antibodies or chemotherapeutic drugs or radiation therapy.

According to another aspect there is provided a method of treating cancer in an animal by administering a therapeutically effective amount of an antibody which antagonizes the biological activity of Shh. The method may include selecting an animal in need of treatment for cancer, and administering to the animal a therapeutically effective dose of an antibody which antagonises the biological activity of Shh. The antibody can be administered alone, or can be administered in combination with additional antibodies or chemotherapeutic drugs or radiation therapy.

According to another aspect there is provided a method of reducing or inhibiting tumour cell proliferation in an animal by administering a therapeutically effective amount of an antibody which antagonizes the biological activity of Shh. The method may include selecting an animal in need of a reduction or inhibition of proliferation and administering to the animal a therapeutically effective dose of an antibody which antagonises the biological activity of Shh. The antibody can be administered alone, or can be administered in combination with additional antibodies or chemotherapeutic drugs or radiation therapy.

According to another aspect there is provided a method of reducing tumour growth and/or metastasis, in an animal by administering a therapeutically effective amount of an antibody which antagonizes the biological activity of Shh. The method may include selecting an animal in need of a reduction of tumour growth and/or metastasis, and administering to the animal a therapeutically effective dose of an antibody which antagonises the biological activity of Shh. The antibody can be administered alone, or can be administered in combination with additional antibodies or chemotherapeutic drugs or radiation therapy.

According to another aspect of the invention there is provided the use of an antagonist of the biological activity of Shh for the manufacture of a medicament for the treatment of cell proliferation. In one embodiment the antagonist of the biological activity of Shh is a targeted binding agent of the invention. In one embodiment the antagonist of the biological activity of Shh is an antibody of the invention.

According to another aspect of the invention there is provided an antagonist of the biological activity of Shh for use as a medicament for the treatment of cell proliferation. In one embodiment the antagonist of the biological activity of Shh is a targeted binding agent of the invention. In one embodiment the antagonist of the biological activity of Shh is an antibody of the invention.

According to another aspect of the invention there is provided the use of a targeted binding agent or an antibody which antagonizes the biological activity of Shh for the manufacture of a medicament for the treatment of cell proliferation.

According to another aspect of the invention there is provided a targeted binding agent or an antibody which antagonizes the biological activity of Shh for use as a medicament for the treatment of cell proliferation.

According to another aspect of the invention there is provided the use of a targeted binding agent or an antibody which antagonizes the biological activity of Shh for the manufacture of a medicament for the treatment of disease-related cell proliferation.

According to another aspect of the invention there is provided an antibody which antagonizes the biological activity of Shh for use as a medicament for the treatment of disease-related cell proliferation.

According to another aspect of the invention there is provided the use of an antagonist of the biological activity of Shh for the manufacture of a medicament for the treatment of cancer in a mammal. In one embodiment the antagonist of the biological activity of Shh is a targeted binding agent of the invention. In one embodiment the antagonist of the biological activity of Shh is an antibody of the invention.

According to another aspect of the invention there is provided an antagonist of the biological activity of Shh for use as a medicament for the treatment of cancer in a mammal. In one embodiment the antagonist of the biological activity of Shh is a targeted binding agent of the invention. In one embodiment the antagonist of the biological activity of Shh is an antibody of the invention.

According to another aspect of the invention there is provided the use of a targeted binding agent which antagonizes the biological activity of Shh for the manufacture of a medicament for the treatment of cancer in a mammal.

According to another aspect of the invention there is provided a targeted binding agent is which antagonizes the biological activity of Shh for use as a medicament for the treatment of cancer in a mammal.

According to another aspect of the invention there is provided the use of an antibody which antagonizes the biological activity of Shh for the manufacture of a medicament for the treatment of cancer in a mammal.

According to another aspect of the invention there is provided an antibody which antagonizes the biological activity of Shh for use as a medicament for the treatment of cancer in a mammal.

According to another aspect there is provided the use of a targeted binding agent or an antibody which antagonizes the biological activity of Shh for the manufacture of a medicament for the reduction or inhibition proliferation in an animal.

According to another aspect there is provided a targeted binding agent or an antibody which antagonizes the biological activity of Shh for use as a medicament for the reduction or inhibition proliferation, and/or angiogenesis in an animal.

According to another aspect there is provided the use of a targeted binding agent or an antibody which antagonizes the biological activity of Shh for the manufacture of a medicament for reducing tumour growth and/or metastasis, in an animal.

According to another aspect there is provided a targeted binding agent or an antibody which antagonizes the biological activity of Shh for use as a medicament for reducing tumour growth and/or metastasis, in an animal.

In one embodiment the present invention is particularly suitable for use in antagonizing Shh, in patients with a tumour which is dependent alone, or in part, on Shh receptor signalling.

According to another aspect of the invention there is provided a pharmaceutical composition comprising an antagonist of the biological activity of Shh, and a pharmaceutically acceptable carrier. In one embodiment the antagonist comprises an antibody. According to another aspect of the invention there is provided a pharmaceutical composition comprising an antagonist of the biological activity of Shh, and a pharmaceutically acceptable carrier. In one embodiment the antagonist comprises an antibody.

In some embodiments, following administration of the antibody that specifically binds to Shh, a clearing agent is administered, to remove excess circulating antibody from the blood.

Anti-Shh antibodies are useful in the detection of Shh in patient samples and accordingly are useful as diagnostics for disease states as described herein. In addition, based on their ability to significantly inhibit Shh-mediated signaling activity (as demonstrated in the Examples below), anti-Shh antibodies have therapeutic effects in treating symptoms and conditions resulting from Shh expression. In specific embodiments, the antibodies and methods herein relate to the treatment of symptoms resulting from Shh-induced proliferation and/or intracellular signaling. Further embodiments involve using the antibodies and methods described herein to treat cell proliferation-related diseases including neoplastic diseases, such as, melanoma, small cell lung cancer, non-small cell lung cancer, glioma, hepatocellular (liver) carcinoma, thyroid tumour, gastric (stomach) cancer, prostate cancer, breast cancer, ovarian cancer, bladder cancer, lung cancer, glioblastoma, endometrial cancer, kidney cancer, colon cancer, and pancreatic cancer.

Another embodiment of the invention includes an assay kit for detecting Shh in mammalian tissues, cells, or body fluids to screen for cell proliferation related diseases. The kit includes a targeted binding agent that binds to Shh and a means for indicating the reaction of the targeted binding agent with Shh, if present. In one embodiment, the targeted binding agent that binds Shh is labeled. In another embodiment the targeted binding agent is an unlabeled and the kit further includes a means for detecting the targeted binding agent. Preferably the targeted binding agent is labeled with a marker selected from the group consisting of a fluorochrome, an enzyme, a radionuclide and a radio-opaque material.

Another embodiment of the invention includes an assay kit for detecting Shh in mammalian tissues, cells, or body fluids to screen for proliferation-related diseases. The kit includes an antibody that binds to Shh and a means for indicating the reaction of the antibody with Shh, if present. The antibody may be a monoclonal antibody. In one embodiment, the antibody that binds Shh is labeled. In another embodiment the antibody is an unlabeled primary antibody and the kit further includes a means for detecting the primary antibody. In one embodiment, the means includes a labeled second antibody that is an anti-immunoglobulin. Preferably the antibody is labeled with a marker selected from the group consisting of a fluorochrome, an enzyme, a radionuclide and a radio-opaque material.

Further embodiments, features, and the like regarding the antibodies as disclosed herein are provided in additional detail below.

Sequence Listing

Embodiments of the invention include the specific antibodies listed below in Table 1. This table reports the identification number of each anti-Shh antibody, along with the SEQ ID number of the variable domain of the corresponding heavy chain and light chain genes and polypeptides, respectively. Each antibody has been given an identification number.

TABLE 1

| Mab ID No.: | Sequence | SEQ ID NO: |
|---|---|---|
| 1A12 | Nucleotide sequence encoding the variable region of the heavy chain | 1 |
| | Amino acid sequence encoding the variable region of the heavy chain | 2 |
| | Nucleotide sequence encoding the variable region of the light chain | 3 |
| | Amino acid sequence encoding the variable region of the light chain | 4 |
| 1G12 | Nucleotide sequence encoding the variable region of the heavy chain | 5 |
| | Amino acid sequence encoding the variable region of the heavy chain | 6 |
| | Nucleotide sequence encoding the variable region of the light chain | 7 |
| | Amino acid sequence encoding the variable region of the light chain | 8 |
| 1H10 | Nucleotide sequence encoding the variable region of the heavy chain | 9 |
| | Amino acid sequence encoding the variable region of the heavy chain | 10 |

TABLE 1-continued

| Mab ID No.: | Sequence | SEQ ID NO: |
|---|---|---|
| | Nucleotide sequence encoding the variable region of the light chain | 11 |
| | Amino acid sequence encoding the variable region of the light chain | 12 |
| 3H8 | Nucleotide sequence encoding the variable region of the heavy chain | 13 |
| | Amino acid sequence encoding the variable region of the heavy chain | 14 |
| | Nucleotide sequence encoding the variable region of the light chain | 15 |
| | Amino acid sequence encoding the variable region of the light chain | 16 |
| 4B6 | Nucleotide sequence encoding the variable region of the heavy chain | 17 |
| | Amino acid sequence encoding the variable region of the heavy chain | 18 |
| | Nucleotide sequence encoding the variable region of the light chain | 19 |
| | Amino acid sequence encoding the variable region of the light chain | 20 |
| 1G1 | Nucleotide sequence encoding the variable region of the heavy chain | 21 |
| | Amino acid sequence encoding the variable region of the heavy chain | 22 |
| | Nucleotide sequence encoding the variable region of the light chain | 23 |
| | Amino acid sequence encoding the variable region of the light chain | 24 |
| 1F4 | Nucleotide sequence encoding the variable region of the heavy chain | 25 |
| | Amino acid sequence encoding the variable region of the heavy chain | 26 |
| | Nucleotide sequence encoding the variable region of the light chain | 27 |
| | Amino acid sequence encoding the variable region of the light chain | 28 |
| 1H8 | Nucleotide sequence encoding the variable region of the heavy chain | 29 |
| | Amino acid sequence encoding the variable region of the heavy chain | 30 |
| | Nucleotide sequence encoding the variable region of the light chain | 31 |
| | Amino acid sequence encoding the variable region of the light chain | 32 |
| 1H12 | Nucleotide sequence encoding the variable region of the heavy chain | 33 |
| | Amino acid sequence encoding the variable region of the heavy chain | 34 |
| | Nucleotide sequence encoding the variable region of the light chain | 35 |
| | Amino acid sequence encoding the variable region of the light chain | 36 |
| 1C8 | Nucleotide sequence encoding the variable region of the heavy chain | 37 |
| | Amino acid sequence encoding the variable region of the heavy chain | 38 |
| | Nucleotide sequence encoding the variable region of the light chain | 39 |
| | Amino acid sequence encoding the variable region of the light chain | 40 |
| 1A5 | Nucleotide sequence encoding the variable region of the heavy chain | 41 |
| | Amino acid sequence encoding the variable region of the heavy chain | 42 |
| | Nucleotide sequence encoding the variable region of the light chain | 43 |
| | Amino acid sequence encoding the variable region of the light chain | 44 |
| 6D7 | Nucleotide sequence encoding the variable region of the heavy chain | 45 |
| | Amino acid sequence encoding the variable region of the heavy chain | 46 |
| | Nucleotide sequence encoding the variable region of the light chain | 47 |
| | Amino acid sequence encoding the variable region of the light chain | 48 |
| 6D7 OP(2) | Nucleotide sequence encoding the variable region of the heavy chain | 49 |
| | Amino acid sequence encoding the variable region of the heavy chain | 50 |
| | Nucleotide sequence encoding the variable region of the light chain | 51 |
| | Amino acid sequence encoding the variable region of the light chain | 52 |
| 6D7 OP | Nucleotide sequence encoding the variable region of the heavy chain | 49 |
| | Amino acid sequence encoding the variable region of the heavy chain | 50 |
| | Nucleotide sequence encoding the variable region of the light chain | 53 |
| | Amino acid sequence encoding the variable region of the light chain | 54 |
| 1G1OP | Nucleotide sequence encoding the variable region of the heavy chain | 21 |
| | Amino acid sequence encoding the variable region of the heavy chain | 22 |
| | Nucleotide sequence encoding the variable region of the light chain | 55 |
| | Amino acid sequence encoding the variable region of the light chain | 56 |
| 3H8 OP | Nucleotide sequence encoding the variable region of the heavy chain | 57 |
| | Amino acid sequence encoding the variable region of the heavy chain | 58 |
| | Nucleotide sequence encoding the variable region of the light chain | 59 |
| | Amino acid sequence encoding the variable region of the light chain | 60 |

DEFINITIONS

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

An antagonist or inhibitor may be a polypeptide, nucleic acid, carbohydrate, lipid, small molecular weight compound, an oligonucleotide, an oligopeptide, RNA interference (RNAi), antisense, a recombinant protein, an antibody, or fragments thereof or conjugates or fusion proteins thereof. For a review of RNAi see Milhavet O, Gary D S, Mattson M P. (Pharmacol Rev. 2003 December; 55(4):629-48. Review) and antisense (see Opalinska J B, Gewirtz A M. (Sci STKE. 2003 Oct. 28; 2003 (206):pe47.)

A compound refers to any small molecular weight compound with a molecular weight of less than about 2000 Daltons.

The term "sonic Hedgehog Homolog" or "Shh" refers to the molecule that is sonic Hedgehog homolog protein, also known as HHG1, HHG-1, HLP3, HPE3, SMMCI, TPT, TPTPS, MCOPCB5, and Sonic hedgehog protein precursor.

The terms "neutralizing" or "inhibits" when referring to a targeted binding agent, such as an antibody, relates to the ability of an antibody to eliminate, reduce, or significantly reduce, the activity of a target antigen. Accordingly, a "neutralizing" anti-Shh antibody of the invention is capable of eliminating or significantly reducing the activity of Shh. A neutralizing Shh antibody may, for example, act by blocking the binding of a Shh to its receptor Patched, e.g., Patched-1 or Patched-2. By blocking this binding, Shh signal-mediated activity is significantly, or completely, eliminated. Ideally, a neutralizing antibody against Shh inhibits tumor cell proliferation, or inhibits production by stromal cells of factors that promote tumor cell proliferation, or inhibits self-renewal of cancer stem cells.

An "antagonist of the biological activity of Shh" is capable of eliminating, reducing or significantly reducing the activity of Shh. An "antagonist of the biological activity of Shh" is capable of eliminating, reducing or significantly reducing Shh signaling. An "antagonist of the biological activity of Shh" may eliminate or significantly reduce tumor cell proliferation.

"Reducing Shh signaling" encompasses a reduction of Shh signaling by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% in comparison with the level of signaling in the absence of a targeted binding agent, antibody or antagonist of the invention.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

An "optimized" sequence is an antibody sequence where the CDR and/or framework sequence of the variable heavy or light chain sequence is mutated to remove one or more non-germline sequence sequences and can further include the removal of structural liabilities from the sequence such as glycosylation sites or unpaired cysteines.

The terms "native" or "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "polynucleotide" as referred to herein means a polymeric form of nucleotides of at least 10 bases in length, either ribonucleotides or deoxynucleotides or a modified form of either type of nucleotide, or RNA-DNA hetero-duplexes. The term includes single and double stranded forms of DNA.

The term "oligonucleotide" referred to herein includes naturally occurring, and modified nucleotides linked together by naturally occurring, and non-naturally occurring linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g, LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed, Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridise" referred to herein means to detectably and specifically bind. Polynucleotides, oligonucleotides and fragments thereof selectively hybridise to nucleic acid strands under hybridisation and wash conditions that minimise appreciable amounts of detectable binding to nonspecific nucleic acids. High stringency conditions can be used to achieve selective hybridisation conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

Stringent hybridization conditions include, but are not limited to, hybridization to filter-bound DNA in 6× sodium chloride/sodium citrate (SSC) (0.9 M NaCl, 90 mM NaCitrate, pH 7.0) at about 45° C. followed by one or more washes in 0.2×SSC, 0.1% SDS at about 50-65° C., highly stringent conditions such as hybridization to filter-bound DNA in 6×SSC at about 45° C. followed by one or more washes in 0.1×SSC, 0.2% SDS at about 60° C., or any other stringent hybridization conditions known to those skilled in the art (see, for example, Ausubel, F. M. et al, eds. 1989 Current Protocols in Molecular Biology, vol. 1, Green Publishing Associates, Inc. and John Wiley and Sons, Inc, NY at pages 6.3.1 to 6.3.6 and 2.10.3). Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of more than 5 (in standard deviation units) using the program ALIGN with the mutation data matrix and a gap penalty of 6 or greater. See Dayhoff, M. O, in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. It should be appreciated that there can be differing regions of homology within two orthologous sequences. For example, the functional sites of mouse and human orthologues may have a higher degree of homology than non-functional regions.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology-A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the antibodies described herein.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

In general, cysteine residues in proteins are either engaged in cysteine-cysteine disulfide bonds or sterically protected from the disulfide bond formation when they are a part of folded is protein region. Disulfide bond formation in proteins is a complex process, which is determined by the redox potential of the environment and specialized thiol-disulfide exchanging enzymes (Creighton, Methods Enzymol. 107, 305-329, 1984; Houee-Levin, Methods Enzymol. 353, 35-44, 2002). When a cysteine residue does not have a pair in protein structure and is not sterically protected by folding, it can form a disulfide bond with a free cysteine from solution in a process known as disulfide shuffling. In another process known as disulfide scrambling, free cysteines may also interfere with naturally occurring disulfide bonds (such as those present in antibody structures) and lead to low binding, low biological activity and/or low stability.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed, W. H. Freeman and Company, New York (1984)); *Introduction to Protein Structure* (C. Branden and J. Tooze, eds, Garland Publishing, New York, N.Y. (1991)); and Thornton et al. *Nature* 354:105 (1991), which are each incorporated herein by reference.

Additionally, such methods may be used to make amino acid substitutions or deletions of one or more variable region cysteine residues participating in an intrachain disulfide bond to generate antibody molecules lacking one or more intrachain disulfide bonds.

The term "CDR region" or "CDR" is intended to indicate the hypervariable regions of the heavy and light chains of an antibody which confer antigen-binding specificity to the antibody. CDRs may be defined according to the Kabat system (Kabat, E. A. et al. (1991) Sequences of Proteins of Immunological Interest, 5th Edition. US Department of Health and Human Services, Public Service, NIH, Washington), and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognises.

The third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody (Segal et al, PNAS, 71:4298-4302, 1974, Amit et al, Science, 233:747-753, 1986, Chothia et al, J. Mol. Biol, 196:901-917, 1987, Chothia et al, Nature, 462:877-883, 1989, Caton et al, J. Immunol, 144:1965-1968, 1990, Sharon et al, PNAS, 87:4814-4817, 1990, Sharon et al, J. Immunol, 144:4863-4869, 1990, Kabat et al, J. Immunol, 147:1709-1719, 1991).

The term a "set of CDRs" referred to herein comprises CDR1, CDR2 and CDR3. Thus, a set of HCDRs refers to HCDR1, HCDR2 and HCDR3, and a set of LCDRs refers to LCDR1, LCDR2 and LCDR3.

Variants of the VH and VL domains and CDRs of the present invention, including those for which amino acid sequences are set out herein, and which can be employed in targeting agents and antibodies for Shh can be obtained by means of methods of sequence alteration or mutation and screening for antigen targeting with desired characteristics. Examples of desired characteristics include but are not limited to: increased binding affinity for antigen relative to known antibodies which are specific for the antigen; increased neutralisation of an antigen activity relative to known antibodies which are specific for the antigen if the activity is known; specified competitive ability with a known antibody or ligand to the antigen at a specific molar ratio; ability to immunoprecipitate ligand-receptor complex; ability to bind to a specified epitope; linear epitope, e.g. peptide sequence identified using peptide-binding scan, e.g. using peptides screened in linear and/or constrained conformation; conformational epitope, formed by non-continuous residues; ability to modulate a new biological activity of Shh, or downstream molecule; ability to bind and/or neutralise Shh and/or for any other desired property.

The techniques required to make substitutions within amino acid sequences of CDRs, is antibody VH or VL domains and antigen binding sites are available in the art. Variants of antibody molecules disclosed herein may be produced and used in the present invention. Following the lead of computational chemistry in applying multivariate data analysis techniques to the structure/property-activity relationships (Wold, et al. Multivariate data analysis in chemistry. Chemometrics-Mathematics and Statistics in Chemistry (Ed.: B. Kowalski), D. Reidel Publishing Company, Dordrecht, Holland, 1984) quantitative activity-property relationships of antibodies can be derived using well-known mathematical techniques, such as statistical regression, pattern recognition and classification (Norman et al. Applied Regression Analysis. Wiley-Interscience; 3rd edition (April 1998); Kandel, Abraham & Backer, Eric. Computer-Assisted Reasoning in Cluster Analysis. Prentice Hall PTR, (May 11, 1995); Krzanowski, Wojtek. Principles of Multivariate Analysis: A User's Perspective (Oxford Statistical Science Series, No 22 (Paper)). Oxford University Press; (December 2000); Witten, Ian H. & Frank, Eibe. Data Mining: Practical Machine Learning Tools and Techniques with Java Implementations. Morgan Kaufmann; (Oct. 11, 1999); Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002); Ghose, Arup K. & Viswanadhan, Vellarkad N. Combinatorial Library Design and Evaluation Principles, Software, Tools, and Applications in Drug Discovery). In some cases the properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions.

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimisation experiments. In a structural approach, a model can be created of the antibody molecule using any freely available or commercial package, such as WAM. A protein visualisation and analysis software package, such as Insight II (Accelrys, Inc.) or Deep View may then be used to evaluate possible substitutions at each position in the CDR. This information may then be used to make substitutions likely to have a minimal or beneficial effect on activity or confer other desirable properties.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to Shh, under suitable binding conditions, (2) ability to block appropriate Shh/Patched-1 binding, or (3) ability to promote Gli activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics" (Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: $-CH_2NH-$, $-CH_2S-$, $-CH_2-CH_2-$, $-CH{=}CH-$ (cis and trans), $-COCH_2-$, $-CH(OH)CH_2-$, and $-CH_2SO-$, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Riand Gierasch *Ann. Rev. Biochem.* 61:387 (1992), incorporated herein by reference); for example, by adding internal cysteine residues capable of forming intramolecular disulfide bridges which cyclize the peptide.

An antibody may be oligoclonal, a polyclonal antibody, a monoclonal antibody, a chimeric antibody, a CDR-grafted antibody, a multi-specific antibody, a bispecific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species.

As used herein, the terms "antibody" and "antibodies" (immunoglobulins) encompass monoclonal antibodies (including full-length monoclonal antibodies), polyclonal antibodies, camelised antibodies and chimeric antibodies. As used herein, the term "antibody" or "antibodies" refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen chain. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK. The term "variable region" may also be used to describe the variable domain of a heavy chain or light chain. Particular amino acid residues are believed to form an interface between the light and heavy chain variable domains. The variable regions of each light/heavy chain pair form an antibody binding site. Such antibodies may be derived from any mammal, including, but not limited to, humans, monkeys, pigs, horses, rabbits, dogs, cats, mice, etc.

The term "antibody" or "antibodies" includes binding fragments of the antibodies of the invention, exemplary fragments include single-chain Fvs (scFv), single-chain antibodies, single domain antibodies, domain antibodies, Fv fragments, Fab fragments, F(ab') fragments, F(ab')2 fragments, antibody fragments that exhibit the desired biological activity, disulfide-stabilised variable region (dsFv), dimeric variable region (Diabody), anti-idiotypic (anti-Id) antibodies (including, e.g., anti-Id antibodies to antibodies of the invention), intrabodies, linear antibodies, single-chain antibody molecules and multispecific antibodies formed from antibody fragments and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

Digestion of antibodies with the enzyme, papain, results in two identical antigen-binding fragments, known also as "Fab" fragments, and a "Fc" fragment, having no antigen-binding activity but having the ability to crystallize Digestion of antibodies with the enzyme, pepsin, results in the a F(ab')$_2$ fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Fab" when used herein refers to a fragment of an antibody that comprises the constant domain of the light chain and the CH1 domain of the heavy chain.

"dAb" when used herein refers to a fragment of an antibody that is the smallest functional binding unit of a human antibodies. A "dAb" is a single domain antibody and comprises either the variable domain of an antibody heavy chain (VH domain) or the variable domain of an antibody light chain (VL domain). Each dAb contains three of the six naturally occurring CDRs (Ward et al, Binding activities of a repertoire of single immunoglobulin variable domains secreted from *Escherichia coli. Nature* 461, 544-546 (1989); Holt, et al, Domain antibodies: protein for therapy, *Trends Biotechnol.* 21, 484-49 (2003)). With molecular weights ranging from 11 to 15 kDa, they are four times smaller than a fragment antigen binding (Fab)2 and half the size of a single chain Fv (scFv) molecule.

"Camelid" when used herein refers to antibody molecules are composed of heavy-chain dimers which are devoid of light chains, but nevertheless have an extensive antigen-binding repertoire (Hamers-Casterman C, Atarhouch T, Muyldermans S, Robinson G, Hamers C, Songa E B, Bendahman N, Hamers R (1993) Naturally occurring antibodies devoid of light chains. Nature 363:446-448).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al, *Proc. Natl. Acad. Sci. USA,* 90:6444-6448 (1993).

It has been shown that fragments of a whole antibody can perform the function of binding antigens. Examples of binding fragments are (Ward, E. S. et al, (1989) Nature 461, 544-546) the Fab fragment consisting of VL, VII, CL and CH1 domains; (McCafferty et al (1990) Nature, 468, 552-554) the Fd fragment consisting of the VH and CH1 domains; (Holt et al (2003) Trends in Biotechnology 21, 484-490) the Fv fragment consisting of the VL and VH domains of a single antibody; (iv) the dAb fragment (Ward, E. S. et al, Nature 461, 544-546 (1989), McCafferty et al (1990) Nature, 468, 552-554, Holt et al (2003) Trends in Biotechnology 21, 484-490], which consists of a VH or a VL domain; (v) isolated CDR regions; (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, (1988) Science, 242, 423-426 Huston et al, (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger, P. (1993) et al, Proc. Natl. Acad. Sci. USA 90 6444-6448). Fv, scFv or diabody molecules may be stabilised by the incorporation of disulphide bridges linking the VH and VL domains (Reiter, Y. et al, Nature Biotech, 14, 1239-1245, 1996). Minibodies comprising a scFv joined to a CH3 domain may also be made (Hu, S. et al, (1996) Cancer Res, 56, 3055-3061). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see, Kabat et al, Sequences of Proteins of Immunological Interest, 5th Ed. Public Health Service, National is Institutes of Health, Bethesda, Md. (1991)). The constant domains are generally not involved directly in antigen binding, but may influence antigen binding affinity and may exhibit various effector functions, such as participation of the antibody in ADCC, CDC, and/or apoptosis.

The term "hypervariable region" when used herein refers to the amino acid residues of an antibody which are associated with its binding to antigen. The hypervariable regions encompass the amino acid residues of the "complementarity determining regions" or "CDRs" (e.g., residues 24-46 (L1), 50-56 (L2) and 89-97 (L3) of the light chain variable domain and residues 31-35 (H1), 50-65 (H2) and 95-102 (H3) of the heavy chain variable domain; Kabat et al, Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, J. Mol. Biol, 196:901-917 (1987)). "Framework" or "FR" residues are those variable domain residues flanking the CDRs. FR residues are present in chimeric, humanized, human, domain antibodies, diabodies, vaccibodies, linear antibodies, and bispecific antibodies.

As used herein, targeted binding agent, targeted binding protein, specific binding protein and like terms refer to an antibody, or binding fragment thereof that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope.

"Binding fragments" of an antibody are produced by recombinant DNA techniques, or by enzymatic or chemical cleavage of intact antibodies. Binding fragments include Fab, Fab', F(ab')$_2$, Fv, dAb and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is $\leq 1$ μM, preferably $\leq 100$ nM and most preferably $\leq 10$ nM.

The term "agent" is used herein to denote a chemical compound, a mixture of chemical compounds, a biological macromolecule, or an extract made from biological materials.

"Active" or "activity" in regard to an Shh polypeptide refers to a portion of an Shh polypeptide that has a biological or an immunological activity of a native Shh polypeptide.

"Biological" when used herein refers to a biological function that results from the activity of the native Shh polypeptide. A preferred Shh biological activity includes, for example, Shh induced cell proliferation.

"Mammal" when used herein refers to any animal that is considered a mammal. Preferably, the mammal is human.

"Animal" when used herein encompasses animals considered a mammal. Preferably the animal is human.

The term "mAb" refers to monoclonal antibody.

"Liposome" when used herein refers to a small vesicle that may be useful for delivery of drugs that may include the Shh polypeptide of the invention or antibodies to such an Shh polypeptide to a mammal.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^{3}H$, $^{14}C$, $^{15}N$, $^{35}S$, $^{90}Y$, $^{99}Tc$, $^{111}In$, $^{125}I$, $^{131}I$, fluorescent labels may include rhodamine, lanthanide phosphors or FITC and enzymatic labels may include horseradish peroxidase, β-galactosidase, luciferase, alkaline phosphatase.

Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes; additional fluorescent labels or fluorescers include, such as fluorescein and its derivatives, fluorochrome, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc. (Perkin Elmer and Cis Biointernational); chemoluminescent labels or chemiluminescers, such as isoluminol, luminol and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S, Ed, McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

"Antibody-dependent cell-mediated cytotoxicity" and "ADCC" refer to a cell-mediated reaction in which nonspecific cytotoxic cells that express Ig Fc receptors (FcRs) (e.g. Natural Killer (NK) cells, monocytes, neutrophils, and macrophages) recognise bound antibody on a target cell and subsequently cause lysis of the target cell. The primary cells for mediating ADCC, NK cells, express FcγRIII only, whereas monocytes express FcγRI, FcγRII and FcγRIII. FcRs expression on hematopoietic cells is summarised in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362, or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in an animal model such as that disclosed in Clynes et al. *PNAS* (USA) 95:652-656 (1988). "Complement dependent cytotoxicity" and "CDC" refer to the mechanism by which antibodies carry out their cell-killing function. It is initiated by the binding of C1q, a constituent of the first component of complement, to the Fc domain of Igs, IgG or IgM, which are in complex with antigen (Hughs-Jones, N. C, and B. Gardner. 1979. Mol. Immunol. 16:697). C1q is a large, structurally complex glycoprotein of ~410 kDa present in human serum at a concentration of 70 µg/ml (Cooper, N. R. 1985. Adv. Immunol. 37:151). Together with two serine proteases, C1r and C1s, C1q forms the complex C1, the first component of complement. At least two of the N-terminal globular heads of C1q must be bound to the Fc of Igs for C1 activation, hence for initiation of the complement cascade (Cooper, N. R. 1985. Adv. Immunol. 37:151).

The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body or a specific compartment thereof, for example, as measured in serum or plasma, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The term "isotype" refers to the classification of an antibody's heavy or light chain constant region. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. Several of these classes may be further divided into subclasses (isotypes), e.g., IgG1 (gamma 1), IgG2 (gamma 2), IgG3 (gamma 3), and IgG4 (gamma 4), and IgA1 and IgA2. The heavy chain constant regions that correspond to the different classes of immunoglobulins are called α, δ, ε, γ, and µ, respectively. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate in humans. Human light chain constant regions may be classified into two major classes, kappa and lambda.

If desired, the isotype of an antibody that specifically binds Shh can be switched, for example to take advantage of a biological property of a different isotype. For example, in some circumstances it can be desirable in connection with the generation of antibodies as therapeutic antibodies against Shh that the antibodies be capable of fixing complement and participating in complement-dependent cytotoxicity (CDC). There are a number of isotypes of antibodies that are capable of the same, including, without limitation, the following: murine IgM, murine IgG2a, murine IgG2b, murine IgG3, human IgM, human IgA, human IgG1, and human IgG3. In other embodiments it can be desirable in connection with the generation of antibodies as therapeutic antibodies against Shh that the antibodies be capable of binding Fc receptors on effector cells and participating in antibody-dependent cytotoxicity (ADCC). There are a number of isotypes of antibodies that are capable of the same, including, without limitation, the following: murine IgG2a, murine IgG2b, murine IgG3, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816,397), cell-cell fusion techniques (see e.g., U.S. Pat. Nos. 5,916,771 and 6,207,418), among others.

By way of example, the anti-Shh antibodies discussed herein are fully human antibodies. If an antibody possessed desired binding to Shh, it could be readily isotype switched to generate a human IgM, human IgG1, or human IgG3 isotype, while still possessing the same variable region (which defines the antibody's specificity and some of its affinity). Such molecule would then be capable of fixing complement and participating in CDC and/or be capable of binding to Fc receptors on effector cells and participating in ADCC.

"Whole blood assays" use unfractionated blood as a source of natural effectors. Blood is contains complement in the plasma, together with FcR-expressing cellular effectors, such as polymorphonuclear cells (PMNs) and mononuclear cells (MNCs). Thus, whole blood assays allow simultaneous evaluation of the synergy of both ADCC and CDC effector mechanisms in vitro.

A "therapeutically effective" amount as used herein is an amount that provides some improvement or benefit to the subject. Stated in another way, a "therapeutically effective" amount is an amount that provides some alleviation, mitigation, and/or decrease in at least one clinical symptom. Clinical symptoms associated with the disorders that can be treated by the methods of the invention are well-known to those skilled in the art. Further, those skilled in the art will appreciate that the therapeutic effects need not be complete or curative, as long as some benefit is provided to the subject.

The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually herein.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W, ed., 2nd ed. Raven Press, N.Y. (1989)) (incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called CDRs. The CDRs from the two chains of each pair are aligned by the framework regions, enabling binding to a specific epitope. From N-terminal to C-terminal, both light and heavy chains comprise the domains FR1 CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196: 901-917 (1987); Chothia et al. *Nature* 462:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g, Songsivilai & Lachmann *Clin. Exp. Immunol.* 79: 315-321 (1990), Kostelny et al. *J. Immunol.* 148:1547-1553 (1992). Bispecific antibodies do not exist in the form of fragments having a single binding site (e.g., Fab, Fab', and Fv).

Typically, a VH domain is paired with a VL domain to provide an antibody antigen-binding site, although a VH or VL domain alone may be used to bind antigen. The VH domain (see Table 12) may be paired with the VL domain (see Table 13), so that an antibody antigen-binding site is formed comprising both the VH and VL domains.

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

One method for generating fully human antibodies is through the use of XenoMouse® strains of mice that have been engineered to contain up to but less than 1000 kb-sized germline configured fragments of the human heavy chain locus and kappa light chain locus. See Mendez et al. *Nature Genetics* 15:146-156 (1997) and Green and Jakobovits *J. Exp. Med.* 188:483-495 (1998). The XenoMouse® strains are available from Amgen, Inc. (Fremont, Calif., U.S.A).

Such mice, then, are capable of producing human immunoglobulin molecules and antibodies and are deficient in the production of murine immunoglobulin molecules and antibodies. Technologies utilised for achieving the same are disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

The production of the XenoMouse® strains of mice is further discussed and delineated in U.S. patent application Ser. Nos. 07/466,008, filed Jan. 12, 1990, 07/610,515, filed Nov. 8, 1990, 07/919,297, filed Jul. 24, 1992, 07/922,649, filed Jul. 30, 1992, 08/031,801, filed Mar. 15, 1993, 08/112, 848, filed Aug. 27, 1993, 08/246,145, filed Apr. 28, 1994, 08/376,279, filed Jan. 20, 1995, 08/430, 938, filed Apr. 27, 1995, 08/464,584, filed Jun. 5, 1995, 08/464,582, filed Jun. 5, 1995, 08/463,191, filed Jun. 5, 1995, 08/462,837, filed Jun. 5, 1995, 08/486,853, filed Jun. 5, 1995, 08/486,857, filed Jun. 5, 1995, 08/486,859, filed Jun. 5, 1995, 08/462,513, filed Jun. 5, 1995, 08/724,752, filed Oct. 2, 1996, 08/759,620, filed Dec. 3, 1996, U.S. Publication 2003/0093820, filed Nov. 30, 2001 and U.S. Pat. Nos. 6,162,963, 6,150,584, 6,114,598, 6,075, 181, and 5,939,598 and Japanese Patent Nos. 3 068 180 B2, 3 068 506 B2, and 3 068 507 B2. See also European Patent No, EP 0 463 151 B1, grant published Jun. 12, 1996, International Patent Application No, WO 94/02602, published Feb. 3, 1994, International Patent Application No, WO 96/46096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc, have utilised a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023.010 to Krimpenfort and Berns, U.S. Pat. Nos. 5,612,205, 5,721,367, and 5,789, 215 to Berns et al, and U.S. Pat. No. 5,643,763 to Choi and Dunn, and GenPharm International U.S. patent application Ser. No. 07/574,748, filed Aug. 29, 1990, 07/575,962, filed Aug. 31, 1990, 07/810,279, filed Dec. 17, 1991, 07/853,408, filed Mar. 18, 1992, 07/904,068, filed Jun. 23, 1992, 07/990, 860, filed Dec. 16, 1992, 08/053,131, filed Apr. 26, 1993, 08/096,762, filed Jul. 22, 1993, 08/155,301, filed Nov. 18, 1993, 08/161,739, filed Dec. 3, 1993, 08/165,699, filed Dec. 10, 1993, 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al, 1992, Chen et al, 1993, Tuaillon et al, 1993, Choi et al, 1993, Lonberg et al, (1994), Taylor et al, (1994), and Tuaillon et al, (1995), Fishwild et al, (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM™-mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al, Cloning Stem Cells, (2002) 4:91-102).

Human antibodies can also be derived by in vitro methods. Suitable examples include but are not limited to phage display (Medimmune, Morphosys, Dyax, Biosite/Medarex, Xoma, Symphogen, Alexion (formerly Proliferon), Affimed) ribosome display (Medimmune), yeast display, and the like.

Preparation of Antibodies

Antibodies, as described herein, were prepared through the utilization of the XenoMouse® technology, as described below. Such mice are capable of producing human immunoglobulin molecules and antibodies and are deficient in the production of murine immunoglobulin molecules and antibodies. Technologies utilised for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

Through the use of such technology, fully human monoclonal antibodies to a variety of antigens have been produced. Essentially, XenoMouse® lines of mice are immunised with an antigen of interest (e.g. Shh), lymphatic cells (such as B cells) are recovered from the hyper-immunised mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to Shh. Further, provided herein are characterisation of the antibodies produced by such cell lines, including nucleotide and amino acid sequence analyses of the heavy and light chains of such antibodies.

Alternatively, instead of being fused to myeloma cells to generate hybridomas, B cells can be directly assayed. For example, CD19+ B cells can be isolated from hyperimmune XenoMouse® mice and allowed to proliferate and differentiate into antibody-secreting plasma cells. Antibodies from the cell supernatants are then screened by ELISA for reactivity against the Shh immunogen. The supernatants might also be screened for immunoreactivity against fragments of Shh to further map the different antibodies for binding to domains of functional interest on Shh. The antibodies may also be screened other related human endoglycosidases and against the rat, the mouse, and non-human primate, such as Cynomolgus monkey, orthologues of Shh, the last to determine species cross-reactivity. B cells from wells containing antibodies of interest may be immortalised by various methods including fusion to make hybridomas either from individual or from pooled wells, or by infection with EBV or transfection by known immortalising genes and then plating in suitable medium. Alternatively, single plasma cells secreting antibodies with the desired specificities are then isolated using an Shh-specific hemolytic plaque assay (see for example Babcook et al, *Proc. Natl. Acad. Sci. USA* 93:7843-48 (1996)). Cells targeted for lysis are preferably sheep red blood cells (SRBCs) coated with the Shh antigen.

In the presence of a B-cell culture containing plasma cells secreting the immunoglobulin of interest and complement, the formation of a plaque indicates specific Shh-mediated lysis of the sheep red blood cells surrounding the plasma cell of interest. The single antigen-specific plasma cell in the center of the plaque can be isolated and the genetic information that encodes the specificity of the antibody is isolated from the single plasma cell. Using reverse-transcription followed by PCR(RT-PCR), the DNA encoding the heavy and light chain variable regions of the antibody can be cloned. Such cloned DNA can then be further inserted into a suitable expression vector, preferably a vector cassette such as a pcDNA, more preferably such a pcDNA vector containing the constant domains of immunoglobulin heavy and light chain. The generated vector can then be transfected into host cells, e.g., HEK293 cells, CHO cells, and cultured in conventional nutrient media modified as appropriate for inducing transcription, selecting transformants, or amplifying the genes encoding the desired sequences.

As will be appreciated, antibodies that specifically bind Shh can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive Shh binding properties.

In the cell-cell fusion technique, a myeloma, CHO cell or other cell line is prepared that possesses a heavy chain with any desired isotype and another myeloma, CHO cell or other cell line is prepared that possesses the light chain. Such cells can, thereafter, be fused and a cell line expressing an intact antibody can be isolated.

Accordingly, as antibody candidates are generated that meet desired "structural" attributes as discussed above, they can generally be provided with at least certain of the desired "functional" attributes through isotype switching.

Therapeutic Administration and Formulations

Embodiments of the invention include sterile pharmaceutical formulations of anti-Shh antibodies that are useful as treatments for diseases. Such formulations would inhibit the binding of a native Shh binding to Patched-1, thereby effectively treating pathological conditions where, for example, serum or tissue Shh expression is abnormally elevated. Anti-Shh antibodies preferably possess adequate affinity to potently inhibit native Shh binding to Patched-1 and preferably have an adequate duration of action to allow for infrequent dosing in humans. A prolonged duration of action will allow for less frequent and more convenient dosing schedules by alternate parenteral routes such as subcutaneous or intramuscular injection.

Sterile formulations can be created, for example, by filtration through sterile filtration membranes, prior to or following lyophilization and reconstitution of the antibody. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, direct injection to a tumour site, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with pharmaceutically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional is pharmaceutical practice as described in Remington: The Science and Practice of Pharmacy (20$^{th}$ ed., Lippincott Williams & Wilkens Publishers (2003)). For example, dissolution or suspension of the active compound in a pharmaceutically acceptable carrier such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al, *J. Biomed Mater. Res*, (1981) 15:167-277 and Langer, *Chem. Tech*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al, *Biopolymers*, (1983) 22:547-556), non-degradable ethylene-vinyl acetate (Langer et al, supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitoneally can produce a sustained release effect. Other compositions also include liposomally entrapped antibodies. Liposomes containing is such antibodies are prepared by methods known per se: U.S. Pat. No. DE 3,218,121; Epstein et al, *Proc. Natl. Acad. Sci. USA*, (1985) 82:3688-3692; Hwang et al, *Proc. Natl. Acad. Sci. USA*, (1980) 77:4030-4046; EP 52,322; EP 36,676; EP 88,046; EP 143,949; 142,641; Japanese patent application 83-118008; U.S. Pat. Nos. 4,485,045 and 4,544, 545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.0001 mg/kg, 0.001 mg/kg, 0.01 mg/kg, 0.1 mg/kg, 1 mg/kg, 10 mg/kg to up to 100 mg/kg, 1000 mg/kg, 10000 mg/kg or more, of the patient's body weight depending on the factors mentioned above. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight depending on the factors mentioned above. Typically, the clinician will administer the therapeutic antibody until a dosage is reached that achieves the desired effect. The progress of this therapy is easily monitored by conventional assays or as described herein.

Doses of antibodies of the invention may be repeated and the administrations may be separated by at least 1 day, 2 days, 3 days, 5 days, 10 days, 15 days, 30 days, 45 days, 2 months, 75 days, 3 months, or at least 6 months.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2): 210-8 (2000), Wang W. "Lyophilization and development of solid protein pharmaceuticals." *Int. J. Pharm.* 203 (1-2):1-60 (2000), Charman W N "Lipids, lipophilic drugs, and oral drug delivery-some emerging concepts." *J Pharm Sci.* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Design and Generation of Other Therapeutics

In accordance with the present invention and based on the activity of the antibodies that are produced and characterized herein with respect to Shh, the design of other therapeutic modalities beyond antibody moieties is facilitated. Such modalities include, without limitation, advanced antibody therapeutics, such as bispecific antibodies, immunotoxins, and radiolabeled therapeutics, single domain antibodies, antibody fragments, such as a Fab, Fab', F(ab')$_2$, Fv or dAb, generation of peptide therapeutics, Shh binding domains in novel scaffolds, gene therapies, particularly intrabodies, antisense therapeutics, and small molecules.

An antigen binding site may be provided by means of arrangement of CDRs on non-antibody protein scaffolds, such as fibronectin or cytochrome B etc. (Haan & Maggos (2004) BioCentury, 12 (5): A1-A6; Koide et al. (1998) Journal of Molecular Biology, 284: 1141-1151; Nygren et al. (1997) Current Opinion in Structural Biology, 7: 463-469) or by randomising or mutating amino acid residues of a loop within a protein scaffold to confer binding specificity for a desired target. Scaffolds for engineering novel binding sites in proteins have been reviewed in detail by Nygren et al. (Nygren et al. (1997) Current Opinion in Structural Biology, 7: 463-469). Protein scaffolds for antibody mimics are disclosed in WO/0046784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 (Wess, L. In: BioCentury, The Bernstein Report on BioBusiness, 12 (42), A1-A7, 2004). Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, albumin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides-small proteins having intra-molecular disulphide bonds, Microproteins (Versabodies™, Amunix) and ankyrin repeat proteins (DARPins, Molecular Partners).

In addition to antibody sequences and/or an antigen-binding site, a targeted binding agent according to the present invention may comprise other amino acids, e.g. forming a peptide or polypeptide, such as a folded domain, or to impart to the molecule another functional characteristic in addition to ability to bind antigen. Targeted binding agents of the invention may carry a detectable label, or may be conjugated to a toxin or a targeting moiety or enzyme (e.g. via a peptidyl bond or linker). For example, a targeted binding agent may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

In connection with the generation of advanced antibody therapeutics, where complement fixation is a desirable attribute, it may be possible to sidestep the dependence on complement for cell killing through the use of bispecific antibodies, immunotoxins, or radiolabels, for example.

For example, bispecific antibodies can be generated that comprise (i) two antibodies one with a specificity to Shh and another to a second molecule that are conjugated together, (ii) a single antibody that has one chain specific to Shh and a second chain specific to a second molecule, or (iii) a single chain antibody that has specificity to Shh and the other molecule. Such bispecific antibodies can be generated using techniques that are well known; for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer (Suppl.)* 7:51-52 (1992). In each case, the second specificity can be made to the heavy chain activation receptors, including, without limitation, CD16 or CD64 (see e.g., Deo et al. *Immunol. Today* 18:127 (1997)) or CD89 (see e.g., Valerius et al. *Blood* 90:4485-4492 (1997)).

Antibodies can also be modified to act as immunotoxins, utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds, Lippincott Raven (1996)). See also U.S. Pat. Nos. 4,681,581, 4,735,210, 5,101,827, 5,102,990 (RE 35,500), 5,648,471, and 5,697,902. Each immunotoxin or radiolabeled molecule would be likely to kill cells expressing the desired multimeric enzyme subunit oligomerisation domain.

When an antibody is linked to an agent (e.g., radioisotope, pharmaceutical composition, or a toxin), it is contemplated that the agent possess a pharmaceutical property selected from the group of antimitotic, alkylating, antimetabolite, antiangiogenic, apoptotic, alkaloid, COX-2, and antibiotic agents and combinations thereof. The drug can be selected from the group of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antimetabolites, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, oxaliplatin, doxorubicins and their analogs, and a combination thereof.

Examples of toxins further include gelonin, *Pseudomonas* exotoxin (PE), PE40, PE38, diphtheria toxin, ricin, abrin, alpha toxin, saporin, ribonuclease (RNase), DNase I, Staphylococcal enterotoxin-A, pokeweed antiviral protein, gelonin, *Pseudomonas* endotoxin, members of the enediyne family of molecules, such as calicheamicin and esperamicin, as well as derivatives, combinations and modifications thereof. Chemical toxins can also be taken from the group consisting of duocarmycin (see, e.g., U.S. Pat. No. 5,703,080 and U.S. Pat. No. 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see, U.S. Pat. No. 4,675,187), Melphalan, and other related nitrogen mustards. Suitable toxins and chemotherapeutic agents are described in *Remington's Pharmaceutical Sciences*, 19th Ed. (Mack Publishing Co. 1995), and in Goodman And Gilman's The Pharmacological Basis of Therapeutics, 7th Ed. (MacMillan Publishing Co. 1985). Other suitable toxins and/or chemotherapeutic agents are known to those of skill in the art.

Examples of radioisotopes include gamma-emitters, positron-emitters, and x-ray emitters that can be used for localisation and/or therapy, and beta-emitters and alpha-emitters that can be used for therapy. The radioisotopes described previously as useful for diagnostics, prognostics and staging are also useful for therapeutics.

Non-limiting examples of anti-cancer or anti-leukemia agents include anthracyclines such as doxorubicin (adriamycin), daunorubicin (daunomycin), idarubicin, detorubicin, caminomycin, epirubicin, esorubicin, and morpholino and substituted derivatives, combinations and modifications thereof. Exemplary pharmaceutical agents include cis-platinum, taxol, calicheamicin, vincristine, cytarabine (Ara-C), cyclophosphamide, prednisone, daunorubicin, idarubicin, fludarabine, chlorambucil, interferon alpha, hydroxyurea, temozolomide, thalidomide, and bleomycin, and derivatives, combinations and modifications thereof. Preferably, the anti-cancer or anti-leukemia is doxorubicin, morpholinodoxorubicin, or morpholinodaunorubicin.

The antibodies of the invention also encompass antibodies that have half-lives (e.g., serum half-lives) in a mammal, preferably a human, of greater than that of an unmodified antibody. Said antibody half life may be greater than about 15 days, greater than about 20 days, greater than about 25 days, greater than about 30 days, greater than about 35 days, greater than about 40 days, greater than about 45 days, greater than about 2 months, greater than about 3 months, greater than about 4 months, or greater than about 5 months. The increased half-lives of the antibodies of the present invention or fragments thereof in a mammal, preferably a human, result in a higher serum titer of said antibodies or antibody fragments in the mammal, and thus, reduce the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., International Publication Nos. WO 97/46631 and WO 02/060919, which are incorporated herein by reference in their entireties). Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatisation that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

As will be appreciated by one of skill in the art, in the above embodiments, while affinity values can be important, other factors can be as important or more so, depending upon the particular function of the antibody. For example, for an immunotoxin (toxin associated with an antibody), the act of binding of the antibody to the target can be useful; however, in some embodiments, it is the internalisation of the toxin into the cell that is the desired end result. As such, antibodies with a high percent internalisation can be desirable in these situations. Thus, in one embodiment, antibodies with a high efficiency in internalisation are contemplated. A high efficiency of internalisation can be measured as a percent internalised antibody, and can be from a low value to 100%. For example, in varying embodiments, 0.1-5,5-10, 10-20, 20-30, 30-40, 40-45, 45-50, 50-60, 60-70, 70-80, 80-90, 90-99, and 99-100% can be a high efficiency. As will be appreciated by one of skill in the art, the desirable efficiency can be different in different embodiments, depending upon, for example, the associated agent, the amount of antibody that can be administered to an area, the side effects of the antibody-agent complex, the type (e.g., cancer type) and severity of the problem to be treated.

In other embodiments, the antibodies disclosed herein provide an assay kit for the detection of Shh expression in mammalian tissues or cells in order to screen for a disease or disorder associated with changes in expression of Shh. The kit comprises an antibody that binds Shh and means for indicating the reaction of the antibody with the antigen, if present.

Combinations

The targeted binding agent or antibody defined herein may be applied as a sole therapy or may involve, in addition to the compounds of the invention, conventional surgery or radiotherapy or chemotherapy. Such chemotherapy may include one or more of the following categories of anti tumour agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94461) and N-(2-chloro-6-methylphenyl)-2-[6-{4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat, inhibitors of urokinase plasminogen activator receptor function or, inhibitors of cathepsins, inhibitors of serine proteases for example matriptase, hepsin, urokinase, inhibitors of heparanase);

(iv) cytotoxic agents such as fludarabine, 2-chlorodeoxyadenosine, chlorambucil or doxorubicin and combination thereof such as Fludarabine+cyclophosphamide, CVP: cyclophosphamide+vincristine+prednisone, ACVBP: doxorubicin+cyclophosphamide+vindesine+bleomycin+prednisone, CHOP: cyclophosphamide+doxorubicin+vincristine+prednisone, CNOP: cyclophosphamide+mitoxantrone+vincristine+prednisone, m-BACOD: methotrexate+bleomycin+doxorubicin+cyclophosphamide+vincristine+dexamethasone+leucovorin, MACOP-B: methotrexate+doxorubicin+cyclophosphamide+vincristine+prednisone fixed dose+bleomycin+leucovorin, or ProMACE CytaBOM: prednisone+doxorubicin+cyclophosphamide+etoposide+cytarabine+bleomycin+vincristine+methotrexate+leucovorin.

(v) inhibitors of growth factor function, for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI-1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors, aurora kinase inhibitors (for example AZD1152, PH-739358, VX-680, MLN8054, R763, MP235, MP529, VX-528 and AX39459), cyclin dependent kinase inhibitors such as CDK2 and/or CDK4 inhibitors, and inhibitors of survival signaling proteins such as Bcl-2, Bcl-XL for example ABT-737;

(vi) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856, WO 98/13354, WO00/47212 and WO01/32651 and compounds that work by other mechanisms (for example linomide, inhibitors of integrin αvβ3 function and angiostatin)] or colony stimulating factor 1 (CSF1) or CSF1 receptor;

(vii) vascular damaging agents such as Combretastatin A4 and compounds disclosed in International Patent Applications WO 99/02166, WO 00/40529, WO 00/41669, WO 01/92224, WO 02/04446 and WO 02/08213;

(viii) antisense therapies, for example those which are directed to the targets listed above, such as G-3139 (Genasense), an anti bc12 antisense;

(ix) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (x) immunotherapy approaches, including for example treatment with Alemtuzumab (campath-1H™), a monoclonal antibody directed at CD52, or treatment with antibodies directed at CD22, ex vivo and in vivo approaches to increase the immunogenicity of patient tumour cells, transfection with cytokines such as interleukin 2, interleukin 4 or granulocyte macrophage colony stimulating factor, approaches to decrease T cell anergy such as treatment with monoclonal antibodies inhibiting CTLA-4 function, approaches using transfected immune cells such as cytokine transfected dendritic cells, approaches using cytokine transfected tumour cell lines and approaches using anti idiotypic antibodies.

(xi) inhibitors of protein degradation such as proteasome inhibitor such as Velcade (bortezomib).

(xii) biotherapeutic therapeutic approaches for example those which use peptides or proteins (such as antibodies or soluble external receptor domain constructions) which either sequester receptor ligands, block ligand binding to receptor or decrease receptor signalling (e.g. due to enhanced receptor degradation or lowered expression levels).

In one embodiment the anti-tumour treatment defined herein may involve, in addition to the compounds of the invention, treatment with other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin).

In one embodiment the anti-tumour treatment defined herein may involve, in addition to the compounds of the invention, treatment with gemcitabine.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically active agent within its is approved dosage range.

EXAMPLES

The following examples, including the experiments conducted and results achieved are provided for illustrative purposes only and are not to be construed as limiting upon the teachings herein.

Example 1

Immunization and Titering

Immunization

Monoclonal antibodies against human sonic hedgehog (Shh) were developed by sequential immunizations of XenoMouse mice. Immunizations for campaign 1 were conducted using soluble recombinant human Shh (Cat #1314-SH/CF, R&D Systems) and KLH-conjugated Shh (Shh-KLH). In campaign 1, recombinant human Shh (10 µg/mouse) was administered via intraperitoneal (IP) injection with TiterMax Gold (Sigma Cat #T2684) in the initial boost. The following six boosts used 5 µg of Shh per mouse, alternating injections into the tail with a is mixture of CpG DNA (ImmunEasy Mouse Adjuvant, cat #303101, Qiagen) and Adju-Phos (aluminum phosphate gel, cat #1452-250, HCl Biosector) with IP injections of Shh combined with TiterMax Gold. These six boosts were administered twice a week. Another nine boosts were performed with 5 µg of Shh-KLH per mouse given in an alternating manner via tail with CpG DNA and Adju-Phos and via IP injection with TiterMax Gold. The first six of these nine boosts were administered twice a week and the final three were given weekly. The final boost of 5 µg Shh-KLH in PBS was given base of tail IP.

CHO cells transiently transfected with full length human Shh were used as the immunogen in campaign 2. The first injection of $2\times10^6$ cells mixed with Adju-Phos was administered IP. For the next 16 boosts, $1\times10^6$ cells were injected with Adju-Phos into either the tail or IP, and finally the final two boosts were injected base of tail IP. The first 14 boosts were given twice a week, and the remaining 5 boosts were given weekly.

Selection of Animals for Harvest by Titer

Titers of the antibody against human Shh were determined using Shh binding assays. Two methods were employed: antibody binding to Shh transiently expressed on 293T cells was measured using flow cytometry and antibody binding to immobilized biotinylated Shh was assessed in an ELISA format. At the end of the immunization program, fusions were performed using mouse myeloma cells and lymphocytes isolated from the spleens and lymph nodes of the immunized mice by means of electroporation, as described in Example 2.

Example 2

Recovery of Lymphocytes, B-Cell Isolations, Fusions and Generation of Hybridomas Immunized mice were sacrificed by cervical dislocation, and the draining lymph nodes were harvested and pooled from each cohort. There were two harvests performed for this program. Harvest 1 used six mice with ID numbers 159507, 159508, 159821, 159823, 163273, and 163325. Harvest 2 used six mice with ID numbers 159184, 159533, 159534, 159885, 163335, and 163337.

The lymphoid cells were dissociated by grinding in DMEM to release the cells from the tissues and the cells were suspended in DMEM. The cells were counted, and 0.9 ml DMEM per 100 million lymphocytes were added to the cell pellet to resuspend the cells gently but completely. Using 100 µl of CD90+ magnetic beads per 100 million cells, the cells were labeled by incubating with the magnetic beads at 4° C. for 15 minutes. The magnetically labeled cell suspension containing up to $10^8$ positive cells (or up to $2\times10^9$ total cells) was loaded onto a LS+ column and the column washed with DMEM. The total effluent was collected as the CD90-negative fraction (most of these cells were expected to be B cells).

The fusion was performed by mixing washed enriched Day 6 B cells with nonsecretory myeloma P3X63Ag8.653 cells purchased from ATCC, cat. #CRL 1580 (Kearney et al, J. Immunol. 123, 1979, 1548-1550) at a ratio of 1:4. The cell mixture was gently pelleted by centrifugation at 400×g for 4 minutes. After decanting of the supernatant, the cells were gently mixed using a 1 ml pipette. Preheated PEG (1 ml per $10^6$ B cells) was slowly added with gentle agitation over 1 minute followed by 1 minute of mixing. Preheated IDMEM (2 ml per $10^6$ B cells) was then added over 2 minutes with gentle agitation. Finally preheated IDMEM (8 ml per $10^6$ B cells) was added over 3 minutes.

The fused cells were spun down at 400×g for 6 minutes and resuspended in 20 ml of Selection media [DMEM (Invitrogen), 15% fetal bovine serum (FBS) (Hyclone), supplemented with L-glutamine, pen/strep, MEM Non-essential amino acids, Sodium Pyruvate, 2-Mercaptoethanol (all from Invitrogen), HA-Azaserine Hypoxanthine and OPI (oxaloacetate, pyruvate, bovine insulin) (both from Sigma) and IL-6 (Boehringer Mannheim)] per $10^6$ B cells. Cells were incubated for 20-30 minutes at 37° C. and then resuspended in 200 ml Selection media and cultured for 3-4 days in a T175 flask.

Day 3 post fusion the cells were collected, spun for 8 minutes at 400×g and resuspended in 10 ml Selection media per $10^6$ fused B cells. FACS analysis of hybridoma population was performed, and cells were subsequently frozen down.

Hybridomas were routinely grown in the selective medium. Exhaustive supernatants collected from the hybridomas that potentially produce anti-human Shh antibodies were subjected to subsequent screening assays.

Example 3

Antibody Titer Measurement

Native Antigen Binding of 293T Cells Transiently Transfected with Shh

FACS analysis was performed on 293T cells transiently transfected with human Shh compared to parental 293T cells to measure the titers of antibody against human Shh produced as described in Examples 1 and 2. Transfected or parental cells were seeded at 50,000 cells/well and incubated with 2 µl of sample (at 1:50 dilution) for one hour at 4° C. The wells were then washed and incubated with Cy5-conjugated goat anti-human antibody at 2 µg/mL and 7-Amino-Actinomycin (7AAD) at 5 µg/mL for 30 minutes at 4° C. Bound Shh was detected using FACS analysis. The positive control was rat anti-Shh antibody (cat #MAB4641, R&D Systems, Inc.), and negative controls included naïve XMG2 sera and naïve XMG4 (XM3C-1) sera. Table 2 lists the flow cytometry data obtained from analysis of sera from animals selected for subsequent hybridoma generation.

TABLE 2

Titers of antibody against human Shh as determined by flow cytometry analysis of tansiently transfected 293T cells

| Group | mouse ID | Parentals X Geo Mean | Transients X Geo Mean | Ratio |
|---|---|---|---|---|
| Group 1 | 159507 | 2.54 | 38.1 | 15.00 |
| Group 1 | 159508 | 2.45 | 99.78 | 40.73 |
| Group 1 | 159821 | 3.64 | 57.76 | 15.87 |
| Group 1 | 159823 | 2.34 | 40.09 | 17.13 |
| Group 2 | 163273 | 2.51 | 117.94 | 46.99 |
| Group 2 | 163325 | 2.52 | 93.86 | 37.25 |
| Group 3 | 159184 | 6.12 | 174.97 | 28.59 |
| Group 3 | 159533 | 19.16 | 58.92 | 3.08 |
| Group 3 | 159534 | 38.14 | 98.21 | 2.57 |
| Group 3 | 159885 | 12.15 | 116.53 | 9.59 |
| Group 4 | 163335 | 35.18 | 226.53 | 6.44 |
| Group 4 | 163337 | 6.95 | 36.48 | 5.25 |
| Rat anti Shh MAB4641: 2 ug/ml | | 2.18 | 964.91 | 442.62 |
| Rat anti Shh MAB4641: 0.2 ug/ml | | 2.09 | 221.43 | 105.95 |
| Rat anti Shh MAB4641: 0.02 ug/ml | | 2.08 | 28.46 | 13.68 |
| Naïve: IgG4 | | 2.38 | 2.45 | 1.03 |
| Naïve: IgG2 | | 2.3 | 2.34 | 1.02 |
| Anti-rat - cy5 | | 2.02 | 2.31 | 1.14 |
| Anti-human - cy5 | | 1.95 | 2.14 | 1.10 |

Example 4

Antibody Titer Measurement

Binding to Immobilized Biotin-Shh

An ELISA assay of binding to immobilized biotinylated human Shh was used to measure titers of antibody produced as described in Examples 1 and 2.

To measure the titers of antibody, plates (Costar 3368 96 well medium binding plates) were coated with neutravadin at 8 ug/ml in 1×PBS, 0.05% azide by incubation at 37° C. for 1 hr. Plates were blocked with 250 µl/well of 1% milk in PBS for 30 min at RT. Subsequently, 50 µl of 500 ng/ml biotinylated Shh in 1×PBS, 1% milk (wt/vol) were added per well and incubated for 1 hr at RT. Antibodies were then titrated 1:3 in duplicate starting at a 1:100 dilution in blocking buffer (1×PBS, 1% milk) and added to each well. The plates were incubated for one hour at room temperature, washed, and subsequently incubated with secondary antibody diluted 1:1000 (goat anti-human IgG Fc POD; Jackson Laboratories) for one hour at room temperature. Plates were subsequently washed, and One-step TMB solution was added (50 µl/well) and allowed to develop for 30 min at RT. Development reactions were quenched with an equal volume of 1 N HCl. Absorbance was measured at 450 nm. The positive controls were goat-anti-Shh (cat #AF464, R&D Systems) and rat-anti-Shh (cat #MAB4641, R&D Systems) titrated 1:3 from 1 µg/ml (secondary antibodies: rabbit-anti-rat IgG Fc POD diluted 1:1250 and rabbit-anti-goat IgG Fc POD diluted 1:1000, respectively). Negative controls included naïve XMG2 sera and naïve XMG4 (XM3C-1) sera. Table 3 provides a summary of the ELISA readings obtained from analysis of the bound antibodies. The values indicate the calculated dilution that yields an $OD_{450}$ measurement of 2. For sera that yielded an OD<2 at a 1:100 dilution, the OD obtained at 1:100 is provided.

TABLE 3

Titers of antibody against immobilized biotinylated Shh as measured by ELISA assay

| Mouse ID | biotin-Shh coated at 500 ng/ml |
|---|---|
| P159507 | <100 @ OD 1.794 |
| P159508 | 786 |
| P159821 | 170 |
| P159823 | 1054 |
| P163273 | 577 |
| P163325 | <100 @ OD 0.864 |
| P159184 | <100 @ OD 0.948 |
| P159533 | <100 @ OD 0.708 |
| P159534 | <100 @ OD 0.925 |
| P159885 | <100 @ OD 0.616 |
| P163335 | <100 @ OD 1.329 |
| P163337 | <100 @ OD 0.517 |
| Naïve G2 | <100 @ OD 0.417 |
| Naïve G4 | <100 @ OD 0.098 |
| Goat-anti-Shh | OD 6.000 at 1 ug/ml |
| Rat-anti-Shh 4641 | OD 4.806 at 1 ug/ml |

Example 5

Hybridoma Supernatant Screening Using Binding Assays

Hybridoma supernatants containing antibody, produced as described in Examples 1 and 2, were screened by assays that measure binding to immobilized biotinylated Shh.

To screen hybridoma supernatants for Shh binding activity, antibody binding to immobilized biotin-Shh in an ELISA format was performed essentially as described in Example 4. Plates (Costar 3702 medium binding 384 well plates) were coated with neutravadin at 4 ug/ml in 1×PBS, 0.05% azide by incubation overnight at 4° C. After blocking with 1% milk in PBS, 40 µl of 500 ng/ml biotinylated Shh in 1×PBS, 1% milk (wt/vol) was added to each well and incubated for 1 hr at RT. Hybridoma supernatants (10 µl/well) were added to 40 µl of 1% milk, 0.05% Tween-20 in PBS per well and incubated 1 hr at RT. Following washing and incubation with secondary antibody (100 ng/ml goat-anti-human IgG Fc HRP), wells were developed with TMB substrate and subsequently quenched with 1 N HCl. Table 4 provides a summary of the ELISA readings obtained from analysis of the bound antibodies.

TABLE 4

Binding of antibody in hybridoma supernatants to immobilized biotin-Shh in an ELISA format.

| MAb ID | OD450 |
|---|---|
| 1A5 | 6.000 |
| 1A8 | 3.935 |
| 1A12 | 4.094 |
| 1B4 | 1.148 |
| 1B5 | 0.217 |
| 1B7 | 3.543 |
| 1B11 | 0.270 |
| 1C4 | 2.686 |
| 1C6 | 0.183 |
| 1C7 | 0.071 |
| 1C8 | 0.264 |
| 1D11 | 1.237 |
| 1E1 | 1.604 |
| 1E3 | 0.222 |
| 1E5 | 6.000 |
| 1F4 | 6.000 |
| 1F6 | 1.409 |
| 1F8 | 0.423 |
| 1F9 | 0.203 |
| 1F11 | 0.256 |
| 1G1 | 4.301 |
| 1G2 | 0.337 |
| 1G4 | 3.886 |
| 1G5 | 1.182 |
| 1G12 | 2.488 |
| 1H2 | 3.668 |
| 1H4 | 2.463 |
| 1H8 | 4.044 |
| 1H10 | 3.464 |
| 1H12 | 3.732 |
| 3H8 | 3.809 |
| 4B1 | 6.000 |
| 4B6 | 5.141 |
| 4C7 | 0.374 |
| 4D2 | 2.337 |
| 4G1 | 2.351 |

Hybridoma supernatants were also screened for binding activity to native human Shh expressed on the surface of transiently transfected 293T cells using FMAT (Fluorometric Microvolume Assay Technology). Transient transfection of 293T cells was performed using 1 µg of DNA and 1 µl of 293fectin (Invitrogen) per 1×10$^6$ cells. Cells were maintained at 1×10$^6$ cells/ml overnight at 37° C., 5% CO$_2$. Transfected cells were seeded into 384 well plates at 2500 cells/well along with 17,500 untransfected parental cells/well. Supernatants were added to each well (10 µl/well) and incubated 1.5 hrs at RT. Cy5-labeled secondary goat-anti-human IgG Fc antibody was added to each well (10 µl/well) to a final concentration of 4.25 µg/ml and incubated 3 hrs at RT. Plates were read on the FMAT 8100 HTS system from Applied Biosystems. The results are depicted in Table 5. Total signal (FL1×count) is defined as the number of positive cells in a well (count) multiplied by the average fluorescence intensity of the positive cells (FL1).

TABLE 5

FMAT results for binding of hybridoma supernatants to human Shh-expressing 293T cells

| MAb ID | FL1 X COUNT |
|---|---|
| 1A5 | 303670 |
| 1A8 | 1350000 |
| 1A12 | 695962 |
| 1B4 | 95254 |
| 1B5 | 6701 |
| 1B7 | 1520000 |
| 1B11 | 13905 |
| 1C4 | 546230 |
| 1C6 | 9483 |
| 1C7 | 662522 |
| 1C8 | 318681 |
| 1D11 | 344755 |
| 1E1 | 361701 |
| 1E3 | 25061 |
| 1E5 | 675001 |
| 1F4 | 109736 |
| 1F6 | 356652 |
| 1F8 | 8715 |
| 1F9 | 160469 |
| 1F11 | 74402 |
| 1G1 | 584995 |
| 1G2 | 733536 |

TABLE 5-continued

FMAT results for binding of hybridoma supernatants to human Shh-expressing 293T cells

| MAb ID | FL1 X COUNT |
|---|---|
| 1G4 | 1460000 |
| 1G5 | 394227 |
| 1G12 | 326617 |
| 1H2 | 596793 |
| 1H4 | 687003 |
| 1H8 | 89614 |
| 1H10 | 370397 |
| 1H12 | 1110000 |
| 3H8 | 497445 |
| 4B1 | 779544 |
| 4B6 | 624883 |
| 4C7 | 52968 |
| 4D2 | 1270000 |
| 4G1 | 471936 |
| 6D7 | 661436 |
| 7C3 | 859651 |
| 7F3 | 858556 |
| 13C8 | 1150000 |
| Rat-anti-Shh MAB 4641 (10 µg/ml) | 1470000 |

Finally, binding of antibody in exhaust hybridoma supernatants to native Shh was assessed using flow cytometry. Human Shh was expressed on the surface of transiently transfected HEK 293T cells as described above in Example 5. Transfected or parental cells were seeded into the plates with V-bottom wells (50,000 cells/well). Exhaust supernatants (50 µl of a 1:10 dilution) were added to each well and incubated at 4° C. for 1 hr. Rat-anti-Shh MAB4641 was used as a positive control. It was added to a concentration of 2 µg/ml in a volume of 50 µl. Cells were washed and 50 µl of a 2 µg/ml solution of secondary antibody (Cy5-labeled goat-anti-human IgG or Cy5-labeled goat-anti-rabbit IgG) were added to each well. 7AAD was added to a concentration of 5 µg/ml and the mixture was incubated for 30 min at RT. The mean fluorescence for each sample was then determined using flow cytometry. The results are displayed in Table 6.

TABLE 6

Binding of anti-Shh antibody in exhaust hybridoma supernatants to cell surface expressed Shh

| ID | Parentals X Geo Mean | Transients X Geo Mean | ratio |
|---|---|---|---|
| 1A5 | 3.8 | 265.0 | 70.5 |
| 1A8 | 3.6 | 4.6 | 1.3 |
| 1A12 | 3.7 | 289.7 | 78.1 |
| 1B4 | 3.9 | 1.1 | 0.3 |
| 1B5 | 3.6 | 1.1 | 0.3 |
| 1B7 | 3.6 | 58.7 | 16.5 |
| 1B11 | 3.1 | 4.2 | 1.3 |
| 1C4 | 3.7 | 1.1 | 0.3 |
| 1C6 | 4.0 | 9.8 | 2.4 |
| 1C7 | 3.7 | 5.5 | 1.5 |
| 1C8 | 3.5 | 117.7 | 33.3 |
| 1D11 | 3.4 | 8.5 | 2.5 |
| 1 E1 | 3.2 | 35.4 | 11.1 |
| 1 E3 | 3.5 | 4.9 | 1.4 |
| 1 E5 | 3.6 | 3.9 | 1.1 |
| 1F4 | 3.4 | 218.9 | 63.8 |
| 1F6 | 3.5 | 8.6 | 2.5 |
| 1F8 | 3.5 | 4.2 | 1.2 |
| 1F9 | 3.9 | 2.1 | 0.5 |
| 1F11 | 3.5 | 4.3 | 1.2 |
| 1G1 | 3.4 | 188.5 | 55.3 |
| 1G2 | 3.2 | 4.3 | 1.3 |
| 1G4 | 3.5 | 14.0 | 4.0 |

TABLE 6-continued

Binding of anti-Shh antibody in exhaust hybridoma supernatants to cell surface expressed Shh

| ID | Parentals X Geo Mean | Transients X Geo Mean | ratio |
|---|---|---|---|
| 1G5 | 3.6 | 121.0 | 33.3 |
| 1G12 | 3.8 | 8.3 | 2.2 |
| 1H2 | 3.6 | 55.6 | 15.4 |
| 1H4 | 3.9 | 3.9 | 1.0 |
| 1H8 | 3.7 | 165.0 | 44.1 |
| 1H10 | 3.7 | 150.1 | 40.9 |
| 1H12 | 3.8 | 34.4 | 9.1 |
| 3H8 | 3.8 | 147.7 | 39.2 |
| 4B1 | 3.8 | 5.1 | 1.3 |
| 4B6 | 3.9 | 196.4 | 50.2 |
| 4C7 | 3.6 | 10.8 | 3.0 |
| 4D2 | 3.8 | 75.7 | 19.7 |
| 4G1 | 3.6 | 2.4 | 0.7 |
| 6D7 | 3.7 | 313.1 | 83.9 |
| 7C3 | 3.6 | 266.1 | 74.9 |
| 7F3 | 3.6 | 102.8 | 28.8 |
| 13C8 | 3.7 | 1.6 | 0.4 |
| Rat-anti-Shh mAb 4641 | 4.2 | 3.0 | 0.7 |
| Irrelevant Sup | 4.1 | 1.2 | 0.3 |
| 2° alone | 3.9 | 1.4 | 0.3 |

Example 6

Determination of Relative Activity of Antibody-Containing Supernatants

The relative potency of the various antibody-containing supernatants was compared by measuring how well they inhibited induction of a Gli1 luciferase reporter expressed in NIH 3T3 cells in a co-culture assay system. The NIH 3T3 cells stably express a firefly luciferase reporter construct containing multiple copies of the Gli1 binding site upstream of the luciferase transcription start site in the promoter region. The cells also harbor a *Renilla* luciferase construct used to normalize for non-specific effects.

NIH 3T3-Gli1 cells were plated at 6000 cells/well in phenol red-free DMEM with 10% FBS in 96 well plates and incubated overnight at 37° C., 5% $CO_2$. HEK 293T cells were transiently transfected with pJP110, a pCR3.1-based (cat #12347019, Invitrogen) mammalian expression construct for full length human Shh. Cells were transfected with 1 µg of DNA per $10^6$ cells using 293fectin lipid reagent, and they were incubated overnight with rocking at 37° C., 5% $CO_2$. Shh-transfected 293T cells (24,000 cells/well) were preincubated with 20% (vol/vol) hybridoma supernatant in a total volume of 100 µl of medium at 37° C. for 2 hrs. Medium was removed from the NIH 3T3-Gli1 cells and replaced with 75 µl of transfected 293T cells in medium containing the hybridoma supernatant. The cells were co-cultured overnight at 37° C., 5% $CO_2$. The following day, 75 µl of Dual-Glo luciferase reagent (cat #E2940, Promega) were added to each well and incubated for 10 min at RT. The firefly luciferase signal was then immediately measured using a 500 msec read time on the Tecan luminometer. Dual-Glo Stop solution (40 µl/well) was added to each well and incubated for 10 min. The *Renilla* luciferase signal was then obtained from a 500 msec read using the Tecan instrument. The results of duplicate experiments with 40 anti-Shh hybridoma supernatants are shown in Table 7.

The neutralizing activity of anti-Shh hybridoma supernatants was also examined in a similar reporter assay using conditioned medium (CM) containing soluble Shh-N, the N-terminal signaling domain of Shh, to stimulate Gli1 reporter activity.

The CM reporter assay was carried out using the same protocols as the co-culture reporter assay with several modifications. Shh-containing conditioned medium (12.5% vol/vol) was preincubated with hybridoma supernatant (20% vol/vol) in phenol-red free DMEM containing 10% FBS for 2 hrs 37° C. NIH 3T3-Gli1 cells (seeded at 6000 cells/well) were treated with 75 µl of Shh CM-supernatant mix overnight at 37° C., 5% $CO_2$. The following day, firefly and *Renilla* luciferase activities were determined as described above. The results of duplicate experiments are displayed in Table 7.

TABLE 7

Hybridoma supernatants inhibit Shh-dependent stimulation of the Gli1 reporter in NIH 3T3 cells

| MAb ID | Co-Culture N = 1 % Inh | Co-Culture N = 2 % Inh | CM N = 1 % Inh | CM N = 3 % Inh |
|---|---|---|---|---|
| 1A5 | 20 | 27 | 73 | 62 |
| 1A8 | 23 | 26 | 52 | 47 |
| 1A12 | 40 | 32 | 25 | 43 |
| 1B4 | 30 | 25 | 45 | 30 |
| 1B5 | 28 | 26 | 59 | 46 |
| 1B7 | 28 | 30 | 45 | 45 |
| 1B11 | 36 | 33 | 59 | 48 |
| 1C4 | 18 | 34 | 41 | 45 |
| 1C6 | 24 | 22 | 46 | 46 |
| 1C7 | 22 | 23 | 42 | 49 |
| 1C8 | 32 | 24 | 47 | 43 |
| 1D11 | 19 | 24 | 42 | 45 |
| 1E1 | 27 | 34 | 33 | 45 |
| 1E3 | 21 | 26 | 42 | 45 |
| 1E5 | 26 | 29 | 64 | 56 |
| 1F4 | 31 | 47 | 21 | 9 |
| 1F6 | 31 | 20 | 57 | 48 |
| 1F8 | 22 | 30 | 59 | 43 |
| 1F9 | 21 | 20 | 42 | 58 |
| 1F11 | 35 | 18 | 49 | 41 |
| 1G1 | 42 | 39 | 33 | 47 |

TABLE 7-continued

Hybridoma supernatants inhibit Shh-dependent stimulation of the Gli1 reporter in NIH 3T3 cells

| MAb ID | Co-Culture N = 1 % Inh | Co-Culture N = 2 % Inh | CM N = 1 % Inh | CM N = 3 % Inh |
|---|---|---|---|---|
| 1G2 | 14 | 30 | 37 | 51 |
| 1G4 | 27 | 17 | 53 | 37 |
| 1G5 | 2 | 24 | 51 | 60 |
| 1G12 | 30 | 35 | 32 | 40 |
| 1H2 | 24 | 43 | 42 | 53 |
| 1H4 | 23 | 41 | 58 | 42 |
| 1H8 | 38 | 42 | 52 | 42 |
| 1H10 | 37 | 23 | 43 | 28 |
| 1H12 | 48 | 19 | 38 | 40 |
| 3H8 | 35 | 32 | 21 | −24 |
| 4B1 | 7 | 37 | 56 | 44 |
| 4B6 | 31 | 34 | 46 | 22 |
| 4C7 | 10 | −6 | 41 | 45 |
| 4D2 | −4 | 20 | 50 | 58 |
| 4G1 | 29 | 23 | 44 | 54 |
| 6D7 | 46 | 22 | −8 | −1 |
| 7C3 | 56 | 33 | 5 | 5 |
| 7F3 | 47 | 21 | 0 | −5 |
| 13C8 | 47 | 21 | −6 | −14 |

Example 7

Determination of the Relative Activity of Purified Antibody in the Gli1 Reporter Assays The activity of purified antibody material derived from hybridoma subclones of candidate antibodies was evaluated in the Gli1 reporter assay. These assays were conducted as described in Example 6. Purified antibodies were serially diluted 1:5 starting at a concentration of 20 µg/ml. The results of duplicate experiments in both assay formats, in which the source of Shh is supplied by co-cultured transfected 293T cells or in conditioned medium, is reported in Table 8. Significant inhibition was observed at only 20 µg/ml, and as a result, only those data are shown.

TABLE 8

Purified subclone-derived antibody inhibits Shh-dependent stimulation of the Gli1 reporter in NIH 3T3 cells

| MAb ID | conc. µg/ml | Conditioned Media N = 1 % Inhibition | Conditioned Media N = 2 % Inhibition | Co-Culture N = 1 % Inhibition | Co-Culture N = 2 % Inhibition | Co-Culture N = 3 % Inhibition |
|---|---|---|---|---|---|---|
| 1A5 | 20 | 35% | 34% | 25% | 20% | 20% |
| 1A12 | 20 | 18% | 57% | 58% | 59% | 22% |
| 1C8 | 20 | −1% | 8% | 26% | 10% | 23% |
| 1F4 | 20 | 2% | 16% | 31% | 18% | 28% |
| 1G1 | 20 | 50% | 61% | 44% | 55% | 19% |
| 1G12 | 20 | 23% | 44% | 35% | 43% | 28% |
| 1H8 | 20 | 34% | 48% | 32% | 25% | 36% |
| 1H10 | 20 | 48% | 24% | 47% | 68% | 4% |
| 1H12 | 20 | −5% | −5% | 8% | 15% | 13% |
| 3H8 | 20 | 37% | 44% | 73% | 87% | No Data |
| 4B6 | 20 | 73% | 43% | 44% | 76% | 22% |
| 6D7 | 20 | 89% | 111% | 80% | 68% | No Data |
| rmHIP | 4 | 103% | 112% | 124% | 96% | 121% |
| huIgG2/4 | 20 | 2% | 23% | 18% | 7% | 2% |

Example 8

Structural Analysis of Shh Antibodies

The variable heavy chains and the variable light chains of the antibodies were sequenced to determine their DNA sequences. The complete sequence information for the anti-Shh antibodies is provided in the sequence listing with nucleotide and amino acid sequences for each gamma and kappa chain combination. The variable heavy sequences were analyzed to determine the VH family, the D-region sequence and the J-region sequence. The sequences were then translated to determine the primary amino acid sequence and compared to the germline VH, D and J-region sequences to assess somatic hypermutations.

Table 9 below is a table comparing the antibody heavy chain regions to their cognate germ line heavy chain region and the antibody light chain regions to their cognate germ line light chain region.

TABLE 9

| SEQ ID NO | Chain | V | D | J | FR1 | CDR1 | FR2 | CDR2 | FR3 | CDR3 | FR4 |
|---|---|---|---|---|---|---|---|---|---|---|---|
| 2 | 1A12VH | | | | QVQLVESGGGVVQPG RSLRLSCAASGFTFS | SYGMH | WVRQAPGKG LEWVA | VIWYDGSNEYYADSVKG | RFTISRDNSKNTLYL QMNSLRAEDTAVYYC AR | DLYYYGSGSPFDY | WGQGTLVTVSS |
| 61 | Germline VH 3-33 | | | 3-10 JH4 | QVQLVESGGGVVQPG RSLRLSCAASGFTFS | SYGMH | WVRQAPGKG LEWVA | VIWYDGSNKYYADSVKG | RFTISRDNSKNTLYL QMNSLRAEDTAVYYC | - - YYYGSGSYFDY | WGQGTLVTVSS |
| 4 | 1A12VL | | | | EIVMTQSPATLSVSP GERATLSC | RASQSVSSNLA | WYQQKPGQA PRLLIF | GVSIRAT | GIPARFSGSGSGTEF TLTISSLQSEDFAVY YC | QQYNDWPRPG | FGGGTKVEIK |
| 62 | Germline VK L2 | | | JK4 | EIVMTQSPATLSVSP GERATLSC | RASQSVSSNLA | WYQQKPGQA PRLLIY | GASTRAT | GIPARFSGSGSGTEF TLTISSLQSEDFAVY YC | QQYNNWPLT- | FGGGTKVEIK |
| 6 | 1G12VH | | | | QVQLVESGGGVVQPG RSLRLSCAASGFTFS | TYGMH | WVRQAPGKG LEWVA | VIWYDGSNKYYADSVNG | RFTISRDNSKNTLYL QMNSLRGEDTAVYYC AR | DLYYYGSGSPFDY | WGQGTLVTVSS |
| 63 | Germline VH 3-33 | | | 3-10 JH4 | QVQLVESGGGVVQPG RSLRLSCAASGFTFS | SYGMH | WVRQAPGKG LEWVA | VIWYDGSNKYYADSVKG | RFTISRDNSKNTLYL QMNSLRAEDTAVYYC AR | - - YYYGSGSYFDY | WGQGTLVTVSS |
| 8 | 1G12VL | | | | EIVMTQSPATLSVSPGERVTLSC | RASQSVSSNLA | WYQQKPGQA PRLLIY | GVSIRAT | GIPARFSGSGSGTEF TLTISSLQSEDFAVY YC | QQYDNWPRPG | FGGGTKVEIK |
| 64 | Germline Vk L2 | | | Jk4 | EIVMTQSPATLSVSPGERATLSC | RASQSVSSNLA | WYQQKPGQA PRLLIY | GASTRAT | GIPARFSGSGSGTEF TLTISSLQSEDFAVY YC | QQYNNWPLT- | FGGGTKVEIK |
| 10 | 1H10VH | | | | QVQLVESGGGVVQPG RSLRLSCAASGFTFS | SYGMH | WVRQAPGKG LEWVA | VIWNDGSNEYYADSVKG | RFTISRDNSKNTLYL QMNSLRAEDTAVYYC AR | DLYYYGSGSPFDD | WGQGTLVTVSS |
| 65 | Germline VH 3-33 | | | 3-10 JH4 | QVQLVESGGGVVQPG RSLRLSCAASGFTFS | SYGMH | WVRQAPGKG LEWVA | VIWYDGSNKYYADSVKG | RFTISRDNSKNTLYL QMNSLRAEDTAVYYC AR | - - YYYGSGSYFDY | WGQGTLVTVSS |
| 12 | 1H10VL | | | | EIVMTQSPGTLSVSPGERATLSC | RASQSVGSSNLA | WYQQKPGQA PRLLIF | GVSIRAT | GVPARFSGSGSGTEF TLTISSLQSEDFAVY YC | QQYNDWPRPG | FGGGTKVEIK |
| 66 | Germline VK L2 | | | JK4 | EIVMTQSPATLSVSPGERATLSC | RASQSVSSNLA | WYQQKPGQA PRLLIY | GASTRAT | GIPARFSGSGSGTEF TLTISSLQSEDFAVY YC | QQYNNWPLT- | FGGGTKVEIK |

TABLE 9-continued

| SEQ ID NO | Chain | V | D | J | FR1 | CDR1 | FR2 | CDR2 | FR3 | CDR3 | FR4 |
|---|---|---|---|---|---|---|---|---|---|---|---|
| 14 | 3H8VH | | | | QVQLVESGGGVVQPG RSLRLSCAASGFTFS | TYGMH | WVRQAPGKG LEWVA | VIWYDGSNKYYADSVKG | RFTISRDNSKNTLNL QMNSLRAEDTAVYYC AR | DLYYYGSGSPFDYWGQGTLVTVSS | WGQGTLVTVSS |
| 67 | Germline VH | 3-33 | 3-10 | JH4 | QVQLVESGGGVVQPG RSLRLSCAASGFTFS | SYGMH | WVRQAPGKG LEWVA | VIWYDGSNKYYADSVKG | RFTISRDNSKNTLYL QMNSLRAEDTAVYYC AR | -- YYYGSGSYFDY | WGQGTLVTVSS |
| 16 | 3H8VL | | | | EIVMTQSPATLSVSPGERATLSC | RASQSVSSNLA | WYQQKPGQA PRLLIF | GVSIRAT | GIPARFSGSGSGTEF TLTISSLQSEDFAVY YC | QQYNNWPRPG | FGGGTKVEIK |
| 68 | Germline VK | L2 | | JK4 | EIVMTQSPATLSVSPGERATLSC | RASQSVSSNLA | WYQQKPGQA PRLLIY | GASTRAT | GIPARFSGSGSGTEF TLTISSLQSEDFAVY YC | QQYNNWPLT- | FGGGTKVEIK |
| 18 | 4B6VH | | | | QVQLVESGGGVVQPG RSLRLSCAASGFTFS | TYGMH | WVRQAPGKG LEWVA | VIWYDGSNEYYADSVKG | RFTISRDNSKNTLYL QMNSLRAEDTAVYYC AR | DLYYYGSGSPFDYWGQGTLVTVSS | WGQGTLVTVSS |
| 69 | Germline VH | 3-33 | 3-10 | JH4 | QVQLVESGGGVVQPG RSLRLSCAASGFTFS | SYGMH | WVRQAPGKG LEWVA | VIWYDGSNKYYADSVKG | RFTISRDNSKNTLYL QMNSLRAEDTAVYYC AR | -- YYYGSGSYFDY | WGQGTLVTVSS |
| 20 | 4B6VL | | | | EIVMTQSPATLSVSPGERATLSC | RASQSVSSNLA | WYQQKPGQA PRLLIF | GISIRAT | GIPARFSGSGSGTEF TLTISSLQSEDFAVY YC | QQYNDWPRPG | FGGGTRVEIK |
| 70 | Germline VK | L2 | | JK4 | EIVMTQSPATLSVSPGERATLSC | RASQSVSSNLA | WYQQKPGQA PRLLIY | GASTRAT | GIPARFSGSGSGTEF TLTISSLQSEDFAVY YC | QQYNNWPLT- | FGGGTKVEIK |
| 22 | 1G1VH | | | | EVQLVESGGGLVKPG GSLRLSCAASGFTFS | SYSMN | WVRQAPGKG LEWVS | SFSSSSSSYIYYADSVKG | RFTISRDNAKNSLYL QMNSLRAEDTAVYYC AR | DRGDYVDYYYGM DV | WGQGTTVTVSS |
| 71 | Germline VH | 3-21 | 4-17 | JH6 | EVQLVESGGGLVKPG GSLRLSCAASGFTFS | SYSMN | WVRQAPGKG LEWVS | SISSSSSYIYY ADSVKG | RFTISRDNAKNSLYL QMNSLRAEDTAVYYC AR | DYGDY-- YYYGMDV | WGQGTTVTVSS |
| 24 | 1G1VL | | | | SYELTQPPSVSVSPGQTASITC | SGDKLDYKYIC | WYQQKPGQS PVLVIY | QDIKRPS | GIPERFSGSNSGNTA TLTISGTQAMDEADY YC | QAWDSNTPLV | FGGGTKLTVL |
| 72 | Germline VL | 3r | | JL2 | SYELTQPPSVSVSPGQTASITC | SGDKLGDKYAC | WYQQKPGQS PVLVIY | QDSKRPS | GIPERFSGSNSGNTA TLTISGTQAMDEADY YC | QAWDSSTAVV | FGGGTKLTVL |

TABLE 9-continued

| SEQ ID NO | Chain | V | D | J | FR1 | CDR1 | FR2 | CDR2 | FR3 | CDR3 | FR4 |
|---|---|---|---|---|---|---|---|---|---|---|---|
| 26 | 1F4VH | | | | EVQLVESGGGLVKPG GSLRLSCAASGFTFT | NAWMS | WVRQAPGKG LEWVG | RIKSKTDGGTTDYAAPVKG | RFTISRDDSKNTLYL QMNSLKTEDIAVYYC TT | DNFN | WGQGTLVTVSS |
| 73 | Germline VH 3-15 | | 1-20 | JH4 | EVQLVESGGGLVKPG GSLRLSCAASGFTFS | NAWMS | WVRQAPGKG LEWVG | RIKSKTDGGTTDYAAPVKG | RFTISRDDSKNTLYL QMNSLKTEDTAVYYC TT | -NMN | WGQGTLVTVSS |
| 28 | 1F4VL | | | | EIVMTQSPATLSVSPGERATLSC | RASQSISSNLA | WYQQKPGQA PRLLIY | GASTRAT | GIPARFSGSGSGTEF TLTISSLQSEDFAVY FC | QQYHSW-WT | FGGGTKVEIQ |
| 74 | Germline VK L2 | | | JK1 | EIVMTQSPATLSVSPGERATLSC | RASQVSSNLA | WYQQKPGQA PRLLIY | GASTRAT | GIPARFSGSGSGTEF TLTISSLQSEDFAVY YC | QQYNNWPWT | FGQGTKVEIK |
| 30 | 1H8VH | | | | QVQLQESGPGLVKPS ETLSLTCTVSGGSIS | SYYWT | WIRQPPGKG LEWIG | YIYYSGSTNYN PSLKS | RVTISVDTSKNQFSL KLSSVTAADTAVYYC AR | DRLLYGMDV | WGQGTTVTVSS |
| 75 | Germline VH 4-59 | | 2-21 | JH6 | QVQLQESGPGLVKPS ETLSLTCTVSGGSIS | SYYWS | WIRQPPGKG LEWIG | YIYYSGSTNYN PSLKS | RVTISVDTSKNQFSL KLSSVTAADTAVYYC AR | --LLYGMDV | WGQGTTVTVSS |
| 32 | 1H8VL | | | | EIVFTQSPGTLSLSPGEGATLSC | RASQIVSSSYLA | WYQQKPGQA PRLLIY | GASSRAT | GIPDRFSGSGSGTDF TLTISRLEPEDFAVY YC | QHYGSSP-T | FGGGIKVEIK |
| 76 | Germline VK A27 | | | JK4 | EIVLTQSPGTLSLSPGERATLSC | RASQVSSSYLA | WYQQKPGQA PRLLIY | GASSRAT | GIPDRFSGSGSGTDF TLTISRLEPEDFAVY YC | QQYGSSPLT | FGGGTKVEIK |
| 34 | 1H12VH | | | | QVQLVQSGAEVKKPG ASVKVSCKASGYTFT | GYYMH | WVRQAPGQG LEWMG | WFNPNSGGTNC AQKFQG | RVTMTRDTSISTAYM ELSRLRSDDTAVYYC AR | EAVESYYYYGLDV | WGQGTTVTVSS |
| 77 | Germline VH 1-02 | | 6-19 | JH6 | QVQLVQSGAEVKKPG ASVKVSCKASGYTFT | GYYMH | WVRQAPGQG LEWMG | WINPNSGGTNY AQKFQG | RVTMTRDTSISTAYM ELSRLRSDDTAVYYC AR | -AV--YYYGMDV | WGQGTTVTVSS |
| 36 | 1H12VL | | | | QSVVTQPPSASGTPGQRITISC | SGSSSNIGSNY VY | WYHQLPGSA PNLLIY | RNNQRPS | GVPDRFSGSKSGTSA SLAISGLRSEDEADY FC | AVWDDSLRGVV | FGGGTKLTVL |
| 78 | Germline VL 1g | | | JL2 | QSVLTQPPSASGTPGQRVTISC | SGSSSNIGSNY VY | WYQQLPGTA PKLLIY | RNNQRPS | GVPDRFSGSKSGTSA SLAISGLRSEDEADY YC | AAWDDSLSGVV | FGGGTKLTVL |

TABLE 9-continued

| SEQ ID NO | Chain | V | D | J | FR1 | CDR1 | FR2 | CDR2 | FR3 | CDR3 | FR4 |
|---|---|---|---|---|---|---|---|---|---|---|---|
| 38 | 1C8VH | | | | EVQLVESGGGLIQPG GSLRLSCAVSGFTVS | SNCMN | WVRQAPGKG LEWVS | VIYSGGKTAYA DSVKG | RFTISRDNSKNTLCL QMNSLRAEDTAVYYC AR | DSSMVVGLGYFDL | WGRGTLVTVSS |
| 79 | Germline VH 3-53*01 | | 2-15 | JH2 | EVQLVESGGGLIQPG GSLRLSCAASGFTVS | SNYMS | WVRQAPGKG LEWVS | VIYSGGSTYYA DSVKG | RFTISRDNSKNTLYL QMNSLRAEDTAVYYC AR | ----VV--- YFDL | WGRGTLVTVSS |
| 40 | 1C8VL | | | | SYELTQPPSVSVSPGLTASITC | SGDKLGYKYAS | WYQQKPGQS PVLVIY | QDIKRPS | GIPERFSGSNSGNTA TLTISGTQAMDEADY YC | QAWDSST-VV | FGGGTKLTVL |
| 80 | Germline VL 3r | | | JL2 | SYELTQPPSVSVSPGQTASITC | SGDKLGDKYAC | WYQQKPGQS PVLVIY | QDSKRPS | GIPERFSGSNSGNTA TLTISGTQAMDEADY YC | QAWDSSTAVV | FGGGTKLTVL |
| 42 | 1A5VH | | | | EVQVVESGGDLIQPG GSLRLSCVASGFTVS | SNYMN | WVRQAPGKG LEWVS | VIYSGGNTYYA DSVKG | RFTISRDNSKNTLYL QMNSLRAEDTAVYYC AR | DSSVVVGLGYFDL | WGRGTLVTVSS |
| 81 | Germline VH 3-53*01 | | 2-15 | JH2 | EVQLVESGGGLIQPG GSLRLSCAASGFTVS | SNYMS | WVRQAPGKG LEWVS | VIYSGGSTYYA DSVKG | RFTISRDNSKNTLYL QMNSLRAEDTAVYYC AR | ---VVV--- YFDL | WGRGTLVTVSS |
| 44 | 1A5VL | | | | SYELTQPPSVSVSPGQTASITC | SGDKLGANYAS | WYQQKPGQS PVLVIY | QDTKRPS | GIPERFSGSNSGNTA TLTISGTQAMDEADY YC | QAWDFST-VI | FGGGTKLTVL |
| 82 | Germline VL 3r | | | JL2 | SYELTQPPSVSVSPGQTASITC | SGDKLGDKYAC | WYQQKPGQS PVLVIY | QDSKRPS | GIPERFSGSNSGNTA TLTISGTQAMDEADY YC | QAWDSSTAVV | FGGGTKLTVL |
| 46 | 6D7VH | | | | QVQLQESGPGLVKPS QTLSLTCTVSGGSIN | SGGFYWS | WIRQHPGKN LEWIG | SIYYSGNTYYN PSLKS | RVTISVDTSKNQFSL KLTSVTVSGGSIN AR | GNDSGDYDWYFDL | WGRGTLVTVSS |
| 83 | Germline VH 4-31 | | 4-17 | JH2 | QVQLQESGPGLVKPS QTLSLTCTVSGGSIS | SGGYYWS | WIRQHPGKG LEWIG | YIYYSGSTYYN PSLKS | RVTISVDTSKNQPSL KLSSVTAADTAVYYC AR | --DYGDYYWYFDL | WGRGTLVTVSS |
| 48 | 6D7VL | | | | SYELTQPPSVSVSPQTASITCG | SGEKLGYKVC | WYQQKPGQS PVLVIF | HDNKRPS | GIPERFSGSNSGNTA TLTISGAQAMDEADY YC | QAGDSSA--V | FGGGTKLTVL |
| 84 | Germline VL 3r | | | JL2 | SYELTQPPSVSVSPGQTASITC | SGDKLGDKYAC | WYQQKPGQS PVLVIY | QDSKRPS | GIPERFSGSNSGNTA TLTISGTQAMDEADY YC | QAWDSSTAVV | FGGGTKLTVL |

Immunoglobulin genes undergo various modifications during maturation of the immune response, including recombination between V, D and J gene segments, isotype switching, and hypermutation in the variable regions. Recombination and somatic hypermutation are the foundation for generation of antibody diversity and affinity maturation, but they can also generate sequence liabilities that may make commercial production of such immunoglobulins as therapeutic agents difficult, or increase the immunogenicity risk of the antibody. In general, mutations in CDR regions are likely to contribute to improved affinity and function, while mutations in framework regions may increase the risk of immunogenicity. This risk can be reduced by reverting framework mutations to germline, while ensuring that activity of the antibody is not adversely impacted. Some structural liabilities may be generated by the diversification processes, or they may exist within germline sequences contributing to the heavy and light chain variable domains. Regardless of the source, it may be desirable to remove potential structural liabilities that may result in instability, aggregation, heterogeneity of product, or increased immunogenicity. Examples of undesirable liabilities include unpaired cysteines (which may lead to disulfide bond scrambling, or variable sulfhydryl adduct formation), N-linked glycosylation sites (resulting in heterogeneity of structure and activity), as well as deamidation (e.g. NG, NS), isomerization (DG), oxidation (exposed methionine), and hydrolysis (DP) sites.

In order to reduce the risk of immunogenicity, and improve pharmaceutical properties of lead antibodies, it may be desirable to reduce the number of mutations from germline and/or remove structural liabilities.

Thus, in one embodiment, where a particular antibody differs from its respective germline sequence at the amino acid level, the antibody sequence can be mutated back to the germline sequence. Such corrective mutations can occur at one, two, three or more positions, or a combination of any of the mutated positions, using standard molecular biological techniques. By way of non-limiting example, Table 12 shows that the heavy chain sequence of mAb 3H8 (SEQ ID NO.: 14) differs from the corresponding germline sequence (see Table 9) through an T to an S mutation (mutation 1) at residue number 31 and an N to a Y at residue number 80, or a P to a Y at residue number 108. Thus, the amino acid or nucleotide sequence encoding the heavy chain of mAb 3H8 can be modified to change mutation 1 to yield the germline sequence at the site of mutation 1. Further, the amino acid or nucleotide sequence encoding the heavy chain of mAb 3H8 can be modified to change mutation 2 to yield the germline sequence at the site of mutation 2. Further, the amino acid or nucleotide sequence encoding the heavy chain of mAb 3H8 can be modified to change mutation 3 to yield the germline sequence at the site of mutation 3. Still further, the amino acid or nucleotide sequence encoding the heavy chain of mAb 3H8 can be modified to change at mutation 1, mutation 2 and mutation 3, or any other combination of two or more mutations to yield the germline sequence at those particular sites. Tables 10-15 below illustrate the positions of such variations from the germline for mAb 6D7, 3H8, and 1G1. Each row represents a unique combination of germline and non-germline residues at the position indicated by bold type.

In another embodiment, the invention includes replacing any structural liabilities in the sequence that might affect the heterogeneity of the antibodies of the invention. Such liabilities include glycosylation sites, un-paired cysteines, surface exposed methionines, etc. To reduce the risk of such heterogeneity it is proposed that changes are made to remove one or more of such structural liabilities.

In one embodiment, it may be desirable to remove one or more consensus N-linked glycosylation sites from the antibody germline or antibody sequence. One skilled in the art would be readily able to identify such a glycosylation site. Typically an N-linked glycosylation consensus site sequence has the sequence of Asn-any AA-Ser or Thr where the middle amino acid cannot be a proline (Pro). An example of an occurrence of a glycosylation site is NDS in the heavy chain of 6D7 (SEQ ID NO:46 at residue number 101-3). In this example, the N at position 101 of the glycosylation site NDS was mutated to a Q. However, the N could have been mutated to any appropriate amino acid that has comparable side chain properties. It should be noted that the modification of the S at position 103 in the glycosylation site NDS caused a reduction in binding to Shh.

In another example, unpaired cysteines can be replaced alone or in conjunction with other structural changes. An example of an unpaired cysteine occurs in the light chain CDR1 of antibody 6D7 at position 33. This unpaired cysteine can be mutated to an appropriate amino acid that has comparable side chain properties such as a serine. In another example, an unpaired cysteine occurs in the light chain CDR1 of antibody 1G1 at position 33. This unpaired cysteine can likewise be mutated to an appropriate amino acid that has comparable side chain properties such as a serine.

As referred to herein, a sequence that is optimized is a sequence which has been mutated at one or more positions back to its germline sequence or can be modified to remove one or more structural liabilities. An optimized sequence can also include a sequence that has been mutated at one or more positions back to its germline sequence and which has also been further modified to remove one or more structural liabilities.

TABLE 10

Exemplary Mutations of mAB 6D7 Heavy Chain (SEQ ID NO: 46) to Germline at the Indicated Residue Number

| 30 | 34 | 46 | 52 | 58 | 85 | 103 | 107 |
|----|----|----|----|----|----|-----|-----|
| S | F | N | S | N | T | S | D |
| N | F | N | S | N | T | S | D |
| S | Y | N | S | N | T | S | D |
| N | Y | N | S | N | T | S | D |
| S | F | G | S | N | T | S | D |
| N | F | G | S | N | T | S | D |
| S | Y | G | S | N | T | S | D |
| N | Y | G | S | N | T | S | D |
| S | F | N | Y | N | T | S | D |
| N | F | N | Y | N | T | S | D |
| S | Y | N | Y | N | T | S | D |
| N | Y | N | Y | N | T | S | D |
| S | F | G | Y | N | T | S | D |
| N | F | G | Y | N | T | S | D |
| S | Y | G | Y | N | T | S | D |
| N | Y | G | Y | N | T | S | D |
| S | F | N | S | S | T | S | D |
| N | F | N | S | S | T | S | D |
| S | Y | N | S | S | T | S | D |
| N | Y | N | S | S | T | S | D |
| S | F | G | S | S | T | S | D |
| N | F | G | S | S | T | S | D |
| S | Y | G | S | S | T | S | D |
| N | Y | G | S | S | T | S | D |
| S | F | N | Y | S | T | S | D |
| N | F | N | Y | S | T | S | D |
| S | Y | N | Y | S | T | S | D |
| N | Y | N | Y | S | T | S | D |
| S | F | G | Y | S | T | S | D |
| N | F | G | Y | S | T | S | D |
| S | Y | G | Y | S | T | S | D |
| N | Y | G | Y | S | T | S | D |

TABLE 10-continued

Exemplary Mutations of mAB 6D7 Heavy Chain (SEQ ID NO: 46) to Germline at the Indicated Residue Number

| 30 | 34 | 46 | 52 | 58 | 85 | 103 | 107 |
|---|---|---|---|---|---|---|---|
| S | F | N | S | N | S | S | D |
| N | F | N | S | N | S | S | D |
| S | Y | N | S | N | S | S | D |
| N | Y | N | S | N | S | S | D |
| S | F | G | S | N | S | S | D |
| N | F | G | S | N | S | S | D |
| S | Y | G | S | N | S | S | D |
| N | Y | G | S | N | S | S | D |
| S | F | N | Y | N | S | S | D |
| N | F | N | Y | N | S | S | D |
| S | Y | N | Y | N | S | S | D |
| N | Y | N | Y | N | S | S | D |
| S | F | G | Y | N | S | S | D |
| N | F | G | Y | N | S | S | D |

TABLE 10-continued

Exemplary Mutations of mAB 6D7 Heavy Chain (SEQ ID NO: 46) to Germline at the Indicated Residue Number

| 30 | 34 | 46 | 52 | 58 | 85 | 103 | 107 |
|---|---|---|---|---|---|---|---|
| S | Y | G | S | S | S | S | Y |
| N | Y | G | S | S | S | S | Y |
| S | F | N | Y | S | S | S | Y |
| N | F | N | Y | S | S | S | Y |
| S | Y | N | Y | S | S | S | Y |
| N | Y | N | Y | S | S | S | Y |
| S | F | G | Y | S | S | S | Y |
| N | F | G | Y | S | S | S | Y |
| S | Y | G | Y | S | S | S | Y |
| N | Y | G | Y | S | S | S | Y |
| S | F | N | S | N | T | Y | Y |
| N | F | N | S | N | T | Y | Y |
| S | Y | N | S | N | T | Y | Y |
| N | Y | N | S | N | T | Y | Y |
| S | F | G | S | N | T | Y | Y |
| N | F | G | S | N | T | Y | Y |
| S | Y | G | S | N | T | Y | Y |
| N | Y | G | S | N | T | Y | Y |
| S | F | N | Y | N | T | Y | Y |
| N | F | N | Y | N | T | Y | Y |
| S | Y | N | Y | N | T | Y | Y |
| N | Y | N | Y | N | T | Y | Y |
| S | F | G | Y | N | T | Y | Y |
| N | F | G | Y | N | T | Y | Y |
| S | Y | G | Y | N | T | Y | Y |
| N | Y | G | Y | N | T | Y | Y |
| S | F | N | S | S | T | Y | Y |
| N | F | N | S | S | T | Y | Y |
| S | Y | N | S | S | T | Y | Y |
| N | Y | N | S | S | T | Y | Y |
| S | F | G | S | S | T | Y | Y |
| N | F | G | S | S | T | Y | Y |
| S | Y | G | S | S | T | Y | Y |
| N | Y | G | S | S | T | Y | Y |
| S | F | N | Y | S | T | Y | Y |
| N | F | N | Y | S | T | Y | Y |
| S | Y | N | Y | S | T | Y | Y |
| N | Y | N | Y | S | T | Y | Y |
| S | F | G | Y | S | T | Y | Y |
| N | F | G | Y | S | T | Y | Y |
| S | Y | G | Y | S | T | Y | Y |
| N | Y | G | Y | S | T | Y | Y |
| S | F | N | S | N | S | Y | Y |
| N | F | N | S | N | S | Y | Y |
| S | Y | N | S | N | S | Y | Y |
| N | Y | N | S | N | S | Y | Y |
| S | F | G | S | N | S | Y | Y |
| N | F | G | S | N | S | Y | Y |
| S | Y | G | S | N | S | Y | Y |
| N | Y | G | S | N | S | Y | Y |
| S | F | N | Y | N | S | Y | Y |
| N | F | N | Y | N | S | Y | Y |
| S | Y | N | Y | N | S | Y | Y |
| N | Y | N | Y | N | S | Y | Y |
| S | F | G | Y | N | S | Y | Y |
| N | F | G | Y | N | S | Y | Y |
| S | Y | G | Y | N | S | Y | Y |
| N | Y | G | Y | N | S | Y | Y |
| S | F | N | S | S | S | Y | Y |
| N | F | N | S | S | S | Y | Y |
| S | Y | N | S | S | S | Y | Y |
| N | Y | N | S | S | S | Y | Y |
| S | F | G | S | S | S | Y | Y |
| N | F | G | S | S | S | Y | Y |
| S | Y | G | S | S | S | Y | Y |
| N | Y | G | S | S | S | Y | Y |
| S | F | N | Y | S | S | Y | Y |
| N | F | N | Y | S | S | Y | Y |
| S | Y | N | Y | S | S | Y | Y |
| N | Y | N | Y | S | S | Y | Y |
| S | F | G | Y | S | S | Y | Y |
| N | F | G | Y | S | S | Y | Y |
| S | Y | G | Y | S | S | Y | Y |
| N | Y | G | Y | S | S | Y | Y |

In some embodiments of the invention, the targeted binding agent or antibody comprises a sequence comprising SEQ ID NO.: 46. In certain embodiments, SEQ ID NO.: 46 comprises any one of the combinations of germline and non-germline residues indicated by each row of Table 10. In some embodiments, SEQ ID NO: 46 comprises any one, any two, any three, any four, any five, any six, any seven, any eight, or all eight of the germline residues as indicated in Table 10. In certain embodiments, SEQ ID NO.: 46 comprises any one of the unique combinations of germline and non-germline residues indicated by each row of Table 10. However, it should be noted that the modification of the S at position 103 to a Y amino acid residue resulted in a reduction of binding of the antibody to Shh. In other embodiments, the targeted binding agent or antibody is derived from a germline sequence with VH4-31, D4-17 and JH2 domains, wherein one or more residues has been mutated to yield the corresponding germline residue at that position. In a specific example of 6D7 variable heavy domain which has been mutated to particular germline sequences includes 6D7 VHOP (optimized where the non-germline sequence N has been mutated to an G at position 46 and a T has been mutated to a S at position 85). The modified sequence is also further modified/optimized to remove the potential glycosylation site NDS-the N which occurs at position 101 is mutated to a Q. Various optimized variable heavy chain sequences of 6D7 are shown in Table 16. Moreover, it should be noted that the modification of N30 to germline S resulted in a loss of potency.

TABLE 11

Exemplary Mutations of mAB 6D7 Light Chain (SEQ ID NO: 48) to Germline at the Indicated Residue Number

| 25 | 29 | 32 | 48 | 49 | 51 | 77 | 90 | 94 |
|---|---|---|---|---|---|---|---|---|
| D | Y | V | F | H | N | A | G | A |
| E | Y | V | F | H | N | A | G | A |
| D | D | V | F | H | N | A | G | A |
| E | D | V | F | H | N | A | G | A |
| D | Y | A | F | H | N | A | G | A |
| E | Y | A | F | H | N | A | G | A |
| D | D | A | F | H | N | A | G | A |
| E | D | A | F | H | N | A | G | A |
| D | Y | V | Y | H | N | A | G | A |
| E | Y | V | Y | H | N | A | G | A |
| D | D | V | Y | H | N | A | G | A |
| E | D | V | Y | H | N | A | G | A |
| D | Y | A | Y | H | N | A | G | A |
| E | Y | A | Y | H | N | A | G | A |
| D | D | A | Y | H | N | A | G | A |
| E | D | A | Y | H | N | A | G | A |
| D | Y | V | F | Q | N | A | G | A |
| E | Y | V | F | Q | N | A | G | A |
| D | D | V | F | Q | N | A | G | A |
| E | D | V | F | Q | N | A | G | A |
| D | Y | A | F | Q | N | A | G | A |
| E | Y | A | F | Q | N | A | G | A |
| D | D | A | F | Q | N | A | G | A |
| E | D | A | F | Q | N | A | G | A |
| D | Y | V | Y | Q | N | A | G | A |
| E | Y | V | Y | Q | N | A | G | A |
| D | D | V | Y | Q | N | A | G | A |
| E | D | V | Y | Q | N | A | G | A |
| D | Y | A | Y | Q | N | A | G | A |
| E | Y | A | Y | Q | N | A | G | A |
| D | D | A | Y | Q | N | A | G | A |
| E | D | A | Y | Q | N | A | G | A |
| D | Y | V | F | H | S | A | G | A |
| E | Y | V | F | H | S | A | G | A |
| D | D | V | F | H | S | A | G | A |
| E | D | V | F | H | S | A | G | A |
| D | Y | A | F | H | S | A | G | A |
| E | Y | A | F | H | S | A | G | A |
| D | D | A | F | H | S | A | G | A |

TABLE 11-continued

Exemplary Mutations of mAB 6D7 Light Chain (SEQ ID NO: 48) to Germline at the Indicated Residue Number

| 25 | 29 | 32 | 48 | 49 | 51 | 77 | 90 | 94 |
|----|----|----|----|----|----|----|----|----|
| E | D | A | F | H | S | A | G | A |
| D | Y | V | Y | H | S | A | G | A |
| E | Y | V | Y | H | S | A | G | A |
| D | D | V | Y | H | S | A | G | A |
| E | D | V | Y | H | S | A | G | A |
| D | Y | A | Y | H | S | A | G | A |
| E | Y | A | Y | H | S | A | G | A |
| D | D | A | Y | H | S | A | G | A |
| E | D | A | Y | H | S | A | G | A |
| D | Y | V | F | Q | S | A | G | A |
| E | Y | V | F | Q | S | A | G | A |
| D | D | V | F | Q | S | A | G | A |
| E | D | V | F | Q | S | A | G | A |
| D | Y | A | F | Q | S | A | G | A |
| E | Y | A | F | Q | S | A | G | A |
| D | D | A | F | Q | S | A | G | A |
| E | D | A | F | Q | S | A | G | A |
| D | Y | V | Y | Q | S | A | G | A |
| E | Y | V | Y | Q | S | A | G | A |
| D | D | V | Y | Q | S | A | G | A |
| E | D | V | Y | Q | S | A | G | A |
| D | Y | A | Y | Q | S | A | G | A |
| E | Y | A | Y | Q | S | A | G | A |
| D | D | A | Y | Q | S | A | G | A |
| E | D | A | Y | Q | S | A | G | A |
| D | Y | V | F | H | N | T | G | A |
| E | Y | V | F | H | N | T | G | A |
| D | D | V | F | H | N | T | G | A |
| E | D | V | F | H | N | T | G | A |
| D | Y | A | F | H | N | T | G | A |
| E | Y | A | F | H | N | T | G | A |
| D | D | A | F | H | N | T | G | A |
| E | D | A | F | H | N | T | G | A |
| D | Y | V | Y | H | N | T | G | A |
| E | Y | V | Y | H | N | T | G | A |
| D | D | V | Y | H | N | T | G | A |
| E | D | V | Y | H | N | T | G | A |
| D | Y | A | Y | H | N | T | G | A |
| E | Y | A | Y | H | N | T | G | A |
| D | D | A | Y | H | N | T | G | A |
| E | D | A | Y | H | N | T | G | A |
| D | Y | V | F | Q | N | T | G | A |
| E | Y | V | F | Q | N | T | G | A |
| D | D | V | F | Q | N | T | G | A |
| E | D | V | F | Q | N | T | G | A |
| D | Y | A | F | Q | N | T | G | A |
| E | Y | A | F | Q | N | T | G | A |
| D | D | A | F | Q | N | T | G | A |
| E | D | A | F | Q | N | T | G | A |
| D | Y | V | Y | Q | N | T | G | A |
| E | Y | V | Y | Q | N | T | G | A |
| D | D | V | Y | Q | N | T | G | A |
| E | D | V | Y | Q | N | T | G | A |
| D | Y | A | Y | Q | N | T | G | A |
| E | Y | A | Y | Q | N | T | G | A |
| D | D | A | Y | Q | N | T | G | A |
| E | D | A | Y | Q | N | T | G | A |
| D | Y | V | F | H | S | T | G | A |
| E | Y | V | F | H | S | T | G | A |
| D | D | V | F | H | S | T | G | A |
| E | D | V | F | H | S | T | G | A |
| D | Y | A | F | H | S | T | G | A |
| E | Y | A | F | H | S | T | G | A |
| D | D | A | F | H | S | T | G | A |
| E | D | A | F | H | S | T | G | A |
| D | Y | V | Y | H | S | T | G | A |
| E | Y | V | Y | H | S | T | G | A |
| D | D | V | Y | H | S | T | G | A |
| E | D | V | Y | H | S | T | G | A |
| D | Y | A | Y | H | S | T | G | A |
| E | Y | A | Y | H | S | T | G | A |
| D | D | A | Y | H | S | T | G | A |
| E | D | A | Y | H | S | T | G | A |
| D | Y | V | F | Q | S | T | G | A |
| E | Y | V | F | Q | S | T | G | A |
| D | D | V | F | Q | S | T | G | A |
| E | D | V | F | Q | S | T | G | A |
| D | Y | A | F | Q | S | T | G | A |
| E | Y | A | F | Q | S | T | G | A |
| D | D | A | F | Q | S | T | G | A |
| E | D | A | F | Q | S | T | G | A |
| D | Y | V | Y | Q | S | T | G | A |
| E | Y | V | Y | Q | S | T | G | A |
| D | D | V | Y | Q | S | T | G | A |
| E | D | V | Y | Q | S | T | G | A |
| D | Y | A | Y | Q | S | T | G | A |
| E | Y | A | Y | Q | S | T | G | A |
| D | D | A | Y | Q | S | T | G | A |
| E | D | A | Y | Q | S | T | G | A |
| D | Y | V | F | H | N | A | W | A |
| E | Y | V | F | H | N | A | W | A |
| D | D | V | F | H | N | A | W | A |
| E | D | V | F | H | N | A | W | A |
| D | Y | A | F | H | N | A | W

TABLE 11-continued

Exemplary Mutations of mAB 6D7 Light Chain (SEQ ID NO: 48) to Germline at the Indicated Residue Number

| 25 | 29 | 32 | 48 | 49 | 51 | 77 | 90 | 94 |
|---|---|---|---|---|---|---|---|---|
| E | Y | A | Y | Q | S | A | W | A |
| D | D | A | Y | Q | S | A | W | A |
| E | D | A | Y | Q | S | A | W | A |
| D | Y | V | F | H | N | T | W | A |
| E | Y | V | F | H | N | T | W | A |
| D | D | V | F | H | N | T | W | A |
| E | D | V | F | H | N | T | W | A |
| D | Y | A | F | H | N | T | W | A |
| E | Y | A | F | H | N | T | W | A |
| D | D | A | F | H | N | T | W | A |
| E | D | A | F | H | N | T | W | A |
| D | Y | V | Y | H | N | T | W | A |
| E | Y | V | Y | H | N | T | W | A |
| D | D | V | Y | H | N | T | W | A |
| E | D | V | Y | H | N | T | W | A |
| D | Y | A | Y | H | N | T | W | A |
| E | Y | A | Y | H | N | T | W | A |
| D | D | A | Y | H | N | T | W | A |
| E | D | A | Y | H | N | T | W | A |
| D | Y | V | F | Q | N | T | W | A |
| E | Y | V | F | Q | N | T | W | A |
| D | D | V | F | Q | N | T | W | A |
| E | D | V | F | Q | N | T | W | A |
| D | Y | A | F | Q | N | T | W | A |
| E | Y | A | F | Q | N | T | W | A |
| D | D | A | F | Q | N | T | W | A |
| E | D | A | F | Q | N | T | W | A |
| D | Y | V | Y | Q | N | T | W | A |
| E | Y | V | Y | Q | N | T | W | A |
| D | D | V | Y | Q | N | T | W | A |
| E | D | V | Y | Q | N | T | W | A |
| D | Y | A | Y | Q | N | T | W | A |
| E | Y | A | Y | Q | N | T | W | A |
| D | D | A | Y | Q | N | T | W | A |
| E | D | A | Y | Q | N | T | W | A |
| D | Y | V | F | H | S | T | W | A |
| E | Y | V | F | H | S | T | W | A |
| D | D | V | F | H | S | T | W | A |
| E | D | V | F | H | S | T | W | A |
| D | Y | A | F | H | S | T | W | A |
| E | Y | A | F | H | S | T | W | A |
| D | D | A | F | H | S | T | W | A |
| E | D | A | F | H | S | T | W | A |
| D | Y | V | Y | H | S | T | W | A |
| E | Y | V | Y | H | S | T | W | A |
| D | D | V | Y | H | S | T | W | A |
| E | D | V | Y | H | S | T | W | A |
| D | Y | A | Y | H | S | T | W | A |
| E | Y | A | Y | H | S | T | W | A |
| D | D | A | Y | H | S | T | W | A |
| E | D | A | Y | H | S | T | W | A |
| D | Y | V | F | Q | S | T | W | A |
| E | Y | V | F | Q | S | T | W | A |
| D | D | V | F | Q | S | T | W | A |
| E | D | V | F | Q | S | T | W | A |
| D | Y | A | F | Q | S | T | W | A |
| E | Y | A | F | Q | S | T | W | A |
| D | D | A | F | Q | S | T | W | A |
| E | D | A | F | Q | S | T | W | A |
| D | Y | V | Y | Q | S | T | W | A |
| E | Y | V | Y | Q | S | T | W | A |
| D | D | V | Y | Q | S | T | W | A |
| E | D | V | Y | Q | S | T | W | A |
| D | Y | A | Y | Q | S | T | W | A |
| E | Y | A | Y | Q | S | T | W | A |
| D | D | A | Y | Q | S | T | W | A |
| E | D | A | Y | Q | S | T | W | A |
| D | Y | V | F | H | N | A | G | T |
| E | Y | V | F | H | N | A | G | T |
| D | D | V | F | H | N | A | G | T |
| E | D | V | F | H | N | A | G | T |
| D | Y | A | F | H | N | A | G | T |
| E | Y | A | F | H | N | A | G | T |
| D | D | A | F | H | N | A | G | T |
| E | D | A | F | H | N | A | G | T |
| D | Y | V | Y | H | N | A | G | T |
| E | Y | V | Y | H | N | A | G | T |
| D | D | V | Y | H | N | A | G | T |
| E | D | V | Y | H | N | A | G | T |
| D | Y | A | Y | H | N | A | G | T |
| E | Y | A | Y | H | N | A | G | T |
| D | D | A | Y | H | N | A | G | T |
| E | D | A | Y | H | N | A | G | T |
| D | Y | V | F | Q | N | A | G | T |
| E | Y | V | F | Q | N | A | G | T |
| D | D | V | F | Q | N | A | G | T |
| E | D | V | F | Q | N | A | G | T |
| D | Y | A | F | Q | N | A | G | T |
| E | Y | A | F | Q | N | A | G | T |
| D | D | A | F | Q | N | A | G | T |
| E | D | A | F | Q | N | A | G | T |
| D | Y | V | Y | Q | N | A | G | T |
| E | Y | V | Y | Q | N | A | G | T |
| D | D | V | Y | Q | N | A | G | T |
| E | D | V | Y | Q | N | A | G | T |
| D | Y | A | Y | Q | N | A | G | T |
| E | Y | A | Y | Q | N | A | G | T |
| D | D | A | Y | Q | N | A | G | T |
| E | D | A | Y | Q | N | A | G | T |
| D | Y | V | F | H | S | A | G | T |
| E | Y | V | F | H | S | A | G | T |
| D | D | V | F | H | S | A | G | T |
| E | D | V | F | H | S | A | G | T |
| D | Y | A | F | H | S | A | G | T |
| E | Y | A | F | H | S | A | G | T |
| D | D | A | F | H | S | A | G | T |
| E | D | A | F | H | S | A | G | T |
| D | Y | V | Y | H | S | A | G | T |
| E | Y | V | Y | H | S | A | G | T |
| D | D | V | Y | H | S | A | G | T |
| E | D | V | Y | H | S | A | G | T |
| D | Y | A | Y | H | S | A | G | T |
| E | Y | A | Y | H | S | A | G | T |
| D | D | A | Y | H | S | A | G | T |
| E | D | A | Y | H | S | A | G | T |
| D | Y | V | F | Q | S | A | G | T |
| E | Y | V | F | Q | S | A | G | T |
| D | D | V | F | Q | S | A | G | T |
| E | D | V | F | Q | S | A | G | T |
| D | Y | A | F | Q | S | A | G | T |
| E | Y | A | F | Q | S | A | G | T |
| D | D | A | F | Q | S | A | G | T |
| E | D | A | F | Q | S | A | G | T |
| D | Y | V | Y | Q | S | A | G | T |
| E | Y | V | Y | Q | S | A | G | T |
| D | D | V | Y | Q | S | A | G | T |
| E | D | V | Y | Q | S | A | G | T |
| D | Y | A | Y | Q | S | A | G | T |
| E | Y | A | Y | Q | S | A | G | T |
| D | D | A | Y | Q | S | A | G | T |
| E | D | A | Y | Q | S | A | G | T |
| D | Y | V | F | H | N | T | G | T |
| E | Y | V | F | H | N | T | G | T |
| D | D | V | F | H | N | T | G | T |
| E | D | V | F | H | N | T | G | T |
| D | Y | A | F | H | N | T | G | T |
| E | Y | A | F | H | N | T | G | T |
| D | D | A | F | H | N | T | G | T |
| E | D | A | F | H | N | T | G | T |
| D | Y | V | Y | H | N | T | G | T |
| E | Y | V | Y | H | N | T | G | T |
| D | D | V | Y | H | N | T

TABLE 11-continued

Exemplary Mutations of mAB 6D7 Light Chain (SEQ ID NO: 48) to Germline at the Indicated Residue Number

| 25 | 29 | 32 | 48 | 49 | 51 | 77 | 90 | 94 |
|---|---|---|---|---|---|---|---|---|
| E | D | V | F | Q | N | T | G | T |
| D | Y | A | F | Q | N | T | G | T |
| E | Y | A | F | Q | N | T | G | T |
| D | D | A | F | Q | N | T | G | T |
| E | D | A | F | Q | N | T | G | T |
| D | Y | V | Y | Q | N | T | G | T |
| E | Y | V | Y | Q | N | T | G | T |
| D | D | V | Y | Q | N | T | G | T |
| E | D | V | Y | Q | N | T | G | T |
| D | Y | A | Y | Q | N | T | G | T |
| E | Y | A | Y | Q | N | T | G | T |
| D | D | A | Y | Q | N | T | G | T |
| E | D | A | Y | Q | N | T | G | T |
| D | Y | V | F | H | S | T | G | T |
| E | Y | V | F | H | S | T | G | T |
| D | D | V | F | H | S | T | G | T |
| E | D | V | F | H | S | T | G | T |
| D | Y | A | F | H | S | T | G | T |
| E | Y | A | F | H | S | T | G | T |
| D | D | A | F | H | S | T | G | T |
| E | D | A | F | H | S | T | G | T |
| D | Y | V | Y | H | S | T | G | T |
| E | Y | V | Y | H | S | T | G | T |
| D | D | V | Y | H | S | T | G | T |
| E | D | V | Y | H | S | T | G | T |
| D | Y | A | Y | H | S | T | G | T |
| E | Y | A | Y | H | S | T | G | T |
| D | D | A | Y | H | S | T | G | T |
| E | D | A | Y | H | S | T | G | T |
| D | Y | V | F | Q | S | T | G | T |
| E | Y | V | F | Q | S | T | G | T |
| D | D | V | F | Q | S | T | G | T |
| E | D | V | F | Q | S | T | G | T |
| D | Y | A | F | Q | S | T | G | T |
| E | Y | A | F | Q | S | T | G | T |
| D | D | A | F | Q | S | T | G | T |
| E | D | A | F | Q | S | T | G | T |
| D | Y | V | Y | Q | S | T | G | T |
| E | Y | V | Y | Q | S | T | G | T |
| D | D | V | Y | Q | S | T | G | T |
| E | D | V | Y | Q | S | T | G | T |
| D | Y | A | Y | Q | S | T | G | T |
| E | Y | A | Y | Q | S | T | G | T |
| D | D | A | Y | Q | S | T | G | T |
| E | D | A | Y | Q | S | T | G | T |
| D | Y | V | F | H | N | A | W | T |
| E | Y | V | F | H | N | A | W | T |
| D | D | V | F | H | N | A | W | T |
| E | D | V | F | H | N | A | W | T |
| D | Y | A | F | H | N | A | W | T |
| E | Y | A | F | H | N | A | W | T |
| D | D | A | F | H | N | A | W | T |
| E | D | A | F | H | N | A | W | T |
| D | Y | V | Y | H | N | A | W | T |
| E | Y | V | Y | H | N | A | W | T |
| D | D | V | Y | H | N | A | W | T |
| E | D | V | Y | H | N | A | W | T |
| D | Y | A | Y | H | N | A | W | T |
| E | Y | A | Y | H | N | A | W | T |
| D | D | A | Y | H | N | A | W | T |
| E | D | A | Y | H | N | A | W | T |
| D | Y | V | F | Q | N | A | W | T |
| E | Y | V | F | Q | N | A | W | T |
| D | D | V | F | Q | N | A | W | T |
| E | D | V | F | Q | N | A | W | T |
| D | Y | A | F | Q | N | A | W | T |
| E | Y | A | F | Q | N | A | W | T |
| D | D | A | F | Q | N | A | W | T |
| E | D | A | F | Q | N | A | W | T |
| D | Y | V | Y | Q | N | A | W | T |
| E | Y | V | Y | Q | N | A | W | T |
| D | D | V | Y | Q | N | A | W | T |
| E | D | V | Y | Q | N | A | W | T |
| D | Y | A | Y | Q | N | A | W | T |
| E | Y | A | Y | Q | N | A | W | T |
| D | D | A | Y | Q | N | A | W | T |
| E | D | A | Y | Q | N | A | W | T |
| D | Y | V | F | H | S | A | W | T |
| E | Y | V | F | H | S | A | W | T |
| D | D | V | F | H | S | A | W | T |
| E | D | V | F | H | S | A | W | T |
| D | Y | A | F | H | S | A | W | T |
| E | Y | A | F | H | S | A | W | T |
| D | D | A | F | H | S | A | W | T |
| E | D | A | F | H | S | A | W | T |
| D | Y | V | Y | H | S | A | W | T |
| E | Y | V | Y | H | S | A | W | T |
| D | D | V | Y | H | S | A | W | T |
| E | D | V | Y | H | S | A | W | T |
| D | Y | A | Y | H | S | A | W | T |
| E | Y | A | Y | H | S | A | W | T |
| D | D | A | Y | H | S | A | W | T |
| E | D | A | Y | H | S | A | W | T |
| D | Y | V | F | Q | S | A | W | T |
| E | Y | V | F | Q | S | A | W | T |
| D | D | V | F | Q | S | A | W | T |
| E | D | V | F | Q | S | A | W | T |
| D | Y | A | F | Q | S | A | W | T |
| E | Y | A | F | Q | S | A | W | T |
| D | D | A | F | Q | S | A | W | T |
| E | D | A | F | Q | S | A | W | T |
| D | Y | V | Y | Q | S | A | W | T |
| E | Y | V | Y | Q | S | A | W | T |
| D | D | V | Y | Q | S | A | W | T |
| E | D | V | Y | Q | S | A | W | T |
| D | Y | A | Y | Q | S | A | W | T |
| E | Y | A | Y | Q | S | A | W | T |
| D | D | A | Y | Q | S | A | W | T |
| E | D | A | Y | Q | S | A | W | T |
| D | Y | V | F | H | N | T | W | T |
| E | Y | V | F | H | N | T | W | T |
| D | D | V | F | H | N | T | W | T |
| E | D | V | F | H | N | T | W | T |
| D | Y | A | F | H | N | T | W | T |
| E | Y | A | F | H | N | T | W | T |
| D | D | A | F | H | N | T | W | T |
| E | D | A | F | H | N | T | W | T |
| D | Y | V | Y | H | N | T | W | T |
| E | Y | V | Y | H | N | T | W | T |
| D | D | V | Y | H | N | T | W | T |
| E | D | V | Y | H | N | T | W | T |
| D | Y | A | Y | H | N | T | W | T |
| E | Y | A | Y | H | N | T | W | T |
| D | D | A | Y | H | N | T | W | T |
| E | D | A | Y | H | N | T | W | T |
| D | Y | V | F | Q | N | T | W | T |
| E | Y | V | F | Q | N | T | W | T |
| D | D | V | F | Q | N | T | W | T |
| E | D | V | F | Q | N | T | W | T |
| D | Y | A | F | Q | N | T | W | T |
| E | Y | A | F | Q | N | T | W | T |
| D | D | A | F | Q | N | T | W | T |
| E | D | A | F | Q | N | T | W | T |
| D | Y | V | Y | Q | N | T | W | T |
| E | Y | V | Y | Q | N | T | W | T |
| D | D | V | Y | Q | N | T | W | T |
| E | D | V | Y | Q | N | T | W | T |
| D | Y | A | Y | Q | N | T | W | T |
| E | Y | A | Y | Q | N | T | W | T |
| D | D | A | Y | Q | N | T | W | T |
| E | D | A | Y | Q | N | T | W | T |
| D | Y | V | F | H | S | T | W | T |
| E | Y | V | F | H | S | T | W | T |
| D | D | V | F | H | S | T | W | T |
| E | D | V | F | H | S | T | W | T |
| D | Y | A | F | H | S | T | W | T |
| E | Y | A | F | H | S | T | W | T |
| D | D | A | F | H | S | T | W | T |
| E | D | A | F | H | S | T | W | T |
| D | Y | V | Y | H | S | T | W | T |

TABLE 11-continued

Exemplary Mutations of mAB 6D7 Light Chain (SEQ ID NO: 48) to Germline at the Indicated Residue Number

| 25 | 29 | 32 | 48 | 49 | 51 | 77 | 90 | 94 |
|---|---|---|---|---|---|---|---|---|
| E | Y | V | Y | H | S | T | W | T |
| D | D | V | Y | H | S | T | W | T |
| E | D | V | Y | H | S | T | W | T |
| D | Y | A | Y | H | S | T | W | T |
| E | Y | A | Y | H | S | T | W | T |
| D | D | A | Y | H | S | T | W | T |
| E | D | A | Y | H | S | T | W | T |
| D | Y | V | F | Q | S | T | W | T |
| E | Y | V | F | Q | S | T | W | T |
| D | D | V | F | Q | S | T | W | T |
| E | D | V | F | Q | S | T | W | T |
| D | Y | A | F | Q | S | T | W | T |
| E | Y | A | F | Q | S | T | W | T |
| D | D | A | F | Q | S | T | W | T |
| E | D | A | F | Q | S | T | W | T |
| D | Y | V | Y | Q | S | T | W | T |
| E | Y | V | Y | Q | S | T | W | T |
| D | D | V | Y | Q | S | T | W | T |
| E | D | V | Y | Q | S | T | W | T |
| D | Y | A | Y | Q | S | T | W | T |
| E | Y | A | Y | Q | S | T | W | T |
| D | D | A | Y | Q | S | T | W | T |
| E | D | A | Y | Q | S | T | W | T |

In some embodiments of the invention, the targeted binding agent or antibody comprises a sequence comprising SEQ ID NO.: 48. In certain embodiments, SEQ ID NO.: 48 comprises any one of the combinations of germline and non-germline residues indicated by each row of Table 11. In some embodiments, SEQ ID NO: 48 comprises any one, any two, any three, any four, any five, any six, any seven, any eight, any nine, or all nine of the germline residues as indicated in Table 11. In certain embodiments, SEQ ID NO.: 48 comprises any one of the unique combinations of germline and non-germline residues indicated by each row of Table 11. Specific examples of 6D7 variable light domain which has been mutated to particular germline sequences include 6D7 VLOP2 (optimized where the A has been mutated to a T at position 77) or 6D7 VLOP3 (optimized where the non-germline sequence F has been mutated to a Y at position 48 and an A has been mutated to a T at position 77) as shown in Table 11. Moreover, the 6D7 light chain can be further modified to remove unpaired cysteine. An example of an unpaired cysteine occurs in the light chain CDR1 of antibody 6D7 at position 33. This unpaired cysteine can be mutated to an appropriate amino acid that has comparable side chain properties such as a serine. 6D7 VLOP2 and 6D7 VLOP3 have been further optimized to remove this structural liability.

TABLE 12

Exemplary Mutations of mAB 3H8 Heavy Chain (SEQ ID NO: 14) to Germline at the Indicated Residue Number

| 31 | 80 | 108 |
|---|---|---|
| T | N | P |
| S | N | P |
| T | Y | P |
| S | Y | P |
| T | N | Y |
| S | N | Y |
| T | Y | Y |
| S | Y | Y |

In some embodiments of the invention, the targeted binding agent or antibody comprises a sequence comprising SEQ ID NO.: 14. In certain embodiments, SEQ ID NO.: 14 comprises any one of the combinations of germline and non-germline residues indicated by each row of Table 12. In some embodiments, SEQ ID NO: 14 comprises any one, any two, any three, or all three of the germline residues as indicated in Table 12. In certain embodiments, SEQ ID NO.: 14 comprises any one of the unique combinations of germline and non-germline residues indicated by each row of Table 12. In other embodiments, the targeted binding agent or antibody is derived from a germline sequence with VH3-33, D3-10 and JH4 domains, wherein one or more residues has been mutated to yield the corresponding germline residue at that position. Specific examples of 3H8 variable heavy domain which has been mutated to particular germline is sequences include 3H8VL OP (optimized where the non-germline sequence N has been mutated to a Y at position 80) is shown in Table 16.

TABLE 13

Exemplary Mutations of mAB 3H8 Light Chain (SEQ ID NO: 16) to Germline at the Indicated Residue Number

| 49 | 51 | 53 | 96 | 97 |
|---|---|---|---|---|
| F | V | I | R | P |
| Y | V | I | R | P |
| F | A | I | R | P |
| Y | A | I | R | P |
| F | V | T | R | P |
| Y | V | T | R | P |
| F | A | T | R | P |
| Y | A | T | R | P |
| F | V | I | L | P |
| Y | V | I | L | P |
| F | A | I | L | P |
| Y | A | I | L | P |
| F | V | T | L | P |
| Y | V | T | L | P |
| F | A | T | L | P |
| Y | A | T | L | P |
| F | V | I | R | T |
| Y | V | I | R | T |
| F | A | I | R | T |
| Y | A | I | R | T |
| F | V | T | R | T |
| Y | V | T | R | T |
| F | A | T | R | T |
| Y | A | T | R | T |
| F | V | I | L | T |
| Y | V | I | L | T |
| F | A | I | L | T |
| Y | A | I | L | T |
| F | V | T | L | T |
| Y | V | T | L | T |
| F | A | T | L | T |
| Y | A | T | L | T |

In some embodiments of the invention, the targeted binding agent or antibody comprises a sequence comprising SEQ ID NO.: 16. In certain embodiments, SEQ ID NO.: 16 comprises any one of the combinations of germline and non-germline residues indicated by each row of Table 13. In some embodiments, SEQ ID NO: 16 comprises any one, any two, any three, any four, any five, or all five of the germline residues as indicated in Table 13. In certain embodiments, SEQ ID NO.: 16 comprises any one of the unique combinations of germline and non-germline residues indicated by each row of Table 13. Specific examples of 3H8 variable light domain which has been mutated to particular germline sequences include 3H8 VLOP (optimized where the non-germline sequence F has been mutated to a Y at position 49) as shown in Table 16.

TABLE 14

Exemplary Mutations of mAB 1G1 Heavy Chain (SEQ ID NO: 22) to Germline at the Indicated Residue Number

| 51 | 100 |
|---|---|
| F | R |
| I | R |
| F | Y |
| I | Y |

In some embodiments of the invention, the targeted binding agent or antibody comprises a sequence comprising SEQ ID NO.: 22. In certain embodiments, SEQ ID NO.: 22 comprises any one of the combinations of germline and non-germline residues indicated by each row of Table 14. In some embodiments, SEQ ID NO: 22 comprises any one, any two, any three, or all three of the germline residues as indicated in Table 14. In certain embodiments, SEQ ID NO.: 22 comprises any one of the unique combinations of germline and non-germline residues indicated by each row of Table 14. In other embodiments, the targeted binding agent or antibody is derived from a germline sequence with VH3-21, D4-17 and JH6 domains, wherein one or more residues has been mutated to yield the corresponding germline residue at that position. It should be noted that a modification in the structural liability sequence of RGD, when the G is mutated to an A resulted in the elimination of activity.

TABLE 15

Exemplary Mutations of mAB 1G1 Light Chain (SEQ ID NO: 24) to Germline at the Indicated Residue Number

| 28 | 29 | 32 | 51 | 93 | 95 | 96 |
|---|---|---|---|---|---|---|
| D | Y | I | I | N | P | L |
| G | Y | I | I | N | P | L |
| D | D | I | I | N | P | L |
| G | D | I | I | N | P | L |
| D | Y | A | I | N | P | L |
| G | Y | A | I | N | P | L |
| D | D | A | I | N | P | L |
| G | D | A | I | N | P | L |
| D | Y | I | S | N | P | L |
| G | Y | I | S | N | P | L |
| D | D | I | S | N | P | L |
| G | D | I | S | N | P | L |
| D | Y | A | S | N | P | L |
| G | Y | A | S | N | P | L |
| D | D | A | S | N | P | L |
| G | D | A | S | N | P | L |
| D | Y | I | I | S | P | L |
| G | Y | I | I | S | P | L |
| D | D | I | I | S | P | L |
| G | D | I | I | S | P | L |
| D | Y | A | I | S | P | L |
| G | Y | A | I | S | P | L |
| D | D | A | I | S | P | L |
| G | D | A | I | S | P | L |
| D | Y | I | S | S | P | L |
| G | Y | I | S | S | P | L |
| D | D | I | S | S | P | L |
| G | D | I | S | S | P | L |
| D | Y | A | S | S | P | L |
| G | Y | A | S | S | P | L |
| D | D | A | S | S | P | L |
| G | D | A | S | S | P | L |
| D | Y | I | I | N | A | L |
| G | Y | I | I | N | A | L |
| D | D | I | I | N | A | L |
| G | D | I | I | N | A | L |
| D | Y | A | I | N | A | L |
| G | Y | A | I | N | A | L |
| D | D | A | I | N | A | L |
| G | D | A | I | N | A | L |
| D | Y | I | S | N | A | L |
| G | Y | I | S | N | A | L |
| D | D | I | S | N | A | L |
| G | D | I | S | N | A | L |
| D | Y | A | S | N | A | L |
| G | Y | A | S | N | A | L |
| D | D | A | S | N | A | L |
| G | D | A | S | N | A | L |
| D | Y | I | I | S | A | L |
| G | Y | I | I | S | A | L |
| D | D | I | I | S | A | L |
| G | D | I | I | S | A | L |
| D | Y | A | I | S | A | L |
| G | Y | A | I | S | A | L |
| D | D | A | I | S | A | L |
| G | D | A | I | S | A | L |
| D | Y | I | S | S | A | L |
| G | Y | I | S | S | A | L |
| D | D | I | S | S | A | L |
| G | D | I | S | S | A | L |
| D | Y | A | S | S | A | L |
| G | Y | A | S | S | A | L |
| D | D | A | S | S | A | L |
| G | D | A | S | S | A | L |
| D | Y | I | I | N | P | V |
| G | Y | I | I | N | P | V |
| D | D | I | I | N | P | V |
| G | D | I | I | N | P | V |
| D | Y | A | I | N | P | V |
| G | Y | A | I | N | P | V |
| D | D | A | I | N | P | V |
| G | D | A | I | N | P | V |
| D | Y | I | S | N | P | V |
| G | Y | I | S | N | P | V |
| D | D | I | S | N | P | V |
| G | D | I | S | N | P | V |
| D | Y | A | S | N | P | V |
| G | D | A | S | N | P | V |
| D | Y | I | I | S | P | V |
| G | Y | I | I | S | P | V |
| D | D | I | I | S | P | V |
| G | D | I | I | S | P | V |
| D | Y | A | I | S | P | V |
| G | Y | A | I | S | P | V |
| D | D | A | I | S | P | V |
| G | D | A | I | S | P | V |
| D | Y | I | S | S | P | V |
| G | Y | I | S | S | P | V |
| D | D | I | S | S | P | V |
| G | D | I | S | S | P | V |
| D | Y | A | S | S | P | V |
| G | D | A | S | S | P | V |
| D | Y | I | I | N | A | V |
| G | D | I | I | N | A | V |
| D | Y | A | I | N | A | V |
| G | D | A | I | N | A | V |
| D | Y | I | S | N | A | V |
| G | D | I | S | N | A | V |
| D | Y | A | S | N | A | V |
| G | D | A | S | N | A | V |
| D | Y | I | I | S | A | V |
| G | Y | I | I | S | A | V |

TABLE 15-continued

Exemplary Mutations of mAB 1G1 Light Chain (SEQ ID NO: 24) to Germline at the Indicated Residue Number

| 28 | 29 | 32 | 51 | 93 | 95 | 96 |
|----|----|----|----|----|----|----|
| D | D | I | I | S | A | V |
| G | D | I | I | S | A | V |
| D | Y | A | I | S | A | V |
| G | Y | A | I | S | A | V |
| D | D | A | I | S | A | V |
| G | D | A | I | S | A | V |
| D | Y | I | S | S | A | V |
| G | Y | I | S | S | A | V |
| D | D | I | S | S | A | V |
| G | D | I | S | S | A | V |
| D | Y | A | S | S | A | V |
| G | Y | A | S | S | A | V |
| D | D | A | S | S | A | V |
| G | D | A | S | S | A | V |

In some embodiments of the invention, the targeted binding agent or antibody comprises a sequence comprising SEQ ID NO.: 24. In certain embodiments, SEQ ID NO.: 24 comprises any one of the combinations of germline and non-germline residues indicated by each row of Table 15. In some embodiments, SEQ ID NO: 24 comprises any one, any two, any three, any four, any five, any six, any seven, or all seven of the germline residues as indicated in Table 15. In certain embodiments, SEQ ID NO.: 24 comprises any one of the unique combinations of germline and non-germline residues indicated by each row of Table 15.

All CDR boundaries in Table 9 are defined according to the Kabat definition.

Example 9

Determination of Functional Potency for Still Antibodies

The potency of purified Shh antibodies in an osteoblast differentiation assays in which Shh induces osteogenesis of C3H10T1/2 cells was determined.

C3H10T1/2 cells were seeded in 384 well clear bottom plates (cat #4336, Matrix) at 5000 cells/well in seeding media (MEM, 10% FBS, 1% L-Glutamine) and incubated overnight at 37° C., 5% $CO_2$. Antibodies were serially diluted in half log increments in Assay Medium and combined with an equal volume of 10% (vol/vol) conditioned medium (CM) containing Shh. Titrated antibodies were preincubated with Shh for 45 min in a polypropylene dilution plate at 37° C., 5% $CO_2$. The final concentration of antibodies ranged from 50 µg/ml to 20 ng/ml. Shh-containing CM was used at a final concentration of 5% (vol/vol). The concentration of the N-terminal signaling domain of Shh in 5% CM was determined to be approximately 10 nM. After the preincubation step was completed, seeding media was removed from all wells and replaced with 30 µl of medium containing a mixture of Shh and antibody. The cells were incubated for 72 h at 37° C., 5% $CO_2$.

Osteoblast differentiation was assessed by the production of alkaline phosphatase. Cells were washed twice with ice-cold PBS and subsequently lysed with 15 µl/well RIPA Lysis

TABLE 16

| SEQ ID No | Chain | V | FR1 | CDR1 | FR2 | CDR2 | FR3 | CDR3 | FR4 |
|-----------|-------|---|-----|------|-----|------|-----|------|-----|
| 50 | 6D7 OP (corresponding to deposit Mab6D7VHOP) | VH | QVQLQESGPGL VKPSQTLSLTC TVSGGSIN | SGGFYWS | WIRQHPGK GLEWIG | SIYYSGNTY YNPSLKS | RVTISVDTSKNQFSLK LSSVTAADTAVYYCAR | GQDSGDYD WYFDL | WGRGTLVTVSS |
| 52 | 6D7 OP (2) (corresponding to Mab6D7VLOP) | VL | SYELTQPPSVS VSPGQTASITC | SGEKLG YKYVS | WYQQKPGQ SPVLVIF | HDNKRPS | GIPERFSGSNSGNTAT LTISGTQAMDEADYYC | QAGDSSAV | FGGGTKLTVL |
| 54 | 6D7 OP | VL | SYELTQPPSVS VSPGQTASITC | SGEKLG YKYVS | WYQQKPGQ SPVLVIY | HDNKRPS | GIPERFSGSNSGNTAT LTISGTQAMDEADYYC | QAGDSSAV | FGGGTKLTVL |
| 58 | 3H8 OP | VH | QVQLVESGGGV VQPGRSLRLSC AASGFTFS | TYGMH | WVRQAPGK GLEWVA | VIWYDGSNK YYADSVKG | RFTISRDNSKNTLYLQ MNSLRAEDTAVYYCAR | DLYYYGSG SPFDY | WGQGTLVTVSS |
| 60 | 3H8 OP | VL | EIVMTQSPATL SVSPGERATLSC | RASQSV SSNLA | WYQQKPGQ APRLLIY | GVSIRAT | GIPARFSGSGSGTEFT LTISSLQSEDFAVYYC | QQYNNWPR PG | FGGGTKVEIK |
| 56 | 1G1 OP | VL | SYELTQPPSVS VSPGQTASITC | SGDKLD YKYIS | WYQQKPGQ SPVLVIY | QDIKRPS | GIPERFSGSNSGNTAT LTISGTQAMDEADYYC | QAWDSNTP LV | FGGGTKLTVL |

The skilled person will be aware that there are alternative methods of defining CDR boundaries. The starting residue of VH CDR1 in the Table 1 has been defined according to the method as described in Scaviner D, Barbie V, Ruiz M, Lefranc M-P. Protein Displays of the Human Immunoglobulin Heavy, Kappa and Lambda Variable and Joining Regions. Exp Clin Immunogenet 1999, 16:246-240. The remaining CDR boundaries in Table 9 are defined according to the Kabat definition.

and Extraction Buffer (cat #89900, Pierce). Plates were frozen at −80° C. for 20 min and thawed on the bench top. Substrate solution (1 mg/ml p-nitrophenyl phosphate, cat #N2765, Sigma-Aldrich), 1M diethanolamine (cat #D8885, Sigma-Aldrich), 0.5 mM $MgCl_2$, pH 9.8, made fresh) was added to each well (45 µl/well). Plates were incubated for at least 90 min at 37° C. and absorbance was measured at 405 nm. Data analysis was performed with GraphPad Prism. $IC_{50}$ values were calculated from dose-response curves and are reported in Table 17.

TABLE 17

Inhibition of Osteoblast Differentiation by Purified Antibody

| Antibody | $IC_{50}$ (nM) |
|---|---|
| 1G1 | 5.7 |
| 3H8 | 3.4 |
| 3H8OP | 5.6 |
| 1A12 | 4.6 |
| 1G12 | 7.1 |
| 1H10 | 4.4 |
| 4B6 | 3.3 |
| 1A5 | 4.8 |
| 6D7 | 5.3 |
| 1H8 | 5.7 |
| 5E1 | 2.9 |

Assay to Measure the Ability of Purified Antibody to Inhibit the Induction of Gli1 and Ptc1 mRNA in Shh-Treated C3H10T1/2 cells.

C3H10T1/2 cells were seeded in 96 well plates (200 µl/well) at 10,000 cells/well in seeding medium (MEM, 0.5% FBS, 1% L-Glut) and incubated overnight at 37° C., 5% $CO_2$. Antibodies were serially diluted and preincubated as described above in Example 9. After preincubation was completed, seeding media was removed from all wells and replaced with 100 µl of medium containing a mixture of Shh and antibody. The cells were incubated for 72 h at 37° C., 5% CO2.

RNA was prepared for quantitative RT-PCR (qRT-PCR) using the Cells to cT kit (cat #AM1728, ABI) according to the manufacturer's instructions. Briefly, cells were rinsed with cold PBS. Lysis solution was prepared by adding DNase I, and 50 µl of lysis solution were added per well and incubated for 5 min at RT. Subsequently, 5 µl of stop solution was added to each well and incubated for 2 min at RT. Plates were stored at −80° C. cDNA was prepared with 10 µl of cell lysate, 25 µl 2× Reverse Transcriptase (RT) Buffer, and 2.5 µl 20X RT Enzyme Mix in a final volume of 40 µl per sample. The RT reaction was carried out at 37° C. for 60 min and terminated by incubating the reaction at 95° C. for 5 min. Samples were stored at −80° C. overnight.

Quantitative PCR reactions were performed to measure the amount of mouse Gli1 and Ptc1 relative to HPRT1. The following ABI TaqMan primers/probe sets were used: mouse Gli1, Mm00494654_m1; mouse Ptc1, Mm00436026_m1; and mouse HPRT1, Mm00446968_m1. The thermal cycling reaction was prepared by combining 10 µl Universal 2×PCR Master Mix, 1 µl 20X probe/primer mix, and 5 µl cDNA template in a final volume of 2 µl. Samples were heated to 50° C. for 2 minutes followed by heating to 95° C. for 10 minutes. Cycling was carried out at 95° C. for 15 seconds and 60° C. for 1 minute for forty cycles on the ABI 7900HT Fast Real-time PCR system. The amount of mouse Gli1 and Ptc1 RNA in each sample was determined by calculating the delta delta Ct value for each sample using mouse HPRT1 as the internal standard (see Table 18).

TABLE 18

Inhibition of Endogenous Gli1 and Ptc1 mRNA in C3H10T1/2 Cells by Purified Antibody

| | Antibody activity $IC_{50}$ (nM) | |
|---|---|---|
| | 6D7 | 1G1 |
| Mouse Gli1 | 11.7 | 7.7 |
| Mouse Ptc1 | 8.2 | 8.7 |

Example 10

Binding of Purified Shh Antibodies to Human Shh

The binding of purified antibodies to recombinant human Shh was determined using an ELISA-based method. The N-terminal signaling domain of Shh, Shh-N, was presented in two forms: as a purified protein isolated from bacteria lacking lipid modifications and as a constituent of conditioned medium in a form that contains the N-terminal palmitoyl modification but lacks the C-terminal cholesterol moiety.

Plates (Black frame, white well B & W IsoPlate High Protein Binding affinity polystyrene ELISA plates, cat#6005580, PerkinElmer) were coated with 1.5 µg/ml (100 µl/well) recombinant human Shh (Recombinant Human Sonic Hedgehog C24II amino terminal peptide, cat #1845-SH-025/CF, R&D Systems) in PBS or with 100 µl/well of 3% (vol/vol) Shh conditioned media (CM) diluted in PBS. The plates were sealed and placed on a shaker overnight at 5° C. The next day, the plates were washed 4 times with PBS with 0.05% Tween 20 (PBS-T). The plates were blocked with 1% essentially globulin-free BSA (Sigma-Aldrich cat #3156) diluted in PBS for one hour at room temperature. The plates were washed four times with PBS-T. Titrations of purified antibody (half log serial dilutions over at least six logs with a starting concentration of 30 µg/mL) were made in 100 µl PBS-T and added into wells and incubated with shaking overnight at 4° C. Antibody controls included human IgG2 and IgG4 (Sigma-Aldrich, Cat. #15404 and #14639, respectively). The plates were washed four times with PBS-T. A 100 µl aliquot of Goat-anti-Human IgG H+L (KPL cat #074-1006) diluted at 1:50,000 in PBS-T was added to each well and the plates were incubated at room temperature for one hour with shaking. Following washing with PBS-T, the chemiluminescent Peroxidase substrate (Sigma cat #CPS-2-60) was added at room temperature and incubated for ten minutes with the plate covered by foil. Each well was read for 100 msec in the Spectromax 5e to determine RLU. The apparent binding affinity ($K_D$) of each antibody was determined using GraphPad Prism software and are shown in Table 19.

TABLE 19

Apparent Binding Affinity of Purified Antibodies to Immobilized Shh in an ELISA

| | Antibody Affinity $K_D$ (pM) | |
|---|---|---|
| Antibody | Shh-CM | Shh-C24II |
| 6D7 | 60 | 47 |
| 3H8 | 331 | 69 |
| 3H8OP | 685 | 82 |
| 1G1 | 30 | 61 |
| hIgG2 | No binding | No binding |
| hIgG4 | No binding | No binding |

Example 11

Determination of Binding Affinity of Purified Antibodies to the N-Terminal Signaling Domain of Shh The binding affinity of four purified recombinant antibodies expressed in a human IgG2 constant domain background was measured by high resolution Biacore. All experiments were performed using a Biacore T100 instrument at 23° C. Each recombinant IgG2 antibody (6D7, 3H8, 1G1, and 1H8) was diluted into 10 mM sodium acetate pH 4.0 (GE Healthcare, BR-1003-49) to a concentration of 20 μg/mL. All mAbs were covalently coupled to a CM5 biosensor chip using routine amine coupling chemistry. Immobilization levels for each antibody ranged from 177-838 RU. HBS-P running buffer (GE Healthcare, BR-1003-68, 0.01M HEPES, 0.15M NaCl, 0.005% P-20) was prepared by degassing followed by addition of BSA from a filtered stock to a final concentration of 100 μg/mL. For experiments with Shh-containing conditioned media (CM), a 1.5 mL aliquot was centrifuged for 10 minutes at 13,200 rpm. All Shh conditioned media samples and recombinant human Shh C24II (R&D Systems, Cat #1845-SH/CF, Lot #MJC09) were diluted into the HBS-P running buffer running. Shh samples were randomly injected in triplicate with several buffer inject cycles interspersed for double referencing. All sensorgram data were processed using Scrubber and fit to a 1:1 interaction model (including a term $k_m$ for mass transport) using CLAMP. A bulk refractive index factor was necessary to fit the sensorgrams of the top conditioned media concentration for mAb 1H8 owing to the significant bulk refractive index difference between the conditioned media and the running buffer. The resulting binding constants are listed in Table 20.

Asterisks in Table 20 indicate the kinetics are not completely reliable since the reactions for these mAbs are extremely mass transport limited owing to the almost diffusion controlled association rates. However, the resulting equilibrium dissociation constants ($K_D = k_d * k_m / k_a * k_m$) are reliable since any mass transport effects, $k_m$, on the measured kinetics are canceled out when the quotient is taken to calculate a reliable $K_D$. In addition, the binding of Shh (both CM and C24II peptide forms) to mAb 6D7 showed some complexity in the sensorgrams, and therefore the $K_D$ determined should be considered only an estimate.

TABLE 20

Binding affinities for Purified Antibodies to Shh Determined with High Resolution Biacore.

| MAb | Shh | $R_{max}$ | $k_a$ (M − 1s − 1) | $k_d$ (s − 1) | $K_D$ (pM) |
|---|---|---|---|---|---|
| 1G1 | CM | 75 | $9.00 \times 10^7$* | $2.85 \times 10^{-2}$* | 317 |
| 1G1 | C24II peptide | 53 | $1.73 \times 10^7$* | $6.53 \times 10^{-3}$* | 377 |
| 1H8 | CM | 104, 62 | $6.71 \times 10^5$ | $2.89 \times 10^{-3}$ | $4.31 \times 10^3$ |
| 1H8 | C24II peptide | 68, 39 | $4.86 \times 10^5$ | $2.09 \times 10^{-3}$ | $4.30 \times 10^3$ |
| 3H8 | CM | 130, 76 | $2.27 \times 10^6$ | $1.28 \times 10^{-5}$ | 5.6 |
| 3H8 | C24II peptide | 40, 20 | $1.06 \times 10^6$ | $2.83 \times 10^{-5}$ | 26.7 |
| 6D7 | CM | 20, 53 | $6.86 \times 10^7$* | $2.36 \times 10^{-4}$* | 3.4 |
| 6D7 | C24II peptide | 42, 45 | $2.31 \times 10^7$* | $3.11 \times 10^{-4}$* | 13.5 |

*not completely reliable

Example 12

Determination of Binding Affinity of Purified Antibodies to Full Length Shh Expressed on the Cell Surface The binding affinity of the purified antibodies for full length Shh ectopically expressed on the surface of a pool of stable HEK 293 cells was determined using flow cytometry. HEK 293-Shh-FL cells were mixed with various dilutions of hybridoma-derived antibody in PBS such that the final concentration of antibody ranged from 20 nM to 80 μM. Antibody was mixed with cells at approximately 74,000 cells/well in a final volume of 300 μl in a polypropylene microtiter plate. The plate was incubated with shaking for 5 hours at 4° C. After washing with ice-cold PBS, 225 μL of 99 nM Cy5 goat α-human polyclonal antibody (Jackson ImmunoResearch Laboratories, cat#109-175-008) was added to cells bound with 3H8 and 6D7. The plates were shaken for 20 minutes at 4° C. The mean fluorescence of 10,000 events was recorded for each sample using FACS Canto II HTS flow cytometry instrumentation. A plot of the mean fluorescence as a function of antibody concentration was fit nonlinearly with Scientist 3.0 software to estimate $K_D$. The results are shown in Table 21.

TABLE 21

Binding Affinity/Avidity of Purified Antibodies to Shh Stably Expressed on the Surface of HEK293 cells.

| MAb | isotype | $K_D$ (pM) | 95% CI (pM) |
|---|---|---|---|
| 6D7 | hIgG4 | 107 | ±40 |
| 3H8 | hIgG4 | 250 | ±141 |

The binding affinity of purified recombinant antibodies constructed with a human IgG2 constant region was also determined for full length Shh expressed on the surface of a stable clone of CAOV3 ovarian cancer cells using flow cytometry according to the method described above. Cells were mixed with various dilutions of antibody in final volume of 300 μl PBS and incubated at a concentration of 84,000 cells/well. The plate was incubated with shaking for 5 hours at 4° C. After washing with ice-cold PBS, cells bound with human anti-Shh antibody were stained with Cy5 goat α-human secondary antibody as described above. A plot of the mean fluorescence as a function of antibody concentration was fit nonlinearly with Scientist 3.0 software to estimate $K_D$. Results are reported in Table 22.

TABLE 22

Binding Affinity/Avidity of Purified Antibodies to Shh Stably Over-expressed on the Surface of CAOV3 cells.

| MAb | isotype | $K_D$ (pM) | 95% CI (pM) |
|---|---|---|---|
| 6D7 | hIgG2 | 37.1 | ±19.4 |
| 1G1 | hIgG2 | 46.5 | ±32.4 |
| 3H8 | hIgG2 | 68.2 | ±30.4 |
| 1H8 | hIgG2 | 1520 | ±460 |

Example 13

Elucidation of Epitope Bins for Purified Still Antibodies using Competition Binding Assays The binding of biotinylated, purified antibodies to recombinant human Shh-N was determined in the presence of excess amounts of unlabeled competitor antibody using an ELISA-based method (essentially as described in Example 10).

Antibodies 6D7 and 3H8 were biotinylated with the Pierce EZ-Link NHS PEG4-Biotin kit (Cat #21329) according to the manufacturer's instructions. Briefly, a 500 µg aliquot of each antibody was buffer-exchanged into BupH Phosphate Buffered Saline (Pierce cat #28372) using a Zeba Desalt Spin Column. Ultrapure water (170 µl) was used to dissolve 2 mg of NHS PEG4-Biotin for preparation of a 20 mM stock solution. The appropriate amount of IgG and biotin to label the antibody with 3-5 molecules of biotin per IgG molecule was calculated based on the manufacturers" recommendation. IgG and biotin was mixed and incubated on ice for 2 hrs, and the unreacted NHS PEG4-Biotin was removed with a Zeba Desalt column. Labeling efficiency was determined by measuring the change in the absorbance at 500 nm of the HABA/ Avidin solution following addition of biotinylated IgG and calculated according to manufacturers' instructions.

Plates (Black frame, white well B & W IsoPlate High Protein Binding affinity polystyrene ELISA plates, cat#6005580, PerkinElmer) were coated with 100 µl/well of 3% (vol/vol) Shh conditioned media (CM) diluted in PBS by incubation overnight at 5° C. with shaking. The next day, the plates were washed four times with PBS-T then blocked with 1% BSA in PBS-T for 5 hours at 5° C.

Ten-fold dilutions of each biotinylated antibody were made over a six log concentration range (between and 3 µg/ml and 1 µg/ml), and binding of each dilution of biotinylated antibody was measured in the Shh-binding ELISA in the absence or presence of excess unlabeled competitor antibody. Each unlabeled competitor antibody was included at various concentrations above the measured $K_D$ for that competitor antibody. Concentrations of $K_D+1$, $K_D+2$, $K_D+4$, $K_D+8$, and $K_D+16$ of each competitor antibody were mixed with the various dilutions of each biotinylated antibody. Dilutions of biotinylated antibody with or without unlabeled competitor antibody were added in a final volume of 100 µl of PBS-T after blocking and washing the plates with PBS-T and incubated with shaking overnight at 5° C. The following day, the plates were washed four times with 200 µl PBS-T. Streptavidin-HRP (R&D Systems cat #DY998 lot1157772) was diluted at 1:400 in PBS-T and 100 µl was added to each well followed by incubation at room temperature for two hours with shaking. After washing with PBS-T, chemiluminescent peroxidase substrate (Sigma CPS-2-60) was added (100 µl/well) and incubated at room temperature for ten minutes with the plate covered by foil. Each well was read for 100 msec in the Spectromax 5e to determine RLU.

Competition was demonstrated by displacement of the binding curve for each labeled antibody to the right along the x-axis (concentration of biotinylated antibody), resulting in an increase in the apparent $K_D$ for the labeled antibody. Antibodies that showed cross-competition were defined as occupying a common epitope bin.

Unlabeled 6D7 successfully competed binding of biotinylated 6D7, as expected. Increasing concentrations of excess 3H8 progressively displaced the binding curve of biotinylated 3H8 to the right, resulting in a five-fold increase in the apparent $K_D$ for labeled 6D7 at the highest concentration of unlabeled 3H8. Neither 1G1 nor 1H8 had any effect on the binding of 6D7. Binding of labeled 3H8 was competed by excess unlabeled 3H8. Excess unlabeled 6D7 effectively competed the binding of biotinylated 3H8, resulting in a nine-fold increase in the apparent $K_D$ at the highest concentration of unlabeled 6D7. Neither 1G1 nor 1H8 competed with labeled 3H8 for binding to immobilized Shh. These results indicate that 6D7 and 3H8 share a common, overlapping epitope that is not shared by either 1G1 or 1H8.

Example 14

Cross-Reactivity of Purified Shh Antibodies to Human Ihh and Dhh and Mouse Shh/Ihh The cross-reactivity of purified antibodies was tested against human hedgehog family members Ihh and Dhh and against the mouse orthologs of Shh, Ihh, and Dhh. Human and mouse Ihh share 100% sequence identity in the N-terminal signaling domain, thus only one protein was used to assess antibody binding.

Cross-reactivity experiments were carried out and measured using an ELISA based assay (as described in Example 10). Briefly, plates were coated with 100 µl of a PBS solution containing 1-2 µg/ml recombinant human Dhh (Recombinant Human/Mouse Indian Hedgehog C28 µl, amino terminal peptide, cat #1705-HH/CF, R&D Systems), human Dhh (Recombinant Human Desert Hedgehog C23II, amino terminal peptide, cat #4777-HH, R&D Systems) or mouse Shh (Recombinant Mouse Sonic Hedgehog C25II, N-terminus, cat #464-SH/CF, R&D Systems) and incubated with shaking overnight at 4° C. After washing with PBS-T and blocking with 1% BSA, antibody titrations spanning concentrations of 30 µg/ml to 1 µg/ml prepared by half log serial dilution in PBS-T were added to wells and incubated with shaking overnight at 4° C. Table 23 provides the results from calculating the apparent binding affinity ($K_D$) using GraphPad Prism software.

TABLE 23

Cross-Reactivity of Purified Antibodies to Immobilized Mouse Shh and to Human Hedgehog Family Members in an ELISA based format

| | Antibody Affinity $K_D$ (pM) | | |
|---|---|---|---|
| Antibody | Mouse Shh | Human/mouse Ihh | Human Dhh |
| 6D7 | 64 | 52 | No binding |
| 3H8 | 120 | >5000 | No binding |
| 1G1 | 82 | >5000 | Not tested |
| hIgG2 | No binding | No binding | No binding |
| hIgG4 | No binding | No binding | No binding |

The cross-reactivity of purified, sequence-optimized antibodies 6D7OP and 3H8OP antibodies to mouse Shh and Ihh was further corroborated using high resolution Biacore. The binding of the optimized forms of 6D7OP and 3H8OP to human Shh was confirmed in these experiments. Protein G was coupled to the CM5 chip surface using standard amine linkage chemistry. Protein G' was cleared of Tris using a Dulbecco's PBS equilibrated PD-10 column. The main 2.75-3.94 mL fraction (~0.78 mg/ml) was collected and an aliquot was diluted to 20 µg/ml in 10 mM acetate buffer pH 3.65. Approximately 500 RUs of protein G were covalently bound to the surface of flow chamber 2 (Fc2). At the beginning of each cycle, the relevant IgG (6D7OP or 3H8OP), diluted in HBS-P buffer to 0.5 µg/ml was flowed over the Protein G' surface at 5 µL/min for 50 s, followed by a 60 s stabilization period. Immobilization levels were reproducible between cycles. IgG immobilization levels were kept low to avoid mass transport effects on affinity determination (100 RU for 6D7 and 135 RU for 3H8). To minimize any potential mass transport effects, analyte was injected at a high flow rate of 50 µl/min for 300s, and dissociation was monitored for 1200 seconds, after which the surface was regenerated with two 40 second pulses of glycine pH 1.75 at flow rate of 30 μl/min. All the sensorgrams were fitted in the T-100 evaluation software using the Langmuir 1:1 model, with RI=0, global kon, global koff and global Rmax settings (data was double referenced; hence there was no bulk RI refractive index change).

The binding affinity of purified antibodies to human Shh (Table 24) was nearly identical to previous observations with 6D7 and 3H8 prior to sequence optimization (compare to Table 20). Further, the binding affinity of each sequence-optimized antibody for mouse Shh was nearly the same as that observed for human Shh, which was expected based on the single amino acid difference between the two proteins in the N-terminal signaling domain.

TABLE 24

Binding affinities for Sequence Optimized Purified Antibodies to Human and Mouse SHH and IHH Determined with High Resolution Biacore

| mAb (amount of immob Ab) | $k_{on}$ (1/Ms) | $k_{off}$ (1/s) | $K_D$ (pM) | Chi2 ($RU^2$) |
|---|---|---|---|---|
| Human Shh | | | | |
| 3H8OP IgG1 (135 RU) | $5.4 \times 10^{6}$* | 0.00014 | 26.1 | 0.1 |
| 6D7OP IgG1 (100 RU) | $8.4 \times 10^{7}$* | 0.00025* | 3.0 | 0.09 |
| Mouse Shh | | | | |
| 3H8OP IgG1 (135 RU) | $5.2 \times 10^{6}$ | 0.00015 | 29 | 0.05 |
| 6D7OP IgG1 (100 RU) | $5.5 \times 10^{7}$* | 0.00019* | 3.5 | 0.05 |
| Human/Mouse Ihh | | | | |
| 3H8OP IgG1 (135 RU) | no binding | no binding | no binding | no binding |
| 6D7OP IgG1 (100 RU) | $3.8 \times 10^{7}$* | 0.0013* | 34.2 | 0.078 |

*indicates non-reliable measurement. The values measured are outside of the range that can be reliably measured by SPR technology (for on rates up to $1 \times 10^{6}$ $M^{-1}s^{-1}$). Such fast interactions are completely mass-transport limited, i.e. diffusion of the analyte to the sensor surface becomes the rate-limiting step in the complex formation.
! indicates that nonsensical values were obtained for rate constants, on the order of $10^{11}$ for the on rate, and >1s−1 for the off rate.

Example 15

Neutralization of Ihh Activity by Purified Shh Antibodies

This assay was performed to measure the ability of purified antibody to inhibit osteoblast differentiation of $C3H_{10}T1/2$ cells induced by Indian hedgehog.

Purified antibody 6D7OP was shown to bind to human and mouse Indian hedgehog (Ihh) in both the ELISA and Biacore formats. The neutralization activity of this antibody was assessed in the osteoblast differentiation assay.

The osteoblast differentiation assay was performed essentially as described above in is Example 9 with a few modifications. $C3H_{10}T1/2$ cells were seeded in 384 well clear bottom plates at 5000 cells/well in seeding media and incubated overnight at 37° C., 5% $CO_2$. Antibodies were serially diluted in half log or two fold increments in Assay Medium and combined with an equal volume of a modified form of the N-terminal signaling domain of Ihh in which the cysteine at position 28 is replace with two isoleucine residues (IHH-N C28II, R&D Systems, cat #1705-HH). The final concentration of Ihh-N C28II used in the assay was 2 μg/ml. Titrated antibodies were preincubated with Ihh-N C28II for 45 min in a polypropylene dilution plate at 37° C., 5% $CO_2$. The final concentration of antibodies ranged from 25 μg/ml to 30 ng/ml. After the preincubation step was completed, seeding media was removed from all wells and replaced with 30 μl of medium containing a mixture of Ihh and antibody. The cells were incubated for 72 h at 37° C., 5% $CO_2$.

Osteoblast differentiation was assessed by the production of alkaline phosphatase as described above. Data analysis was performed with GraphPad Prism and $IC_{50}$ values are reported in Table 25. 6D7OP inhibited osteoblast differentiation induced by Ihh, indicating that binding of the ligand by the antibody results in neutralization of biological activity; whereas 3H8OP, which does not bind Ihh, had no effect on its activity.

TABLE 25

6D7OP but not 3H8OP Neutralizes Ihh Activity in the C3H10T1/2 Cell Osteogenesis Assay

| Antibody | $IC_{50}$ (nM) |
|---|---|
| 6D7OP | 16.3 |
| 3H8OP | No inhibition observed |

Example 16

Determination of In Vivo Activity of Purified Antibodies Evaluation of the Pharmacodynamic Modulation of Mouse Gli1 and PTC1 in the Stroma of COLO205 Xenograft Tumors The Colo205 human colorectal adenocarcinoma cell were obtained from ATCC and maintained in RPMI 1640, 10% FBS and 1% L-glutamine. Xenograft tumors were established in female nude mice following subcutaneous implantation of $4 \times 10^{6}$ cells/mouse into the right flank. Tumors grew to approximately 200 $mm^3$ at which point mice received a single intraperitoneal dose of vehicle or antibody at 1, 3, or 10 mg/kg. Mice were sacrificed three days post dose and tumors were excised. Collected tumors were minced and immediately preserved in 5 ml RNALater at 4° C. overnight. Subsequently, preserved tumors were stored at −20° C. until RNA isolation occurred.

RNA was extracted from tumors using RNeasy kits (cat #74104, Qiagen) according to the manufacturer's instructions. A tumor chunk was homogenized using the Fast Prep 24 homogenizer instrument on setting 6.0 for 40 sec. Debris was pelleted by centrifugation at 4000 RCF for 5 minutes at RT. An equal volume of 70% ethanol was added to the supernatant and the mixture was added to the RNeasy column. The column was equilibrated with 4 ml of Buffer RW1 and twice with 2 ml Buffer RPE. RNA was eluted with 270 μl RNase-free water and stored at −80° C. RNA quantity and quality were assessed using the Agilent RNA 6000 Nano kit (Cat #5067-1511).

The levels of mouse Gli1 and Ptc1 in tumors were determined relative to mouse HPRT1 using quantitative RT-PCR. cDNA was synthesized from 2 μg of RNA using the High Capacity cDNA Reverse Transcription kit (cat #4368814, ABI). Reactions were incubated 25° C. for 15 minutes, 37° C. for 2 hours, 85° C. for 5 minutes, before holding at 4° C. cDNA samples were diluted to a volume of 200 μl with RNase-free water. Reaction mixtures for qRT-PCR contained 5 μl of cDNA from each sample, 1 μl of each primer/probe set, and 10 μl of 2× TaqMan buffer (ABI cat #4369514) in a final volume of 20 μl. The ABI primer/probe sets included murine HPRT control gene (Mm00446968_m1), murine Gli1 (Mm00494654_m1), and murine Ptc1 (Mm00436026_m1).

Samples were heated to 50° C. for 2 minutes followed by heating to 95° C. for 10 minutes. Cycling was carried out at 95° C. for 15 seconds and 60° C. for 1 minute for forty cycles on the ABI 7900HT Fast Real-time PCR system. The amount of mouse Gli1 and Ptc1 RNA in each sample was determined by calculating the delta delta Ct value for each sample is using HPRT1 as the internal standard.

A significant reduction in the levels of mouse Gli1 and Ptc1 was observed (FIG. 1), even at the lowest dose tested (1 mg/kg), exhibiting the robust neutralizing activity of each antibody. Each antibody consistently reduced the levels of mGli1 to a greater extent than mPtc1.

Example 17

Determination of the Pharmacokinetic-Pharmacodynamic Relationship for Purified Antibodies Using the Colo205 Xenograft Model Colo205 tumors were established in the flank of female nude mice as described in Example 14. When the tumors reached approximately 200 mm$^3$ in size, mice received a single IP dose of 6D7, 3H8, or 1G1 at either 0.5 or 1.0 mg/kg. Groups of five mice were sacrificed at various times after dosing (0.5, 1, 2, 4, 6, 24, 48, 72, hours and 7 and 14 days). Serum was collected by cardiac puncture and 500-800 ml of blood was transferred into serum-separator Microtainer tubes (BD catalog #365956). Blood samples were allowed to clot for 20-30 minutes at room temperature and then were centrifuged at 13000 rpm for 10 minutes. The entire amount of serum was collected into 1.7 ml Eppendorf tubes and stored at −80° C. until further processing to determine the concentration of the injected test antibody. Tumor tissue was excised from sacrificed animals and preserved in RNALater as described above until RNA isolation occurred.

Figure 2:
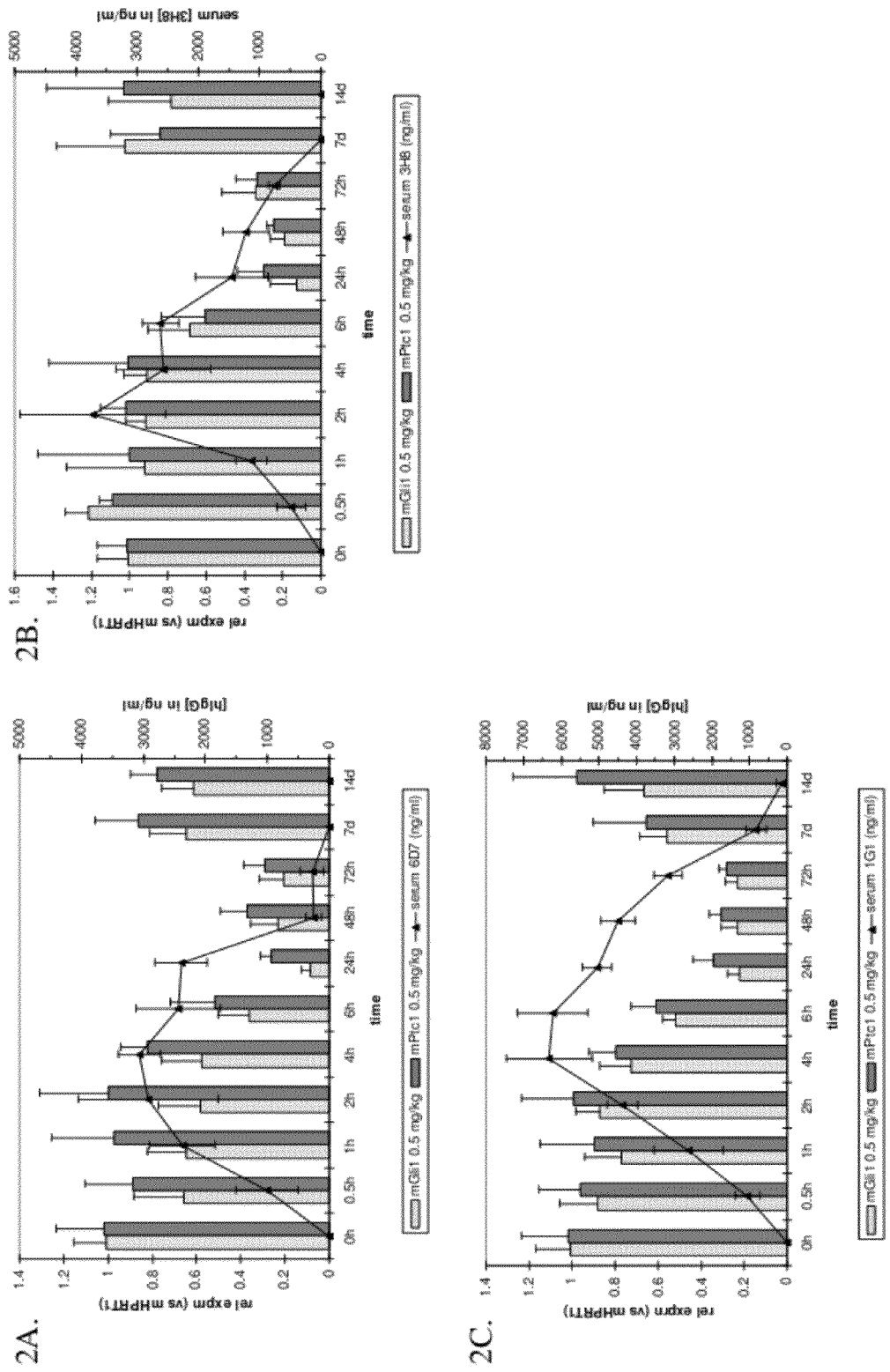
FIG. 2 is comprised of three panels depicting the pharmacokinetics of particular antibodies following a single 0.5 mg/kg dose as a line graph relative to the levels of the stromal hedgehog targets mouse Gli1 and Ptc1 in Colo205 xenograft tumors shown in bar chart form.

Serum concentrations of human antibody were determined using a qualified ELISA protocol measuring total human IgG that employs an anti-human HC+LC capture and anti-human HC+LC detection. ELISA plates were coated with 0.5 μg/ml goat anti-human IgG (Fc specific) overnight at 2-8° C., washed with PBS, 0.05% Tween 20 and blocked for 1-2 hours at room temperature with I-Block Buffer (Tropix). MAb reference standard, quality control (QC) and test sample dilutions were prepared in 10% serum (assay matrix) and added to blocked plates for 2 hour at room temperature. Plates were washed as above and incubated an additional 1 hour at room temperature with 1:20000 dilution of HRP-goat anti-human IgG Fc. Unbound detection antibody was removed by washing, and 100 μl of TMB substrate was added to plate wells for 5 min. The color development was stopped by addition of 50 μl of 2M $H_2SO_4$. Plates were read within 15 min at 450 nm with SpectraMax Plus 384 plate reader (Molecular Devices). Antibody concentrations in QC and test sample dilutions on each plate were quantitated using the reference is standard curve for that plate. The assay range was 31-4000 ng/ml in 100% serum. Pharmacokinetic (PK) analysis was conducted using WinNonLin (version 5.2, Pharsight Corp., Mountain View, Calif.). PK parameters determined for each antibody are shown in Table 26. Each antibody exhibited maximal reduction of mGli1 and mPtc1 levels by 80-90% at 24 hrs post dose (FIG. 2). Similar levels of inhibition were maintained through 72 hrs. However, mGli1 and Ptc1 levels began to rebound within 7 days of dosing for each antibody.

TABLE 26

PK Parameters for 6D7, 3H8, and 1G1 in Nude Mice.

| mAb | Dose (mg/kg) | Tmax (day) | $C_{max}$, ng/ml | $AUC_{all}$ ng * d/ml | $AUC_{INF}$ ng * d/ml | CL, ml/kg/d | T½ (day) |
|---|---|---|---|---|---|---|---|
| 6D7 IgG4 | 0.5 | 0.17 | 3060 | 3640 | 3850 | 129.9 | 0.72 |
|  | 1.0 | 0.17 | 7650 | 11050 | 11090 | 90.19 | 0.82 |
| 3H8 IgG4 | 0.5 | 0.083 | 3730 | 4410 | 6870 | 72.8 | 2.13 |
|  | 1.0 | 0.25 | 7470 | 17700 | 19200 | 52.1 | 1.88 |
| 1G1 IgG2 | 0.5 | 0.17 | 6323 | 23672 | 24199 | 20.7 | 2.55 |
|  | 1.0 | 1.0 | 13920 | 57378 | 58603 | 17.1 | 2.49 |

Example 18

Determination of Pharmacokinetics for Sequence-Optimized Purified Antibodies in the Rat Pharmacokinetic analysis of 6D7OP and 3H8OP was also done in rats. A single intravenous bolus dose of 1, 10, 30 mg/kg 6D7OP or 1, 10, 28 mg/kg 3H8OP was administered to Hans Wistar rats. Blood samples were taken via tail vein without any anti-coagulant agent at the following times: 0, 1, 4, 8 and 24 hrs, 2, 4, 7, 10, 15, 21 and 28 days post-dosing. Blood samples were spun and 100 μl of serum were aliquoted and frozen. The serum concentrations of mAb were determined using the ELISA method described above that measures total human IgG. Noncompartmental analysis was performed on individual animal serum concentration data using WinNonlin Professional (version 5.2, Pharsight Corp., Mountain View, Calif.) and a summary of the pharmacokinetic data is presented in Table 27.

TABLE 27

Pharmacokinetic Parameters for 3H8OP and 6D7OP in Rat

| mAb | Dose | Result | $C_{max}$, μg/ml | $AUC_{all}$, μg * d/ml | $AUC_{INF}$ μg * d/ml | CL, ml/kg/d | T½, d |
|---|---|---|---|---|---|---|---|
| 3H8OP | 1 mg/kg | Mean | 25.535 | 78.177 | 80.384 | 12.641 | 5.101 |
|  |  | SD | 6.235 | 9.482 | 11.421 | 1.701 | 1.29 |
|  | 10 mg/kg | Mean | 203.118 | 856.939 | 1043.372 | 9.805 | 11.806 |
|  |  | SD | 80.207 | 141.407 | 165.158 | 1.753 | 0.644 |
|  | 28 mg/kg | Mean | 550.726 | 2597.401 | 3264.566 | 8.761 | 12.624 |
|  |  | SD | 112.445 | 342.851 | 567.934 | 1.283 | 2.53 |
| 6D7OP | 1 mg/kg | Mean | 13.736 | 26.739 | 26.87 | 38.552 | 2.71 |
|  |  | SD | 4.592 | 6.04 | 6.041 | 7.248 | 0.326 |
|  | 10 mg/kg | Mean | 137.361 | 923.255 | 1015.974 | 10.049 | 8.554 |
|  |  | SD | 44.406 | 105.7 | 155.962 | 1.618 | 2.747 |

TABLE 27-continued

Pharmacokinetic Parameters for 3H8OP and 6D7OP in Rat

| mAb | Dose | Result | $C_{max}$, µg/ml | $AUC_{all}$, µg * d/ml | $AUC_{INF}$ µg * d/ml | CL, ml/kg/d | T½, d |
|---|---|---|---|---|---|---|---|
| | 30 mg/kg | Mean | 649.822 | 3396.055 | 3968.664 | 7.591 | 10.372 |
| | | SD | 113.564 | 268.321 | 278.672 | 0.538 | 1.053 |

$AUC_{ALL}$ area under the concentration - time curve from time zero to the last measurable time point;
$AUC_{inf}$ area under the concentration - time curve from zero to infinity;
CL systemic clearance;
$C_{max}$ observed peak concentration;
T½ terminal-phase elimination half-life The PK of 6D7OP appears to be nonlinear with respect to dose in the rat. The CL decreased with increasing dose from 38.552 mL/kg/d at the 1 mg/kg dose level to 10.049 mL/kg/d at the 10 mg/kg. The nonlinearity of 3H8OP was not as apparent as 6D7OP. In dose groups of 10 mg/kg or above, the CL of 6D7OP and 3H8OP was within the expected range for a human IgG in rat. The terminal-phase half-lives of 3H8OP in rat are approximately 12 and 13 days for the 10 and 28 mg/kg groups, respectively. The terminal-phase half-lives of 6D7OP in rat are approximately 9 and 10 days for 10 and 30 mg/kg groups, respectively.

Example 19

Tumor Growth Inhibition of Purified Antibodies Corresponds to Pharmacodynamic Modulation of Hedgehog Target Genes in Mouse Stromal Cells in Various Xenograft Tumor Models (i) Demonstration of In Vivo Anti-Tumor Activity Using the Ht-29 Colon Carcinoma Xenograft Model.

Figure 3A:
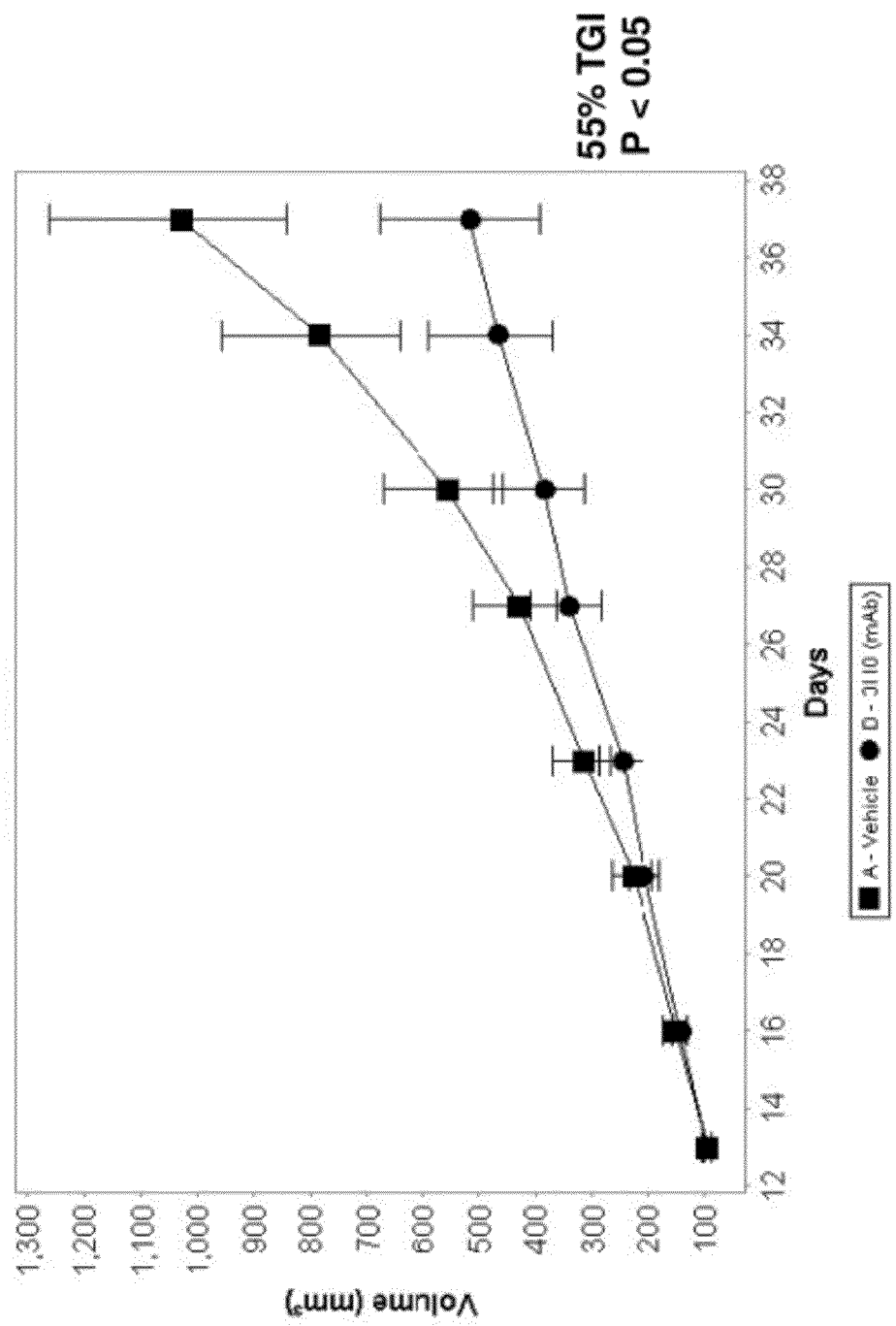
FIG. 3A depicts a line graph showing HT-29 xenograft tumor growth inhibition by antibody 3H8.

HT-29 colorectal tumor cells were obtained from ATCC and maintained at 37° C. in 5% $CO_2$ in McCoy's 5a medium containing 10% Fetal Bovine Serum and 1% L-glutamine. These cells were tested and found to be free of mycoplasma and viral contamination. HT-29 xenograft tumors were established in female nude mice following subcutaneous implantation of 3×10⁶ cells/mouse in 100 µl fetal bovine serum-free McCoy's 5a medium into the right flank region of 6-7 week old NCr nude female mice (Taconic, Hudson, N.Y.). Tumors grew to approximately 100 mm³ and randomized based on tumor size before dosing was initiated. Antibodies were dosed in 0.9% saline at 10 mg/kg biweekly for four weeks by means of intraperitoneal delivery. Tumor volume was monitored by caliper measurement twice a week using the formula 0.5×(length)×(width)². Statistical analysis was performed on mean tumor volumes at the end of the study using a one-tail t-test. Treatment with 3H8 inhibited the growth of HT-29 xenograft tumors by 55% (P<0.05) compared with vehicle treatment (FIG. 3).

Figure 3B:
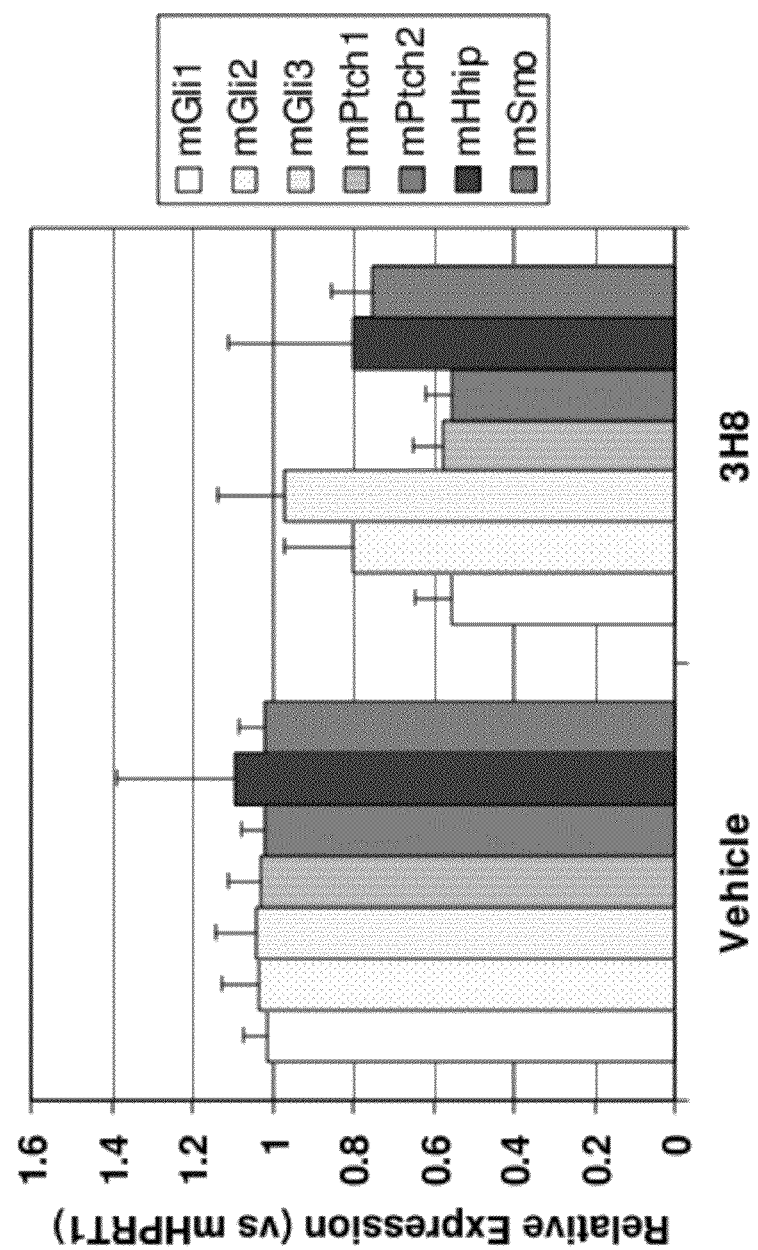
FIG. 3B depicts a bar chart showing the pharmacodynamic effects of antibody 3H8 on hedgehog target genes expressed in the stroma of HT-29 xenograft tumors whose growth was inhibited by antibody treatment.

The pharmacodynamic effect of 3H8 was evaluated in tumors excised at the end of the study three days post the last dose. Collected tumors were bisected and immediately preserved in 5 ml RNALater at 4° C. overnight or flash frozen in liquid nitrogen. Tumors preserved in RNALater were subsequently stored at −20° C. until RNA isolation occurred. The levels of mouse Gli1, Gli2, Gli3, Ptc1, Ptc2, Hhip, and Smo were determined relative to mouse HPRT1 using quantitative RT-PCR as described in Example 9. The following ABI TaqMan primers/probe sets were used: mouse Gli1, Mm00494654_m1; mouse Gli2, Mm01293117_m1; mouse Gli3, Mm00492333_m1; mouse Ptc1, Mm00436026_m1; mouse Ptc2, Mm00436047_m1; mouse Hhip, Mm01241503_m1; mouse Smoothened, Mm01162705_m1; and mouse HPRT1, Mm00446968_m1. Treatment with 3H8 results in an approximately 50% decrease in the levels of mouse Gli1, Ptc1, and Ptc2 (FIG. 3B).

(ii) Demonstration of in vivo anti-tumor activity using the primary colon carcinoma explant model HCXF-001.

An approximately 1 g primary colon carcinoma surgically removed from a 66 year old Caucasian male was obtained through Asterand (Detroit, Mich.) and implanted into SCID mice to establish a primary explant xenograft model. The primary tumor was rinsed with RPMI 1640 medium containing 10% FBS, 100 IU/ml penicillin, 0.1 mg/ml streptomycin and minced with scalpels. The minced tumor sample was held on ice until implantation. The minced tumor was loaded into 13-gauge cancer implant trocars and implanted into four mice by inserting the trocar subcutaneously into the right flank and dispensing the contents of the trocar under the dorsal fat pad. When the tumors (defined as passage 0, P0) reached 800-1000 mm³, they were excised and dissected into approximately 3×3×3 mm fragments. Single P0 tumor fragments were subpassaged in individual mice. Efficacy studies are typically done with tumors beyond passage 2 (P2).

Figure 4A:
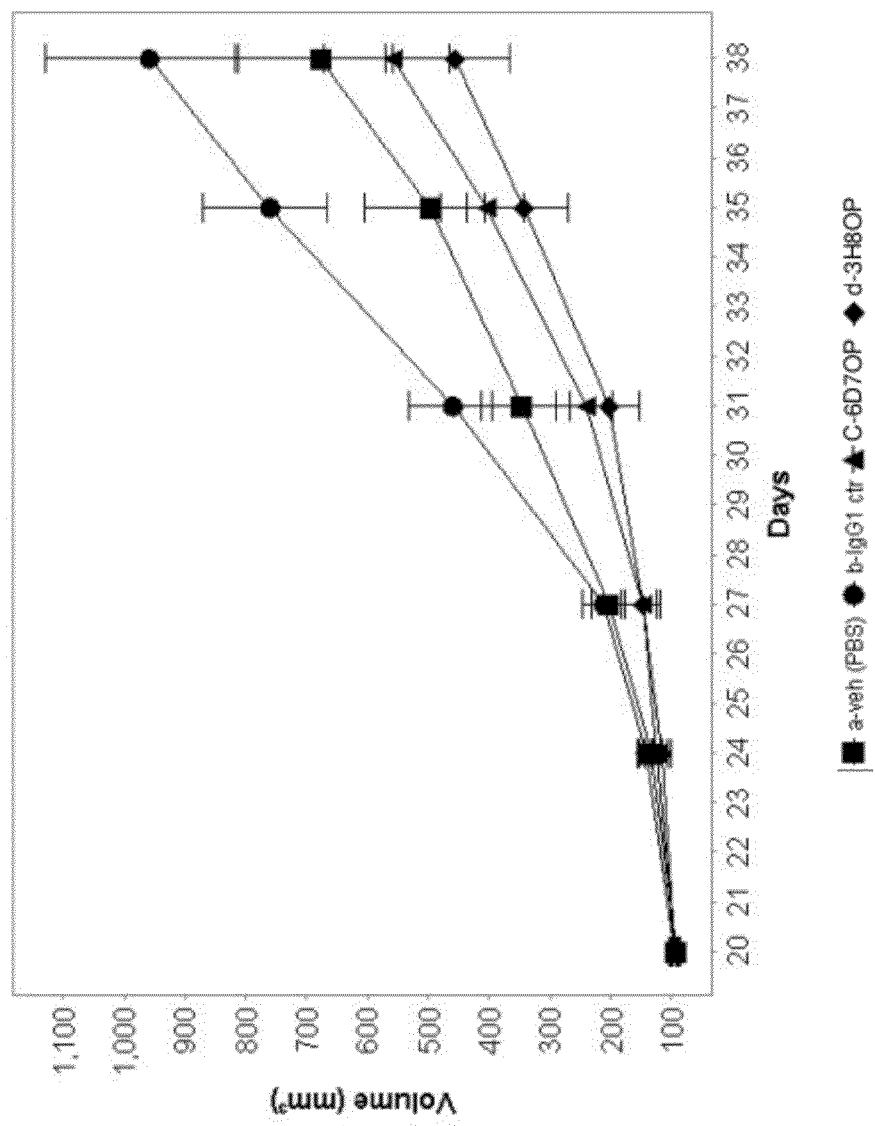
FIG. 4A depicts a line graph showing growth inhibition of the primary colon carcinoma tumor model HCXF-001 by particular antibodies in nude mice.
Figure 4B:
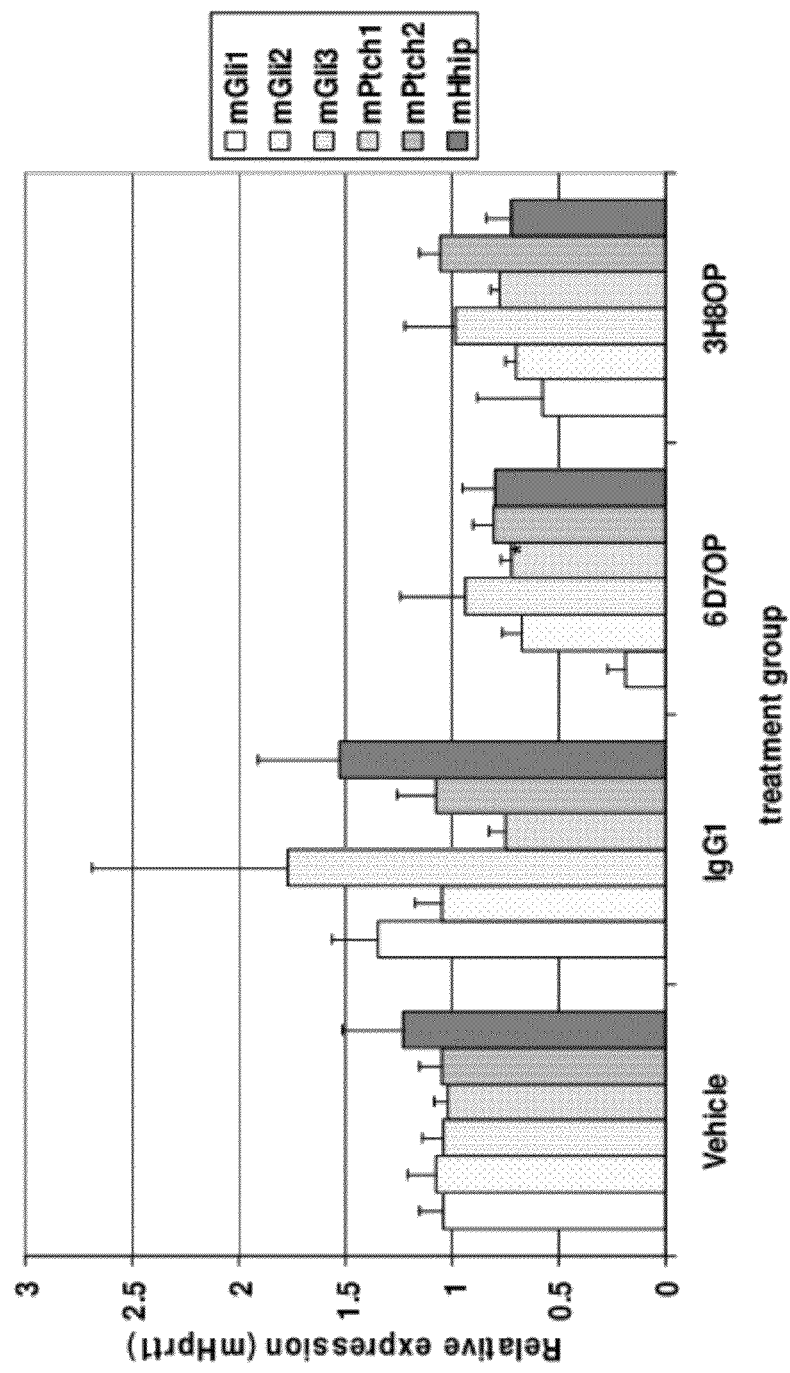
FIG. 4B depicts a bar chart showing the results from pharmacodynamic modulation of hedgehog target genes in the stroma of HXCF-001 xenograft tumors whose growth was inhibited by treatment with particular antibodies.

Individual SCID mice were implanted subcutaneously with a single tumor fragment and treatment with anti-Shh antibodies was initiated when the average tumor volume reached approximately 100-200 mm³. The antibodies were administered in 0.9% saline IP at 10 mg/kg biweekly for four weeks once treatment initiated. Tumor volume was monitored by caliper measurement twice a week and statistical analysis was performed on the geometric mean of tumor volumes for each treatment group at the end of the study using a one-tail t-test. Animals in which tumors did not take were removed from each group. Modest inhibition of tumor growth was observed with treatment of 6D7OP or 3H8OP as single agents, particularly when compared to the growth of tumors in animals treated with the control IgG1 mAb (FIG. 4A). Treatment with 6D7OP or 3H8OP resulted in a 48-59% reduction in tumor size relative to the IgG1 control (P<0.05).

The pharmacodynamic effect of the anti-Shh antibodies was evaluated in tumors collected three days post the last dose as described above. The levels of stromal hedgehog target genes (mGli1, mGli2, mGli3, mPtc1, mPtc2, and mHhip) were determined relative to mHPRT1 using quantitative RT-PCR as described in Example 9 using the TaqMan primer/probe sets described above in Example 19. 6D7OP caused a dramatic reduction (>80%) in the level of mGli1; whereas, treatment with 3H8OP results in a more modest 50% decrease in mGli1 levels. More modest inhibition of mGli2, mPtc1, and Ptc2 was observed with both antibodies.

(iii) Demonstration of In Vivo Anti-Tumor Activity Using the Ht-55 Colon Xenograft Model.

Figure 5:
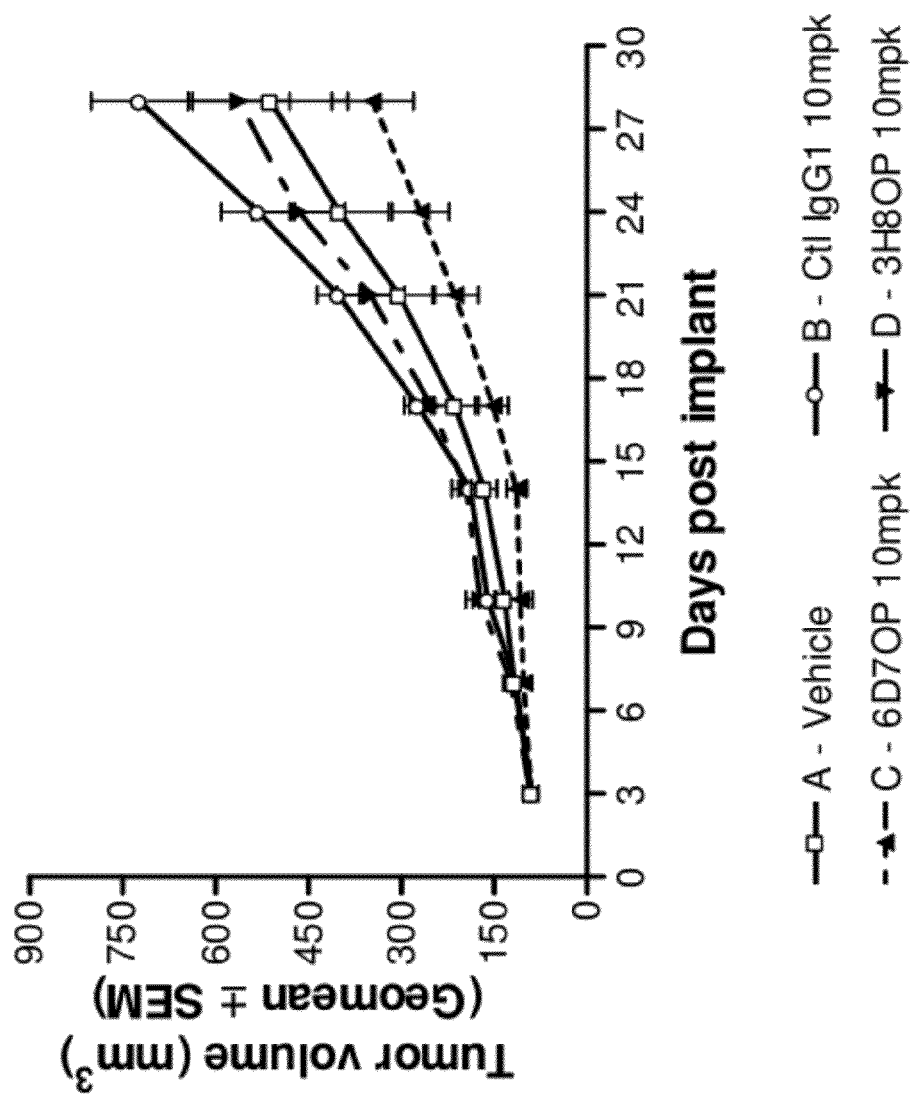
FIG. 5 depicts a line graph showing HT-55 xenograft tumor growth inhibition by antibody 6D7.

HT-55 colon carcinoma cells were obtained from the European Collection of Cell Cultures (ECACC) and maintained at 37° C. in 5% $CO_2$ in EMEM (EBSS), 2 mM Glutamine, 1% Non Essential Amino Acids (NEAA), and 20% Fetal Bovine Serum (FBS). These cells were tested and found to be free of mycoplasma and viral contamination (MAP). Xenograft tumors were established in female nude mice essentially as described above following subcutaneous implantation of $5 \times 10^6$ cells/mouse in 100 μl fetal bovine serum-free EMEM medium into the flank of 6-7 female nude mice. Tumors grew to approximately 100 mm³ and were randomized prior to dosing. Antibodies were dosed IP in 0.9% saline at 10 mg/kg biweekly for 3.5 weeks. Tumor volume was monitored by caliper measurement twice a week and statistical analysis was performed on the geometric mean of the tumor volumes for each treatment group at the end of the study using a one-tail t-test. Treatment with 6D7OP inhibited xenograft growth by 32% relative to the vehicle control and by 52% ($P<0.05$) relative to the IgG1 control (FIG. 5). 3H8OP had little to no effect on growth of the HT-55 tumors.

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. An isolated antibody or binding fragment thereof that binds to sonic Hedgehog Homolog, wherein the antibody or binding fragment thereof comprises:
   (a) a variable heavy (VH) chain complementarity determining region (CDR) 1, CDR2 and CDR3 of SEQ ID NO: 50; and
   (b) a variable light (VL) chain CDR1, CDR2 and CDR3 of SEQ ID NO: 54.

2. The isolated antibody or fragment thereof according to claim 1 wherein the VH sequence comprises the amino acid sequence as shown in SEQ ID NO:46 or SEQ ID NO:50.

3. The isolated antibody or fragment thereof according to claim 1 wherein the VL sequence comprises the amino acid sequence as shown in SEQ ID NO:48 or SEQ ID NO:52 or SEQ ID NO:54.

4. The isolated antibody or fragment thereof according to claim 2 wherein the VL sequence comprises the amino acid sequence as shown in SEQ ID NO:48 or SEQ ID NO:52 or SEQ ID NO:54.

5. The isolated antibody or fragment thereof according to claim 2 wherein the VH sequence comprises the amino acid sequence as shown in SEQ ID NO:46.

6. The isolated antibody or fragment thereof according to claim 3 wherein the VL sequence comprises the amino acid sequence as shown in SEQ ID NO:48.

7. The isolated antibody or fragment thereof according to claim 5 wherein the VL sequence comprises the amino acid sequence as shown in SEQ ID NO:48.

8. The isolated antibody or fragment thereof according to claim 2 wherein the VH sequence comprises the amino acid sequence as shown in SEQ ID NO:50.

9. The isolated antibody or fragment thereof according to claim 3 wherein the VL sequence comprises the amino acid sequence as shown in SEQ ID NO:54.

10. The isolated antibody or fragment thereof according to claim 8 wherein the VL sequence comprises the amino acid sequence as shown in SEQ ID NO:54.

11. The isolated antibody or fragment thereof according to claim 3 wherein the VL sequence comprises the amino acid sequence as shown in SEQ ID NO:52.

12. The isolated antibody or fragment thereof according to claim 8 wherein the VL sequence comprises the amino acid sequence as shown in SEQ ID NO:52.

13. The antibody or fragment thereof according to claim 1 wherein the antibody is a fully human monoclonal antibody or binding fragment of a fully human antibody.

14. The antibody or fragment thereof according to claim 7 wherein the antibody is a fully human monoclonal antibody or binding fragment of a fully human antibody.

15. The antibody or fragment thereof according to claim 10 wherein the antibody is a fully human monoclonal antibody or binding fragment of a fully human antibody.

16. The antibody or fragment thereof according to claim 12 wherein the antibody is a fully human monoclonal antibody or binding fragment of a fully human antibody.

17. The antibody or binding fragment thereof according to claim 1 wherein the antibody or fragment thereof is a Fab, Fab', F(ab')$_2$, Fv or dAb.

18. The antibody or binding fragment thereof according to claim 7 wherein the antibody or fragment thereof is a Fab, Fab', F(ab')$_2$, Fv or dAb.

19. The antibody or binding fragment thereof according to claim 10 wherein the antibody or fragment thereof is a Fab, Fab', F(ab')$_2$, Fv or dAb.

20. The antibody or binding fragment thereof according to claim 12 wherein the antibody or fragment thereof is a Fab, Fab', F(ab')$_2$, Fv or dAb.

21. A composition comprising the antibody or fragment thereof recited in claim 1.

22. A composition comprising the antibody or fragment thereof recited in claim 7.

23. A composition comprising the antibody or fragment thereof recited in claim 10.

24. A composition comprising the antibody or fragment thereof recited in claim 12.

* * * * *